(12) United States Patent
Najafi et al.

(10) Patent No.: US 8,415,497 B2
(45) Date of Patent: Apr. 9, 2013

(54) N-HALOGENATED AMINO COMPOUNDS AND DERIVATIVES

(75) Inventors: Ramin Najafi, Novato, CA (US); Rakesh K. Jain, Fremont, CA (US); Timothy P. Shiau, Oakland, CA (US); Eddy Low, Foster City, CA (US); Satheesh K. Nair, Emeryville, CA (US)

(73) Assignee: Novabay Pharmaceuticals, Inc., Emeryville, CA (US)

( * ) Notice: Subject to any disclaimer, the term of this patent is extended or adjusted under 35 U.S.C. 154(b) by 0 days.

(21) Appl. No.: 12/451,412

(22) PCT Filed: Dec. 28, 2007

(86) PCT No.: PCT/US2007/089143
§ 371 (c)(1),
(2), (4) Date: Aug. 18, 2010

(87) PCT Pub. No.: WO2008/083347
PCT Pub. Date: Jul. 10, 2008

(65) Prior Publication Data
US 2010/0311791 A1    Dec. 9, 2010

Related U.S. Application Data

(60) Provisional application No. 60/877,943, filed on Dec. 29, 2006.

(51) Int. Cl.
*C07C 309/04*    (2006.01)
*C07C 309/13*    (2006.01)

(52) U.S. Cl. ........................................ 562/104; 562/107

(58) Field of Classification Search .................. 562/104, 562/107
See application file for complete search history.

*Primary Examiner* — Johann Richter
*Assistant Examiner* — Kofi Adzamli
(74) *Attorney, Agent, or Firm* — Hamilton, DeSanctis & Cha, LLP

(57) ABSTRACT

The present invention relates to active bactericidal, antibacterial, anti-infective, antimicrobial, sporicidal, disinfectant, antifungal and antiviral compounds and compositions and to new uses of these compositions in therapy. This specification also describes methods of use for the new compounds and compositions. The specification further describes methods for preparing these compounds.

24 Claims, No Drawings

N-HALOGENATED AMINO COMPOUNDS AND DERIVATIVES

CROSS-REFERENCE TO RELATED APPLICATIONS

This application claims the benefit of U.S. Provisional Application Ser. No. 60/877,943, filed Dec. 29, 2006, which application is incorporated herein by reference.

FIELD OF THE INVENTION

The present application relates to bactericidal, antibacterial, anti-infective, antimicrobial, sporicidal, disinfectant, antifungal, germicidal and antiviral compounds and compositions based on amino compounds and their derivatives that have the ability to release halogen and to new uses of these compositions in therapy. In another variation, the present application relates to active bactericidal, antibacterial, anti-infective, antimicrobial, sporicidal, germicidal, disinfectant, antifungal and antiviral compounds and compositions and to new uses of these compositions in killing microbes and therapy. Because of their properties, the new products and compositions of the present application also have broad applications in animal health including animal husbandry and agriculture, for example, stock preservation of valuable seeds.

This specification also describes methods of use for the new compounds and compositions. The specification further describes methods for preparing these compounds. More specifically, these halogenated amino compounds and their derivatives are also referred to herein as amino compounds. The amino compound starting materials may be used in form of their esters, salts or other functional derivatives. The term halogen as used herein includes chloro and bromo, chloro being preferred.

With respect to the N-halogenatated and N,N-dihalogenated amino compounds, we provide new compositions with bactericidal, antibacterial, germicidal, anti-infective, sporicidal, antimicrobial, antifungal and antiviral properties. The present application also relates to compositions comprising the new N-halogenated and N,N-dihalogenated amino compounds and their derivatives with bactericidal, antibacterial, germicidal, anti-infective, sporicidal, antimicrobial, antifungal and antiviral properties.

BACKGROUND OF THE INVENTION

A body's immune cells, the neutrophils and macrophages that are known for their abilities to clear infection can generate reactive oxygen metabolites that destroy microorganisms and abnormal or neoplastic (cancerous) cells and modulate inflammatory responses. Neutrophils can be activated as a response to inflammatory stimuli, bacterial infection and/or other membrane changes. As a result, they produce super oxide radicals such as: $HOO^-$, $O_2^-$, and $OH^-$. Under acidic conditions, chloride ion ($Cl^-$) at physiological concentrations of 100-150 mM is oxidized by $H_2O_2$, which is catalyzed by myeloperoxidase (an enzyme within the neutrophils) to form hypochlorous acid (HOCl) following the reaction equation (Weiss S. J., Klein R., Slivka A., Wei M. *J. Clin. Invest.* 1982, September; 70(3): 598-607):

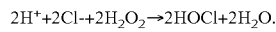

Physiological generation of HOCl is tightly regulated through feedback inhibition by an intricate network of biochemical signals. HOCl is generated at a concentration of $2\times10^{-7}$M per $10^6$ activated neutrophils (Lapenna D., Cuccurullo F., *Gen. Pharmacol.*, 1996, October 27(7): 1145-7). This quantity of HOCl is estimated to kill approximately $150\times10^6$ *E. coli* bacteria. Once HOCl is produced, it degrades rapidly by reacting with multiple oxidizable substrates within the complex cell system. Thus, the concentrations of reactive oxygen-metabolites are expected to fall to undetectable levels within hours. However, it has been demonstrated that neutrophils can use their HOCl to generate large quantities of a rather long-lived oxidants, such as N-chloramines. These long-lived oxidants are generated as monochloramines of taurine (NCT or N-chlorotaurine) and dichloramines of taurine (NNDCT, or N,N-dichlorotaurine) depending on the pH of the environment. These oxidants are powerful antimicrobials and play key roles within the defense system as well as modulating the cytokines and growth factors in the host body.

DESCRIPTION OF RELATED ART

U.S. Pat. No. 4,386,103 (S. A. Pogany et al.) discloses N,N-dichloroamino carboxylic acid derivatives, other than α-dichloroamino acid derivatives prepared from the corresponding amino carboxylic acids, that are potent germicidal and fungicidal agents.

U.S. Pat. No. 5,985,239 (A. A. Hussain et al.) discloses N-chloro-N-methyl glucamine and N-chloro-N-methyl glucamine esters and their use as agents for water disinfection and as mild oxidizing agents for the radiolabelling of oxidation-sensitive biomolecules.

U.S. Pat. No. 6,451,761 (N. M. van Gelder et al.) discloses N,N-dichloroamino sulfonic, phosphonic and carboxylic acids for the treatment of central nervous system disorders.

US Patent Publication No. US 2005/0065115 discloses an N,N-dihaloamino acid of the formula (I)

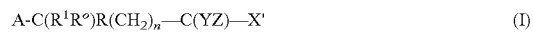

or a derivative thereof. A is hydrogen or $Hal_2N$— wherein Hal is halogen selected from the group consisting of chloro, bromo and iodo; R is a carbon carbon single bond or a divalent cycloalkylene radical with three to six carbon atoms, $R^1$ is hydrogen, lower alkyl or the group —COOH; $R^o$ is hydrogen or lower alkyl; n is 0 or an integer from 1 to 13, or $R^1$ and $R^o$ together with the carbon atom to which they attach form a $(C_3-C_6)$cycloalkyl ring; Y is hydrogen, lower alkyl or —$NH_2$ or —$NHal_2$; and Z is hydrogen or lower alkyl; and X' is hydrogen, —COOH, —$CONH_2$, —$SO_3H$, —$SO_2NH_2$, —P(=O)(OH)$_2$ or —B(OH)$_2$.

US Patent Publication No. US 2006/0247209 discloses N-halo- or N,N-dihaloamino acid of the formula (I))

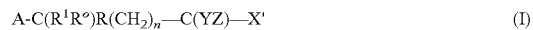

or a derivative thereof; wherein A is hydrogen, HalNH— or $Hal_2N$— wherein Hal is halogen selected from the group consisting of fluoro, chloro, bromo and iodo; R is a carbon carbon single bond or a divalent cycloalkylene radical with three to six carbon atoms, $R^1$ is hydrogen, lower alkyl or the group —COOH; $R^o$ is hydrogen or lower alkyl; n is 0 or an integer from 1 to 13, or $R^1$ and $R^o$ together with the carbon atom to which they attach form a $(C_3-C_6)$cycloalkyl ring; Y is hydrogen, lower alkyl or —$NH_2$ or —$NHal_2$; and Z is hydrogen or lower alkyl; and X' is hydrogen, —COOH, —$CONH_2$, —$SO_3H$, —$SO_2NH_2$, —P(=O)(OH)$_2$ or —B(OH)$_2$.

SUMMARY OF THE INVENTION

It is understood that any aspect or feature of the present application whether characterized as preferred or not characterized as preferred may be combined with any other aspect or feature of the present application, whether such other feature is characterized as preferred or not characterized as preferred. For example, a feature described as preferred, (for example, certain N-halo- or N,N-dihalo amino compounds of a specific formula) may be combined with another composition (N-halo- or N,N-dihalo amino compounds of another specific formula) without deviating from the present application. This statement also applies to any combination of substituents. For example, a substituent characterized as preferred may be combined with any other substituent not characterized as preferred. The terms "include(s)" or "comprise(s)" are used as open terms interchangeably in the text of this specification. It is also understood that the compounds of the present application may be prepared or used in the form of salts. This statement not only applies to the entire class of compounds described herein but also applies to individual compounds described throughout the specification and compounds not individually mentioned in this specification. Therefore, this specification will not always specifically mention salts; and even when salts are not specifically mentioned, it is understood that salts are included when referring to the compounds described in this specification.

DEFINITIONS

"Acyl", alone or in combination with another term, means a carbonyl or thioxocarbonyl group bonded to a radical selected from, for example, hydrido, alkyl, alkenyl, alkynyl, haloalkyl, alkoxy, alkoxyalkyl, haloalkoxy, aryl, heterocyclyl, heteroaryl, alkylsulfinylalkyl, alkylsulfonylalkyl, arylalkyl, cycloalkyl, cycloalkylalkyl, cycloalkenyl, alkylthio, arylthio, amino, alkylamino, dialkylamino, arylalkoxy, arylthio and alkylthioalkyl. Examples of "acyl" groups are formyl, acetyl, benzoyl, trifluoroacetyl, phthaloyl, malonyl, nicotinyl, propionyl, pentanoyl, 2-methylvaleryl group, ortho-, meta and para-toluoyl, xyloyl (all 7 isomers), 1-naphthoyl, 2-naphthoyl, cyclopentanoyl and cyclohexanoyl, phenylacetyl, 2-phenyl propionyl, 1-naphthylacetyl, 2-naphthylacetyl, methylcarbamoyl, benzylcarbamoyl, trichloroethylcarbamoyl, phenylthiocarbamoyl, dimethylureyl group, and the like. A subgroup of "acyl" is the group alkanoyl with the structure alkyl(C=O)—, wherein the alkyl group is as defined herein.

"Alkylaryl" means a monovalent monocyclic or bicyclic aromatic radical with an alkyl, haloalkyl, alkyloxy, or acyl substituent as defined herein with 1-3 carbon atoms. Non-limiting examples include the tolyl, the isopropylphenyl, the 1-methylnaphthyl, the 2-methylnaphthyl, the 2-ethylnaphthyl, the 4-trifluoromethylphenyl, the 3-methoxyphenyl, or the 4-methoxycarbonylphenyl group.

"Alkenyl" means straight or branched chain unsaturated radicals of 2 to 6 carbon atoms having at least one carbon-carbon double bond, including, but not limited to ethenyl, 1-propenyl, 2-propenyl(allyl), iso-propenyl, 2-methyl-1-propenyl, 1-butenyl, 2-butenyl and the like. An alkenyl group may also be part of a ring as a monocyclic (e.g., cyclobutenyl, cyclopentenyl, cyclohexenyl etc.) or bicyclic ring. An alkenyl group may contain 1-3 carbon-carbon double bonds, which can be cis or trans or combinations thereof. Alkenyl groups may be optionally substituted by 1 to 3 suitable substituents as defined below.

"Alkoxy" refers to the group "alkyl-O—", wherein alkyl is as defined below, and may include, for example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkyl" means linear or branched (such as methyl, ethyl, n-propyl, isopropyl, n-butyl, iso-butyl, secondary-butyl, tertiary-butyl); optionally substituted by 1 to 6 suitable substituents as defined below. Preferred alkyls include $(C_{1-3})$alkyl, most preferably methyl and ethyl.

"Alkoxyalkyl" refers to the group "-alkylene-O-alkyl" or "alkyl-O-alkylenyl-" or "alkyl-O-alkyl-" where alkylene (or alkylenyl) and alkyl are as defined herein. Examples of such group include 2-propoxyethylene, 3-methoxybutylene, and the like.

"Alkoxycarbonyl" means a monovalent radical having an alkoxy group, as herein defined with 1-5 carbons, that is attached to a carbonyl group. The lower alkoxycarbonyl includes, for example, methoxycarbonyl, ethoxycarbonyl, and isopropoxycarbonyl group.

"Alkylene" means a saturated hydrocarbon (straight chain or branched) wherein a hydrogen atom is removed from each of an internal or the terminal carbons such as methylene, ethylene, methylethylene, propylene, butylene, pentylene, hexylene, heptamethylene, decamethylene, dodecamethylene, octadecamethylene, 2-methyl tetramethylene, and 4-ethyl heptamethylene group, and the like.

"Alkylenyl" means a monovalent radical derived from an alkyl group by removal of a hydrogen atom.

"Alkynyl", means a hydrocarbon radical having at least one triple bond including, but not limited to, ethynyl, propynyl, 1-butynyl, 2-butynyl and the like.

"Amide" means a monovalent groups —C(=O)NH$_2$ or —NHC(=O)—Substituent, or the divalent groups =NC (=O)—Substituent, wherein the Substituent may be hydrogen, alkyl, cycloalkyl, cycloalkylakyl, aryl, heteroaryl as defined herein. Alternatively, "Amide" may be defined as —NH-Acyl or as =N-Acyl, wherein Acyl is as defined herein.

"Amine oxide" means a compound derived from a tertiary amine by the attachment of one oxygen atom to the nitrogen atom. Representative but non-exclusive examples include amine oxides derived from the tertiary amines included among the compounds described herein containing the group

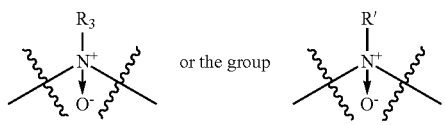

in which $R_3$ and R' are alkyl, cycloalkyl, aryl or arylalkyl.

"Arylalkyl" means a monovalent monocyclic or bicyclic aromatic radical attached to an alkyl group as defined herein with 1-4 carbon atoms. It includes an alkyl group substituted by from 1 to 3 aryl groups as herein defined, and includes groups such as benzyl, phenylethyl (2-phenethyl), α-naphthylmethyl, β-naphthylmethyl, diphenylmethyl and triphenylmethyl. An "arylalkyl" group also means an alkyl group substituted by from 1 to 3 substituted aryl groups, where one or more of the aryl groups may be substituted by one or more alkyl, alkoxy, nitro, halogen or cyano substituents such as the 4-methylbenzyl, 2,4,6-trimethylbenzyl, 4-methoxybenzyl, 4-nitrobenzyl, 4-chlorobenzyl, 4-bromobenzyl, 4-cyanobenzyl groups and the like.

"Aryl" means a monovalent monocyclic or bicyclic aromatic carbocyclic group of 6 to 14 ring atoms, and may include, for example, phenyl, naphthyl, bi-phenyl, tetrahydronaphthyl, anthryl, indanyl and the like. The aryl group may be optionally substituted by 1 to 3 suitable substituents as defined below. The aryl ring may be optionally fused to a 5-, 6- or 7-membered monocyclic non-aromatic ring optionally containing 1 or 2 heteroatoms independently selected from oxygen, nitrogen, or sulfur, the remaining ring atoms being C.

"Aryloxy" means a group "—O—Ar" where Ar is an aryl group or substituted aryl group as these terms are defined herein.

"Carbamate" means an ester of carbamic acid $H_2NC(=O)OH$ or of N-substituted carbamic acids.

"Carbocyclic" means a cyclic group in which all of the atoms of the ring, that may be saturated or partially saturated, are carbon atoms. Representative carbocyclic groups include cycloalkyl groups as described above. The term carbocyclic subsumes the term aryl.

"Cycloalkyl" means a mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl and the like); optionally containing 1 or 2 double bonds and optionally substituted by 1 to 3 suitable substituents as defined below.

"Cycloalkylalkyl" means a cycloalkyl ring as defined herein linked to an alkyl group as defined herein with 1-3 carbon atoms.

"Halogen" or "halo" means fluoro, chloro, bromo or iodo or fluoride, chloride, bromide or iodide. In accordance with the present disclosure, in certain embodiments, its scope may be narrower than this definition. For example, when referring to the term "N-halo amino compound" the term "halo" is limited to chloro or bromo.

"Haloalkyl" means an alkyl as defined above substituted with one or more, preferably one to 6, of the same or different halo atoms, in this case halo is limited to fluoro, chloro or bromo. Preferred are haloalkyl groups with 1-6 halo-atoms. Non-exclusive examples include monofluoromethyl, difluoromethyl, trifluoromethyl, pentafluoroethyl, chloromethyl, dichloromethyl and 1,2-dichloroethyl. Preferred lower haloalkyl groups have 1-2 carbon atoms.

"Heteroaryl" refers to an aromatic heterocyclic group comprising 4 to 10 ring atoms, usually with at least one heteroatom selected from O, S and N in the ring, the remaining ring atoms being C. In addition to the heteroatom, the aromatic group may optionally have up to four N atoms in the ring. The term "heteroaryl" includes monovalent monocyclic or bicyclic aromatic radicals. Examples of heteroaryl group includes pyridyl (for example, 2-pyridyl), pyrazinyl, pyrimidinyl, pyridazinyl, thienyl (for example, 2-thienyl), furyl, imidazolyl, pyrrolyl, oxazolyl (e.g., 1,3-oxazolyl, isoxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,4-oxadiazolyl), thiadiazolyl (e.g., 1,3,4-thiadiazolyl), quinolyl (for example, 2-quinolinyl), isoquinolyl, benzothienyl, benzofuryl, indolyl (for example, indol-1-yl), 4-quinazolinyl, and the like. The heteroaryl group may be optionally substituted by 1 to 3 suitable substituents as defined below. Particularly preferred heteroaryl groups include oxazolyl, imidazolyl, pyridyl, thienyl, furyl, thiazolyl, pyrazolyl, oxadiazolyl, tetrazolyl, triazolyl.

"Heterocyclic" or "heterocycloalkyl" means a cyclic group or ring containing 2-10 carbon atoms and 1 to 4 hetero atoms selected from N, O, and S and includes groups which include one or more heteroatoms, for example, $S(=O)$, $S(=O)_2$ or NR', where R' is defined below. The cyclic group may be saturated or partially saturated. Examples of such groups include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of the monocyclic saturated or partially saturated rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like. The rings may optionally contain 1, 2 or more double bonds and in each of the above groups, the group, such as alkyl, aryl, etc., the group may be optionally substituted by 1 to 3 suitable substituents as defined below.

"Haloalkoxy" means the group haloalkyl-O—, wherein alkyl is as defined herein, including, but not limited to, fluoromethoxy, difluoromethoxy, trifluoromethoxy, 2-fluoroethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups and the like.

"Hydrocarbyl" means a monovalent radical derived from a hydrocarbon by removal of a hydrogen.

"N-Sulfonyl Carbamate" means, for example, the group $—S(=O)_2NH—COO$-Substituent, wherein the Substituent may be alkyl, cycloalkyl, cycloalkylakyl, aryl, heteroaryl as defined herein.

"Sulfonamide" means the amides of sulfonic acid.

"Sulfonamide group" means, for example, the group $—S(=O)_2NH_2$, or $—S(=O_2)NH$-Substituent, the group $—NR_6S(=O)_2—R_7$ or the group $>N—S(=O)_2—R_7$, wherein $R_7$ may be alkyl, cycloalkyl, cycloalkylakyl, aryl, heteroaryl as defined herein and $R_6$ may be H, alkyl, cycloalkyl, cycloalkylakyl, aryl, heteroaryl as defined herein.

"N-Acylsulfonamide group" means, for example, the group $—S(=O)_2NH$-Acyl wherein Acyl is as defined herein.

"Ureas" refer, for example, to compounds with the group $—N[C(=O)—NH$-Substituent]-, wherein the Substituent is as defined above in the general formulae.

"Isoureas" refer to imidic tautomers of urea $H_2NC(=NH)OH$ and its hydrocarbyl derivatives.

"N-Sulfonylureas" refer, for example, to compounds exemplified by the group $—S(=O)_2NR^cC(=O)NR^cR^d$, wherein the substituent $R^c$ and $R^d$ are as defined below.

"N-Sulfonylisoureas" refer, for example, to compounds exemplified by the group $—S(=O)_2(N=)C(OH)NR^cR^d$, wherein $R^c$ and $R^d$ are as defined below.

"Sulfamides" refer, for example, to compounds exemplified by the group $—N[S(=O)_2NHR_4]—$ wherein $R_4$ is as defined below.

"Linker" means the molecular structure between the N-terminal group (as in $X_1X_2N—$ in formula I) and the moiety Z.

"Prodrug" refers to a less active or inactive precursor of a compound or a drug, a bioreversible derivative, that is converted into its active or more active form in the mammalian body by metabolic processes. Usually, in the prodrugs described herein there is a covalent link between the drug and a chemical moiety, although prodrugs may include the drug in some salt form. For example, the N-terminal group and/or the group Z may be derivatized in a prodrug that is converted into the N-halo amino compound as described herein by metabolic processes. Examples of prodrugs with a covalent bond attached to Z are the sulfonate or phosphonate esters (such as $(C_{1-6})$alkyl esters) of the amino compounds of formulae I, IIA, III, IV, V, VI and VII. Also, for example, an N-terminal amine can be considered a prodrug that is converted to the N-halo- or N,N-dihalo-amine by myeloperoxidase-generated HOCl in vivo.

"Protecting group" means a chemical group that (a) preserves a reactive group from participating in an undesirable chemical reaction; and (b) can be selectively removed after transformation when protection of the reactive group is no longer required.

"Amino-protecting group" means a protecting group that preserves a reactive amino group that otherwise would be modified by certain chemical reactions. Non-limiting examples of amino-protecting groups include the formyl group or lower alkanoyl groups with 2 to 4 carbon atoms, in particular the acetyl or propionyl group, the trityl or substituted trityl groups, such as the monomethoxytrityl group, the 4,4'-dimethoxytrityl or 4,4'-dimethoxytriphenylmethyl group, the trifluoroacetyl, and the N-(9-fluorenyl-methoxycarbonyl) or "FMOC" group, the allyloxycarbonyl group or other protecting groups derived from halocarbonates such as $(C_{6-12})$aryl lower alkyl carbonates (such as the N-benzyloxycarbonyl group derived from benzylchlorocarbonate), such as the benzyloxycarbonyl (CBZ group), the 4-nitrobenzyloxycarbonyl group, or derived from biphenylalkyl halo carbonates, or tertiary alkyl halo carbonates, such as tertiary-butyl-halo-carbonates, in particular tertiary butyl-carbonate (BOC), or di(lower)alkyldicarbonates, in particular di-tertiary butyl-dicarbonate, and the phthalyl group. Reference is made to amine protecting groups as described in A. C. Spivey, S. J. Woodhead, "Protecting Groups", in *Annual Reports on the Progress of Chemistry*, Section B, Organic Chemistry vol. 94, Ed. J. A. Joule, RSC, Cambridge, 1998, 77-87, the entire disclosure of which is incorporated herein by reference in its entirety. Amine protecting groups are also described in T. W. Greene, P. G. M. Wuts, *Protective Groups in Organic Synthesis* (Third Edition), John Wiley & Sons, 1999, 494-654.

"Hydroxy protecting groups" means a protecting group that preserves a reactive hydroxy group that otherwise would be modified by certain chemical reactions. Non-limiting examples of hydroxy protecting groups include various ether groups, such as allyl, propargyl, p-methoxybenzyl, t-butyl-diphenylsilyl, t-butyldimethylsilyl, tetrahydropyranyl ethers, various esters such as 2-(4-methoxybenzyloxy)ethylbenzoyl, 2-(2-levulinoyloxy)ethylbenzoyl, 2-(2-levulinoyloxy)nitrobenzoyl esters, the tris(trimethylsilyl)silyl (Sisyl) group as described in the Spivey and Woodhead reference above or in the Greene reference above on pages 17-292.

"Derivative" or "derivatization" as used herein refers to a compound obtainable or derived from an N-halo- or N,N-dihaloamino compound of formulae I, II, IIA, III, IV, V, VI and VII or to a process from which such a compound can be obtained from an N-halo- or N,N-dihaloamino compound of formulae I, II, IIA, III, IV, V, VI and VII. Such a derivative may be obtainable from any functional group in the compounds of formulae I, II, IIA, III, IV, V, VI and VII. For example, such a derivative may be obtained from the following non-limiting groups described below: $X_1X_2N-$, $-SO_3H$, $-PO_3H_2$, Y, W as part of $R_1$ and $R_2$ or as part of W. The term "derivative" as used herein does not include any derivative of the compounds of formulae I, II, IIA, III, IV, V, VI and VII that are excluded by the limitations in the claims. The term "derivative" includes any derivative that substantially retains the antibacterial, antimicrobial, sporicidal, antifungal or antiviral activity of the molecule. It is recognized that this definition includes a broad class of compounds derived from the compounds of formulae I, II, IIA, III, IV, V, VI and VII, because the antibacterial, antimicrobial, spori- cidal, antifungal or antiviral activity of the molecule resides in the N-halo or N,N-dihalo group(s) present in the molecule. Any other substitutions or replacement of substituents or functional groups do not substantially affect the antibacterial, antimicrobial, sporicidal, antifungal or antiviral activity of the molecule, unless that substituent or functional group introduced by substitution or replacement eliminates the N-halo or N,N-dihalo groups present in the new derivative and as long as the molecular weight of the derivative is below 1,000, preferably below 750, most preferably below 500. A further criterion for the definition of a "derivative" of the N-halogenated compounds described and used herein is that the derivatization does not reduce the order of magnitude of the antibacterial, antimicrobial, sporicidal, antifungal or antiviral activity of the molecule by a factor 2 or more (or reduce it to 1/100 of the activity of the parent compound before its derivatization) but merely modulates the physico-chemical properties of the parent compound (for example, its m.p., crystallinity, solubility in various solvents).

As used herein, the groups alkyl, alkenyl, cycloalkyl, carbocyclyl, carbocylic, heterocyclyl, aryl, heteroaryl, etc., as defined above, may be unsubstituted or may be further substituted with 1, 2 or 3 substituents. Non-exclusive examples of such substituent include amino (R'R''N—), halo-(fluoro, chloro, bromo, iodo), trifluoromethyl, trifluoromethoxy, difluoromethoxy, hydroxyl, cyano, oxo, nitro, $(C_{1-6})$alkyl, $(C_{1-6})$alkoxy, $(C_{6-10})$aryloxy, $(C_{1-5})$alkylNHCO—, $(C_{1-5})$alkylCONH—, $(C_{1-5})$alkylCO$_2$—, $(C_{3-6})$cycloalkyl, aryl, heteroaryl, heterocycloalkyl and the like. It is understood that not all substituents are suitable for each of the above groups.

"Bioisostere" or "Isostere" means a compound or functional group resulting from the exchange of an atom or of a group of atoms with another, broadly similar, atom or group of atoms. The objective of a bioisosteric replacement is to create a new compound with similar biological and improved physio-chemical properties to the parent compound or a functional group which provides similar biological properties as the parent functional group before the exchange. In general, two isosteric groups will have the same number of valence electrons and the same electronic configuration but differing in the kinds and numbers of atoms.

Reference will now be made in detail to certain compounds and methods of use, including certain preferred compounds and preferred methods of use. The invention is not limited to those preferred compounds and methods, but rather is defined by the claim(s) issuing therefrom.

SPECIFIC EMBODIMENTS OF THE INVENTION

In its broadest aspects this disclosure comprises a compound of formula I:

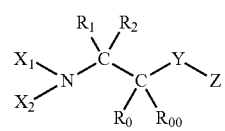

I wherein:
$X_1$ is chloro or bromo;
$X_2$ is hydrogen or is selected from the group consisting of chloro, bromo, $(C_{1-5})$alkyl, $(C_{3-6})$cycloalkyl, $(C_{3-6})$cycloalkyl, $(C_{1-3})$alkyl and halo$(C_{1-5})$alkyl;
$R_1$ and $R_2$ are each independently selected from the group consisting of $(C_{1-5})$alkyl, halo$(C_{1-5})$alkyl, $(C_{3-12})$cycloalkyl, $(C_{3-6})$cycloalkyl$(C_{1-3})$alkyl, $(C_{6-10})$aryl$(C_{1-4})$alkyl, $(C_{6-14})$aryl and heterocycloalkyl containing 2-10 carbon atoms and 1 to 4 heteroatoms selected from N, O or S, or $R_1$ and $R_2$ together with the carbon atom to which they are attached to form a $(C_{3-12})$carbocyclic or $(C_{3-12})$heterocyclyl with at least one heteroatom selected from N, O, or S in the ring;

$R_0$ and $R_{00}$ are each independently hydrogen, fluoro or the same as $R_1$ and $R_2$; or $R_1$ and $R_0$ together with the carbon atoms to which they are attached form a ring with 4 to 7 carbon ring members, wherein optionally one or two ring members are nitrogen and optionally $R_{00}$ is a double bond attached to the carbon atom to which $R_2$ is attached; or when $X_1$ is chloro or bromo, $X_2$ together with $R_0$ form an alkylenyl group with 1 to 4 carbon atoms, the alkylenyl group together with —$NX_1$— and the carbon atom having the $R_1$ and $R_2$ groups and the carbon atom having the $R_{00}$ and the —Y—Z groups form a saturated heterocyclic ring in which one or two methylene groups may be replaced with a substituted methylene group, the substituents being fluoro, chloro or $(C_{1-5})$alkyl, or replaced with —NR'— or >C=O, wherein R' has the meanings described below;

Y is a member selected from a single bond, —O—, and a divalent $(C_{1-18})$alkylenyl group in which optionally one or two methylene groups are replaced with a mono- or di-substituted methylene group, or optionally where one or two methylene groups are replaced with 1 or 2 —NR'—, —O—, —S—, —S(=O)—, >C=O, —C(=O)O—, —OC(=O)—, —C(=O)NH—, —NHC(=O)—, —C(=O)NR'—, —NR'C(=O)—, —S(=O)$_2$—, —S(=O)$_2$NR'—, —S(=O)$_2$NH—, —NR'S(=O)$_2$—, or —NHS(=O)$_2$—, where R' is hydrogen or is selected from the group consisting of Cl, Br, $(C_{1-5})$alkyl, $(C_{3-6})$cycloalkyl, $(C_{6-10})$aryl, $(C_{6-10})$aryl$(C_{1-4})$alkyl, $(C_{1-5})$alkylNHC(=O)—, $(C_{1-5})$alkoxyC(=O)—, $R^aR^bNC(=O)$—, $(C_{1-5})$alkylC(=O)—, $(C_{6-10})$arylC(=O)—, $(C_{6-10})$aryl$(C_{1-4})$alkylC(=O)—, $(C_{6-14})$aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, $(C_{1-5})$alkyl, $(C_{3-6})$cycloalkyl, $(C_{1-5})$alkylNHC(=O)—, $(C_{1-5})$alkylC(=O)—, $(C_{6-14})$aryl, $(C_{6-10})$aryl$(C_{1-4})$alkyl, heteroaryl comprising 4 to 10 ring atoms with at least one heteroatom selected from O, S and N in the ring, or heterocyclyl$(C_{1-4})$ alkyl, the heterocycloalkyl group containing 2-10 carbon atoms and 1 to 4 heteroatoms selected from N, O or S;

wherein when $R_1$ is $(C_{1-5})$alkyl or $R_1$ and $R_2$ together with the carbon atom to which they attach form a $(C_{3-6})$cycloalkyl, then $X_2$ must be $(C_{1-5})$alkyl, $(C_{3-6})$cycloalkyl, $(C_{3-6})$cycloalkyl-$(C_{1-3})$alkyl, or halo$(C_{1-5})$alkyl; or when $R_1$ is $(C_{1-5})$alkyl, then $R_2$ must be halo$(C_{1-5})$alkyl, $(C_{3-12})$cycloalkyl or $(C_{3-6})$cycloalkyl-$(C_{1-3})$ alkyl; or when $R_1$ is $(C_{1-5})$alkyl or $R_1$ and $R_2$ together with the carbon atom to which they attach form a $(C_{3-6})$cycloalkyl, then Y must be —O— or a divalent $(C_{1-18})$ alkylenyl group wherein one or two methylene groups are replaced with a substituted methylene group or by —NR'—, —O—, —S—, —S(=O)— or —S(=O)$_2$—, where R' is hydrogen or is selected from the group consisting of Cl, Br, $(C_{1-5})$alkyl, $(C_{3-6})$cycloalkyl, $(C_{6-10})$aryl, $(C_{6-10})$aryl$(C_{1-4})$alkyl, $(C_{1-5})$alkylNHC(=O)—, $(C_{1-5})$alkoxyC(=O)—, $R^aR^bNC(=O)$—, $(C_{1-5})$alkylC(=O)—, $(C_{6-10})$arylC(=O)—, $(C_{6-10})$aryl$(C_{1-4})$alkylC(=O)—, $(C_{6-14})$aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, $(C_{1-5})$alkyl, $(C_{3-6})$cycloalkyl, $(C_{1-5})$alkylNHC(=O)—, $(C_{1-5})$alkylC(=O)—, $(C_{6-14})$aryl, $(C_{6-10})$aryl$(C_{1-4})$alkyl, heteroaryl comprising 4 to 10 ring atoms with at least one heteroatom selected from O, S and N in the ring, or heterocyclyl$(C_{1-4})$ alkyl, the heterocycloalkyl group containing 2-10 carbon atoms and 1 to 4 heteroatoms selected from N, O or S;

Z is selected from the group consisting of —SO$_3$H, —PO$_3$H$_2$, a salt or ester thereof, and an acid isostere thereof but not —C(=O)OH; or is selected from the group consisting of —S(=O)$_2$NR$^c$R$^d$, —S(=O)$_2$NHC(=O)R$^e$, S(=O)$_2$C(=O)NR$^c$R$^d$, —S(=O)$_2$NR$^c$C(=O)NR$^c$R$^d$ and —S(=O)$_2$(N=)C(OH)NR$^c$R$^d$, wherein R$^c$ and R$^d$ are each independently hydrogen or is independently selected from the group consisting of $(C_{1-5})$alkyl, $(C_{3-6})$cycloalkyl, $(C_{1-5})$alkylNHC(=O)—, $(C_{1-5})$alkylC(=O)—, $(C_{6-10})$arylC(=O)—, $(C_{6-10})$aryl$(C_{1-4})$C(=O)—, $(C_{6-14})$aryl, $(C_{6-10})$aryl$(C_{1-4})$alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S, and R$^e$ is hydrogen or is selected from the group consisting of $(C_{1-5})$alkyl, $(C_{3-6})$cycloalkyl, $(C_{6-14})$aryl, $(C_{6-10})$aryl$(C_{1-4})$alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S; or a salt, an amine oxide thereof, or a derivative or a bioisostere or a prodrug thereof.

In one embodiment, $R_1$ and $R_0$ together with the carbon atoms to which they are attached form a ring system with 4 to 7 carbon ring members, wherein optionally one or two ring members are nitrogen and optionally $R_{00}$ is a double bond attached to the carbon atom to which $R_2$ is attached, wherein $X_1$, $X_2$, $R_{00}$, $R_2$, Y and Z have the meanings described above.

In another embodiment, when $X_1$ is chloro or bromo, $X_2$ together with $R_0$ form an alkylenyl group with 1 to 4 carbon atoms, the alkylenyl group together with —$NX_1$— and the carbon atom having the $R_1$ and $R_2$ groups and the carbon atom having the $R_{00}$ and the —Y—Z groups form a saturated heterocyclic ring system in which one or two methylene groups may be replaced with a substituted methylene group, the substituents being fluoro, chloro or $(C_{1-5})$alkyl, or replaced with —NR'— or >C=O, wherein $R_1$, $R_2$, Y, Z and R' have the meanings described above.

Another group of compounds includes compounds comprising the formula II:

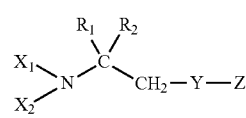

wherein:

$X_1$ is chloro or bromo;

$X_2$ is hydrogen or is selected from the group consisting of chloro, bromo, $(C_{1-5})$alkyl, $(C_{3-6})$cycloalkyl, $(C_{3-6})$cycloalkyl$(C_{1-3})$alkyl and halo$(C_{1-5})$alkyl;

$R_1$ and $R_2$ are each independently selected from the group consisting of $(C_{1-5})$alkyl, halo$(C_{1-5})$alkyl, $(C_{3-12})$cycloalkyl, $(C_{3-6})$cycloalkyl$(C_{1-3})$alkyl, $(C_{6-10})$aryl$(C_{1-4})$alkyl, $(C_{6-14})$aryl and heterocyclyl containing 2-10 carbon atoms and 1 to 4 heteroatoms selected from N, O or S, or $R_1$ and $R_2$ together with the carbon atom to which they are attached to form a ($C_{3-12}$)carbocyclic or ($C_{3-12}$)heterocyclic ring with at least one heteroatom selected from N, O, or S in the ring; or Y is a member selected from a single bond, —O—, and a divalent ($C_{1-18}$)alkylenyl group in which optionally one or two methylene groups are replaced with a mono- or di-substituted methylene group, or optionally where one or two methylene groups are replaced with 1 or 2 —NR'—, —O—, —S—, —S(=O)—, >C=O, —C(=O)O—, —OC(=O)—, —C(=O)NH—, —NHC(=O)—, —C(=O)NR'—, —NR'C(=O)—, —S(O)$_2$—, —S(=O)$_2$NR'—, —S(=O)$_2$NH—, —NR'S(=O)$_2$—, or —NHS(=O)$_2$—, where R' is hydrogen or is selected from the group consisting of Cl, Br, ($C_{1-5}$)alkyl, ($C_{3-6}$)cycloalkyl, ($C_{6-10}$)aryl, ($C_{6-10}$)aryl($C_{1-4}$)alkyl, ($C_{1-5}$)alkylNHC(=O)—, ($C_{1-5}$)alkoxyC(=O)—, $R^aR^bNC$(=O)—, ($C_{1-5}$)alkylC(=O)—, ($C_{6-10}$)arylC(=O)—, ($C_{6-10}$)aryl($C_{1-4}$)alkylC(=O)—, ($C_{6-14}$)aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, ($C_{1-5}$)alkyl, ($C_{3-6}$)cycloalkyl, ($C_{1-5}$)alkylNHC(=O)—, ($C_{1-5}$)alkylC(=O)—, ($C_{6-14}$)aryl, ($C_{6-10}$)aryl($C_{1-4}$)alkyl, heteroaryl comprising 4 to 10 ring atoms with at least one heteroatom selected from O, S and N in the ring, or heterocyclyl($C_{1-4}$) alkyl, the heterocycloalkyl group containing 2-10 carbon atoms and 1 to 4 heteroatoms selected from N, O or S;

wherein when $R_1$ is ($C_{1-5}$)alkyl or $R_1$ and $R_2$ together with the carbon atom to which they attach form a ($C_{3-6}$)cycloalkyl, then $X_2$ must be ($C_{1-5}$)alkyl, ($C_{3-6}$)cycloalkyl, ($C_{3-6}$)cycloalkyl-($C_{1-3}$)alkyl, or halo($C_{1-5}$)alkyl; or when $R_1$ is ($C_{1-5}$)alkyl, then $R_2$ must be halo($C_{1-5}$)alkyl, ($C_{3-12}$)cycloalkyl or ($C_{3-6}$)cycloalkyl-($C_{1-3}$) alkyl; or when $R_1$ is ($C_{1-5}$)alkyl or $R_1$ and $R_2$ together with the carbon atom to which they attach form a ($C_{3-6}$)cycloalkyl, then Y must be —O— or a divalent ($C_{1-18}$) alkylenyl group wherein one or two methylene groups are replaced with a substituted methylene group or by —NR'—, —O—, >C=O, —C(=O)O—, —OC(=O)—, —NHC(=O)—, —C(=O)NR'—, —NR'C(=O)—, —S—, —S(=O)—, —S(=O)$_2$—, —S(=O)$_2$NR'—, —S(=O)$_2$NH—, —NR'S(=O)$_2$—, or —NHS(=O)$_2$—, where R' is hydrogen or is selected from the group consisting of Cl, Br, ($C_{1-5}$)alkyl, ($C_{3-6}$)cycloalkyl, ($C_{6-10}$)aryl, ($C_{6-10}$)aryl($C_{1-4}$)alkyl, ($C_{1-5}$)alkylNHC(=O)—, ($C_{1-5}$)alkoxyC(=O)—, $R^aR^bNC$(=O)—, ($C_{1-5}$)alkylC(=O)—, ($C_{6-10}$)arylC(=O)—, ($C_{6-10}$)aryl($C_{1-4}$)alkylC(=O)—, ($C_{6-14}$)aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, ($C_{1-5}$)alkyl, ($C_{3-6}$)cycloalkyl, ($C_{1-5}$)alkylNHC(=O)—, ($C_{1-5}$)alkylC(=O)—, ($C_{6-14}$)aryl, ($C_{6-10}$)aryl($C_{1-4}$)alkyl, heteroaryl comprising 4 to 10 ring atoms with at least one heteroatom selected from O, S and N in the ring, or heterocyclyl($C_{1-4}$) alkyl, the heterocycloalkyl group containing 2-10 carbon atoms and 1 to 4 heteroatoms selected from N, O or S;

Z is selected from the group consisting of —SO$_3$H, —PO$_3$H$_2$, a salt or ester thereof, and an acid isostere thereof but not —C(=O)OH; or is selected from the group consisting of —S(=O)$_2$NR$^c$R$^d$, —S(=O)$_2$NHC(=O)R$^e$, S(=O)$_2$C(=O)NR$^c$R$^d$, —S(=O)$_2$NR$^c$C(=O)NR$^c$R$^d$ and —S(=O)$_2$(N=)C(OH)NR$^c$R$^d$, wherein R$^c$ and R$^d$ are each independently hydrogen or is independently selected from the group consisting of ($C_{1-5}$)alkyl, ($C_{3-6}$)cycloalkyl, ($C_{1-5}$)alkylNHC(=O)—, ($C_{1-5}$)alkylC(=O)—, ($C_{6-10}$)arylC(=O)—, ($C_{6-10}$)aryl($C_{1-4}$)C(=O)—, aryl containing 6 to 14 ring atoms, ($C_{6-10}$)aryl($C_{1-4}$)alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S, and R$^e$ is hydrogen or is selected from the group consisting of ($C_{1-5}$)alkyl, ($C_{3-6}$)cycloalkyl, ($C_{6-14}$)aryl, ($C_{6-10}$)aryl($C_{1-4}$) alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S; or a salt, an amine oxide thereof, or a derivative or a bioisostere or a prodrug thereof.

In certain compounds of formula II, $R_1$ and $R_2$ together with the carbon atom to which they are attached to form a ($C_{4-7}$)carbocyclic or ($C_{3-6}$)heterocyclic ring.

In certain compounds of formula II, $R_1$ and $R_2$ are each independently halo($C_{1-5}$)alkyl or a 5-12 member heterocyclyl comprising 1 to 4 members selected from —NR'—, —O—, —S—, where R' is hydrogen or is selected from the group consisting of ($C_{1-5}$)alkyl, ($C_{3-6}$)cycloalkyl, ($C_{1-5}$)alkylNHC(=O)—, ($C_{1-5}$)alkoxyC(=O)—, ($C_{1-5}$)alkylC(=O)—, ($C_{6-10}$)arylC(=O)—, ($C_{6-10}$)aryl($C_{1-4}$)alkylC(=O)—, ($C_{6-14}$)aryl, ($C_{6-10}$)aryl($C_{1-4}$)alkyl, heteroaryl comprising 4 to 10 ring atoms with at least one heteroatom selected from O, S and N in the ring and heterocyclyl containing 2-10 carbon atoms and 1 to 4 heteroatoms selected from N, O or S; Y is a divalent ($C_{1-18}$)alkylenyl group; and Z is selected from the group consisting of —SO$_3$H, —PO$_3$H$_2$, —S(=O)$_2$NR$^c$R$^d$, —S(=O)$_2$NHC(=O)R$^e$, —S(=O)$_2$OC(=O)NR$^c$R$^d$, —S(=O)$_2$NR$^c$C(=O)NR$^c$R$^d$ and —S(O)$_2$(N=)C(OH)NR$^c$R$^d$, wherein R$^c$ and R$^d$ are each independently hydrogen, or are independently selected from the group consisting of ($C_{1-5}$)alkyl, ($C_{1-5}$)alkylNHC(=O)—, ($C_{1-5}$)alkylC(=O)—, ($C_{3-6}$)cycloalkyl, aryl containing 6 to 14 ring atoms, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, and R$^e$ is hydrogen or is selected from the group consisting of ($C_{1-5}$)alkyl, ($C_{3-6}$)cycloalkyl, ($C_{6-14}$)aryl, ($C_{6-10}$)aryl($C_{1-4}$)alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S; or a salt thereof.

In certain compounds of formula II, $X_1$ and $X_2$ are each independently chloro or bromo, or $X_1$ is chloro or bromo and $X_2$ is hydrogen or is selected from the group consisting of ($C_{1-5}$)alkyl, ($C_{3-6}$)cycloalkyl, ($C_{3-6}$)cycloalkyl($C_{1-3}$)alkyl and halo($C_{1-5}$)alkyl; $R_1$ and $R_2$ together with the carbon atom to which they are attached to form a ($C_{3-7}$)heterocyclic ring comprising the heteroatoms selected from the group consisting of N, O and S; Y is a bond or a divalent ($C_{1-6}$)alkylenyl group; and Z is —SO$_3$H or —PO$_3$H$_2$; or a salt thereof.

In certain compounds of formula II, $R_1$ is halo($C_{1-5}$)alkyl, and $R_2$ is halo ($C_{1-5}$)alkyl. In a subgroup of these compounds Z is —S(=O)$_2$NR$^c$R$^d$, wherein R$^c$ and R$^d$ are each independently hydrogen or are independently selected from the group consisting of ($C_{1-5}$)alkyl, ($C_{3-6}$)cycloalkyl, ($C_{1-5}$)alkylNHC(=O)—, ($C_{1-5}$)alkylC(=O)—, aryl containing 6 to 14 ring atoms, heteroaryl comprising 4 to 10 ring atoms with at least one heteroatom selected from O, S and N in the ring, and heterocyclyl containing 2-10 carbon atoms and 1 to 4 heteroatoms selected from N, O or S; or a salt thereof.

In certain compounds of formula II, $X_1$ and $X_2$ are both chloro; and Z is —SO$_3$H or —S(=O)$_2$NR$^c$R$^d$, wherein R$^c$ and R$^d$ are each independently hydrogen or are independently selected from the group consisting of $(C_{1-5})$alkyl, $(C_{3-6})$cycloalkyl, $(C_{1-5})$alkylNHC(=O)—, $(C_{1-5})$alkylC(=O)—, aryl containing 6 to 14 ring atoms, heteroaryl comprising 4 to 10 ring atoms with at least one heteroatom selected from O, S and N in the ring, and heterocyclyl containing 2-10 carbon atoms and 1 to 4 heteroatoms selected from N, O or S; or a salt thereof.

In certain compounds of formula II, $R_1$ and $R_2$ together with the carbon atom to which they are attached form a $(C_{4-7})$carbocyclic or $(C_{4-7})$heterocyclic ring containing from 1 to 4 hetero atoms selected from the group consisting of N, O and S; said ring being interrupted by a member selected from the group consisting of —O—, —S(=O)$_2$—, —NR$_3$—, —CR$_3$R$_3$—, >C=CR$_3$R$_3$, —N[C(=O)NHR$_4$]—, —N[S(=O)$_2$R$_4$]—, —N[S(=O)$_2$NHR$_4$]—, —N[C(=O)R$_5$]— and —N[C(=O)OR$_5$]—;

$R_3$ each independently selected from the group consisting of hydrogen, $(C_{1-5})$alkyl, $(C_{3-7})$cycloalkyl, $(C_{3-6})$cycloalkyl-$(C_{1-3})$alkyl, $(C_{5-6})$carbocyclyl where 1, 2 or 3 carbon ring members are optionally replaced by —NR'—, —O—, —S—, —S(=O)— or —S(=O)$_2$—, where R' is hydrogen or is selected from the group consisting of $(C_{1-5})$alkyl, $(C_{1-5})$alkylNHC(=O)—, $(C_{1-5})$alkylC(=O)—, $(C_{3-6})$cycloalkyl, heterocycloalkyl containing 2-10 carbon atoms and 1 to 4 heteroatoms selected from N, O or S, $(C_{6-12})$aryl, $(C_{6-12})$heteroaryl, $(C_{1-4})$alkyl$(C_{6-10})$aryl, $(C_{6-10})$aryl$(C_{1-4})$alkyl, $(C_{1-5})$alkylC(=O)—, $(C_{6-10})$arylC(=O)—, $(C_{6-10})$aryl$(C_{1-4})$alkylC(=O)—, $(C_{1-5})$alkoxyC(=O)— and —S(=O)$_2$NH$(C_{1-5})$alkyl; $R_4$ is selected from the group consisting of $(C_{1-5})$alkyl, $(C_{3-7})$cycloalkyl, $(C_{3-6})$cycloalkyl-$(C_{1-3})$alkyl, $(C_{6-12})$aryl and $(C_{5-6})$carbocyclyl where 1, 2 or 3 carbon ring members are replaced by —NR'—, —O—, —S—, —S(=O)— or —S(=O)$_2$—, where R' is hydrogen or is selected from the group consisting of $(C_{1-5})$alkyl, $(C_{1-5})$alkylNHC(=O)—, $(C_{1-5})$alkylC(=O)NH—, $(C_{1-5})$alkylC(=O)—, $(C_{3-6})$cycloalkyl, heterocycloalkyl containing 2-10 carbon atoms and 1 to 4 heteroatoms selected from N, O or S, $(C_{6-12})$aryl, $(C_{6-10})$aryl$(C_{1-4})$alkyl, $(C_{6-12})$heteroaryl, $(C_{1-6})$alkyl$(C_{6-12})$aryl, $(C_{6-12})$aryl$(C_{1-6})$alkyl, $(C_{1-5})$alkylC(=O)—, $(C_{1-5})$alkoxyC(=O)— and —S(=O)$_2$NH$(C_{1-5})$alkyl;

$R_5$ is selected from the group consisting of $(C_{1-5})$alkyl, $(C_{1-5})$alkoxy, $(C_{3-7})$cycloalkyl, $(C_{3-6})$cycloalkyl-$(C_{1-3})$alkyl, $(C_{6-10})$aryl, $(C_{6-10})$aryloxy, $(C_{7-12})$arylalkyl, $(C_{7-12})$alkylaryl and $(C_{7-12})$arylalkoxy; Y is a single bond or a divalent $(C_{1-6})$ alkylene group; and Z is —SO$_3$H or —PO$_3$H$_2$; or a salt thereof.

In other compounds of formula II, $R_1$ and $R_2$ independently are $(C_{1-5})$alkyl or halo$(C_{1-5})$alkyl with 1-5, preferably 1-3 halogen atoms selected from the group of fluoro and chloro; or a salt thereof.

In further compounds of formula II, Y is a single bond; or a salt thereof.

In further compounds of formula II, Y is a $(C_{1-12})$alkylenyl, preferably a $(C_{1-6})$ alkylenyl group; or a salt thereof.

In further compounds of formula II, $X_1$ and $X_2$ are chloro; or a salt thereof. In further compounds of formula II $R_1$ and $R_2$ are both methyl; $X_1$ is chloro or bromo; and $X_2$ is $(C_{1-2})$alkyl or halo$(C_{1-2})$alkyl; or a salt thereof. In preferred compounds of this subgroup $X_1$ is chloro; Y is a single bond; or a salt thereof.

In further compounds of formula II, $X_1$ and $X_2$ are both chloro; $R_1$ and $R_2$ are each independently halo$(C_{1-2})$alkyl, $(C_{3-12})$cycloalkyl, $(C_{4-12})$aryl, $(C_{6-10})$aryl$(C_{1-2})$alkyl or $(C_{3-12})$heterocyclyl comprising 1-4 heteroatoms selected from the group consisting of O, N or S; Y is a single bond; Z is selected from the group consisting of —SO$_3$H and —S(=O)$_2$NR$^c$R$^d$ wherein R$^c$ and R$^d$ are each independently hydrogen or selected from the group consisting of $(C_{1-5})$alkyl, $(C_{1-5})$alkylNHC(=O)—, $(C_{1-5})$alkylC(=O)—, $(C_{3-6})$cycloalkyl, aryl containing 6 to 12 ring atoms, $(C_{6-10})$aryl$(C_{1-2})$alkyl, heteroaryl comprising 4 to 10 ring atoms with at least one heteroatom selected from O, S and N in the ring and heterocycloalkyl containing 2-10 carbon atoms and 1 to 4 heteroatoms selected from N, O or S; or a salt thereof.

In further compounds of formula II, $X_1$ and $X_2$ are both chloro; and $R_1$ and $R_2$ together with the carbon atom to which they are attached to form a $(C_{4-7})$heterocycloalkyl comprising the group —O—, —S—, —SO—, —SO$_2$— or —NR$_3$—, where $R_3$ is $(C_{1-5})$alkyl or $(C_{1-5})$alkylC(=O)—, $(C_{6-10})$arylC(=O)—, $(C_{6-10})$aryl$(C_{1-4})$alkylC(=O)—; Y is a single bond; and Z is selected from the group consisting of —SO$_3$H and —S(=O)$_2$NR$^c$R$^d$ wherein R$^c$ and R$^d$ are each independently hydrogen or selected from the group consisting of $(C_{1-5})$ alkyl, $(C_{1-5})$alkylNHC(=O)—, $(C_{1-5})$alkylC(=O)—, $(C_{6-10})$arylC(=O)—, $(C_{6-10})$aryl$(C_{1-4})$alkylC(=O)—, $(C_{3-6})$cycloalkyl, $(C_{6-14})$aryl, $(C_{6-10})$aryl$(C_{1-2})$alkyl, heteroaryl comprising 4 to 10 ring atoms with at least one heteroatom selected from O, S and N in the ring and heterocycloalkyl containing 2-10 carbon atoms and 1 to 4 heteroatoms selected from N, O or S; or a salt thereof.

In further compounds of formula II Z is —SO$_3$H; or a salt thereof. In a subgroup of these compounds $X_1$ is chloro, $X_2$ is methyl or trifluoromethyl; or a salt thereof. In another subgroup of these compounds $R_1$ and $R_2$ independently are $(C_{1-5})$alkyl, halo$(C_{1-5})$alkyl, preferably —CF$_3$; or a salt thereof.

In further compounds of formula II, Y is a divalent $(C_{1-4})$ alkylenyl group optionally replaced by a —NR'—, —O—, —S—, —S(=O)—, >C=O, or —S(=O)$_2$— group or a salt thereof.

Another group of compounds includes compounds comprising the formula IIA:

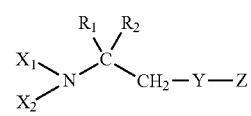

IIA wherein:

$X_1$ is chloro;

$X_2$ is hydrogen or is selected from the group consisting of chloro, $(C_{1-5})$alkyl, $(C_{3-6})$cycloalkyl, and $(C_{3-6})$cycloalkyl$C_{1-3}$ alkyl;

$R_1$ and $R_2$ are each independently selected from the group consisting of $(C_{1-5})$alkyl, halo$(C_{1-5})$alkyl, $(C_{3-12})$cycloalkyl, $(C_{3-6})$cycloalkyl$(C_{1-3})$alkyl, $(C_{6-10})$aryl$(C_{1-4})$alkyl, $(C_{6-14})$ aryl and heterocyclyl containing 2-10 carbon atoms and 1 to 4 heteroatoms selected from N, O or S, or $R_1$ and $R_2$ together with the carbon atom to which they are attached to form a $(C_{6-12})$ carbocyclic or $(C_{3-12})$heterocyclic ring with at least one heteroatom selected from N, O, or S in the ring; or Y is a member selected from a single bond, —O—, and a divalent $(C_{1-18})$alkylenyl group in which optionally one or two methylene groups are replaced with a mono- or di-substituted methylene group, or optionally where one or two methylene groups are replaced with 1 or 2 —NR'—, —O—, —S—, —S(=O)—, >C=O, —C(=O)O—, —OC(=O)—, —C(=O)NH—, —NHC(=O)—, —C(=O)NR'—, —NR'C(=O)—, or —S(=O)$_2$—, where R' is hydrogen or is selected from the group consisting of $(C_{1-5})$alkyl, $(C_{3-6})$cycloalkyl, $(C_{6-10})$aryl, and $(C_{6-10})$aryl$(C_{1-4})$alkyl;

wherein when R$_1$ is (C$_{1-5}$)alkyl or R$_1$ and R$_2$ together with the carbon atom to which they attach form a (C$_{7-12}$) cycloalkyl, then X$_2$ must be (C$_{1-5}$)alkyl, (C$_{1-5}$)haloalkyl (C$_{3-6}$)cycloalkyl, (C$_{3-6}$)cycloalkyl-(C$_{1-3}$)alkyl; or when R$_1$ is (C$_{1-5}$)alkyl, then R$_2$ must be (C$_{3-12}$)cycloalkyl or (C$_{3-6}$)cycloalkyl-(C$_{1-3}$) alkyl; or when R$_1$ is (C$_{1-5}$)alkyl or R$_1$ and R$_2$ together with the carbon atom to which they attach form a (C$_{7-12}$)cycloalkyl, then Y must be —O— or a divalent (C$_{1-18}$) alkylenyl group wherein one or two methylene groups are replaced with a substituted methylene group or by —NR'—, —O—, >C=O, —C(=O)O—, —OC(=O)—, —C(=O)NH—, —NHC(=O)—, —C(=O)NR'—, —NR'C(=O)—, —S—, —S(=O)— or —S(=O)$_2$—, where R' is hydrogen or is selected from the group consisting of (C$_{1-5}$)alkyl, (C$_{3-6}$)cycloalkyl, (C$_{6-10}$)aryl, and (C$_{6-10}$)aryl(C$_{1-4}$)alkyl;

Z is selected from the group consisting of —SO$_3$H, —PO$_3$H$_2$, a salt or ester thereof, and an acid isostere thereof but not —C(=O)OH; or is selected from the group consisting of —S(=O)$_2$NR$^c$R$^d$, —S(=O)$_2$NHC(=O)R$^e$, S(=O)$_2$OC(=O)NR$^c$R$^d$, —S(=O)$_2$NR$^c$C(=O)NR$^c$R$^d$ and —S(=O)$_2$(N=C(OH)NR$^c$R$^d$, wherein R$^c$ and R$^d$ are each independently hydrogen or is independently selected from the group consisting of (C$_{1-5}$)alkyl, (C$_{3-6}$)cycloalkyl, (C$_{1-5}$)alkylNHC(=O)—, (C$_{1-5}$)alkylC(=O)—, (C$_{6-10}$)arylC(=O)—, (C$_{6-10}$)aryl(C$_{1-4}$)C(=O)—, aryl containing 6 to 14 ring atoms, (C$_{6-10}$)aryl(C$_{1-4}$)alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S, and R$^e$ is hydrogen or is selected from the group consisting of (C$_{1-5}$)alkyl, (C$_{3-6}$)cycloalkyl, (C$_{6-14}$)aryl, (C$_{6-10}$)aryl(C$_{1-4}$) alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S; or a salt, an amine oxide thereof, or a derivative or a bioisostere or a prodrug thereof.

In certain compounds of formula IIA, R$_1$ and R$_2$ together with the carbon atom to which they are attached to form a (C$_{7-12}$)carbocyclic or (C$_{3-6}$)heterocyclic ring.

In certain compounds of formula IIA, X$_1$ is chloro and X$_2$ is hydrogen or is selected from the group consisting of chloro, (C$_{1-5}$)alkyl, (C$_{3-6}$)cycloalkyl, (C$_{3-6}$)cycloalkyl(C$_{1-3}$)alkyl; R$_1$ and R$_2$ together with the carbon atom to which they are attached to form a (C$_{3-7}$)heterocyclic ring comprising the heteroatoms selected from the group consisting of N, O and S; Y is a bond or a divalent (C$_{1-6}$)alkylenyl group; and Z is —SO$_3$H or —PO$_3$H$_2$; or a salt thereof.

In certain compounds of formula IIA, X$_1$ and X$_2$ are both chloro; and Z is —SO$_3$H or —S(=O)$_2$NR$^c$R$^d$, wherein R$^c$ and R$^d$ are each independently hydrogen or are independently selected from the group consisting of (C$_{1-5}$)alkyl, (C$_{3-6}$)cycloalkyl, (C$_{1-5}$)alkylNHC(=O)—, (C$_{1-5}$)alkylC(=O)—, aryl containing 6 to 14 ring atoms, heteroaryl comprising 4 to 10 ring atoms with at least one heteroatom selected from O, S and N in the ring, and heterocyclyl containing 2-10 carbon atoms and 1 to 4 heteroatoms selected from N, O or S; or a salt thereof.

In further compounds of formula IIA, Y is a single bond; or a salt thereof.

In further compounds of formula IIA, Y is a (C$_{1-12}$)alkylenyl, preferably a (C$_{1-6}$)alkylenyl group; or a salt thereof.

In further compounds of formula IIA, X$_1$ and X$_2$ are chloro; or a salt thereof. In further compounds of formula IIA, R$_1$ and R$_2$ are both methyl; X$_1$ is chloro or bromo; and X$_2$ is hydrogen, (C$_{1-2}$)alkyl or halo(C$_{1-2}$)alkyl; or a salt thereof. In preferred compounds of this subgroup X$_1$ is chloro; Y is a single bond; or a salt thereof.

In further compounds of formula IIA, X$_1$ and X$_2$ are both chloro; R$_1$ and R$_2$ are each independently (C$_{3-12}$)cycloalkyl, (C$_{4-12}$)aryl, (C$_{6-10}$)aryl(C$_{1-2}$)alkyl or (C$_{3-12}$)heterocyclyl comprising 1-4 heteroatoms selected from the group consisting of O, N or S; Y is a single bond; Z is selected from the group consisting of —SO$_3$H and —S(=O)$_2$NR$^c$R$^d$ wherein R$^c$ and R$^d$ are each independently hydrogen or selected from the group consisting of (C$_{1-5}$)alkyl, (C$_{1-5}$)alkylNHC(=O)—, (C$_{1-5}$)alkylC(=O)—, (C$_{3-6}$)cycloalkyl, aryl containing 6 to 12 ring atoms, (C$_{6-10}$)aryl(C$_{1-2}$)alkyl, heteroaryl comprising 4 to 10 ring atoms with at least one heteroatom selected from O, S and N in the ring and heterocycloalkyl containing 2-10 carbon atoms and 1 to 4 heteroatoms selected from N, O or S; or a salt thereof.

In further compounds of formula IIA, Z is —SO$_3$H; or a salt thereof. In a subgroup of these compounds X$_1$ is chloro, X$_2$ is (C$_{1-5}$)alkyl; or a salt thereof. In another subgroup of these compounds R$_1$ and R$_2$ independently are (C$_{1-5}$)alkyl or a salt thereof.

Certain compounds comprise formula III:

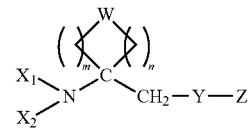

wherein:

m and n are each independently an integer of 0, 1, 2, 3, 4 or 5, and m and n together is 2, 3, 4 or 5;

W is selected from the group consisting of —O—, —S—, —S(=O)—, —S(=O)$_2$—, —NR$_3$—, —CR$_3$R$_3$—, >C=CR$_3$R$_3$, —N[C(=O)NHR$_4$]—, —N[S(=O)$_2$R$_4$]—, —N[S(=O)$_2$NHR$_4$]—, —N[C(=O)R$_5$]—, —NR$_4$C(=O)—, >C=O, and —N[C(=O)OR$_5$]—;

Y is a member selected from a single bond, —O—, and a divalent (C$_{1-18}$)alkylenyl group in which optionally one or two methylene groups are replaced with a mono- or di-substituted methylene group, or optionally where one or two methylene groups are replaced with 1 or 2-NR'—, —O—, —S—, —S(=O)—, >C=O, —C(=O)O—, —OC(=O)—, —C(=O)NH—, —NHC(=O)—, —C(=O)NR'—, —NR'C(=O)—, —S(=O)$_2$NR'—, —S(=O)$_2$NH—, —NR'S(=O)$_2$—, or —NHS(=O)$_2$—, where R' is hydrogen or is selected from the group consisting of Cl, Br, (C$_{1-5}$)alkyl, (C$_{3-6}$)cycloalkyl, (C$_{6-10}$)aryl, (C$_{6-10}$)aryl(C$_{1-4}$)alkyl, (C$_{1-5}$)alkylNHC(=O)—, (C$_{1-5}$)alkoxyC(=O)—, R$^a$R$^b$NC(=O)—, (C$_{1-5}$)alkylC(=O)—, (C$_{6-10}$)arylC(=O)—, (C$_{6-10}$)aryl(C$_{1-4}$)alkylC(=O)—, (C$_{6-14}$)aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein R$^a$ and R$^b$ are each independently hydrogen, (C$_{1-5}$)alkyl, (C$_{3-6}$)cycloalkyl, (C$_{1-5}$)alkylNHC(=O)—, (C$_{1-5}$)alkylC(=O)—, (C$_{6-14}$)aryl, (C$_{6-10}$)aryl(C$_{1-4}$)alkyl, heteroaryl comprising 4 to 10 ring atoms with at least one heteroatom selected from O, S and N in the ring, or heterocyclyl(C$_{1-4}$) alkyl, the heterocycloalkyl group containing 2-10 carbon atoms and 1 to 4 heteroatoms selected from N, O or S;

Z is selected from the group consisting of —SO$_3$H, —PO$_3$H$_2$, —S(=O)$_2$NR$^c$R$^d$, —S(=O)$_2$NHC(=O)R$^e$, —S(=O)$_2$NR$^c$C(=O)NR$^c$R$^d$, —S(=O)$_2$C(=O)NR$^c$R$^d$ and —S(=O)$_2$(N=)C(OH)NR$^c$R$^d$, wherein R$^c$ and R$^d$ are each independently hydrogen or are selected from the group consisting of (C$_{1-5}$)alkyl, (C$_{1-5}$)alkylNHC(=O)—, (C$_{1-5}$)alkylC(=O)—, (C$_{3-6}$)cycloalkyl, aryl containing 6 to 14 ring atoms, (C$_{6-10}$)aryl(C$_{1-4}$)alkyl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, and R$^e$ is hydrogen or is selected from the group consisting of (C$_{1-5}$)alkyl, (C$_{3-6}$)cycloalkyl, (C$_{6-14}$)aryl, (C$_{6-10}$)aryl(C$_{1-4}$)alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S;

X$_1$ is chloro or bromo;

X$_2$ is hydrogen or is selected from the group consisting of chloro, bromo, (C$_{1-5}$)alkyl, (C$_{3-6}$)cycloalkyl, (C$_{3-6}$)cycloalkyl(C$_{1-3}$)alkyl and halo(C$_{1-5}$)alkyl;

R$_3$ is each independently selected from the group consisting of hydrogen, (C$_{1-5}$)alkyl, (C$_{3-7}$)cycloalkyl, (C$_{3-6}$)cycloalkyl-(C$_{1-3}$)alkyl, (C$_{5-6}$)carbocyclyl where 1, 2 or 3 carbon ring members are optionally replaced by —NR'—, —O—, —S—, —S(=O)— or —S(=O)$_2$—, where R' is hydrogen or is selected from the group consisting of Cl, Br, (C$_{1-5}$)alkyl, (C$_{3-6}$)cycloalkyl, (C$_{6-10}$) aryl, (C$_{6-10}$)aryl(C$_{1-4}$)alkyl, (C$_{1-5}$)alkylNHC(=O)—, (C$_{1-5}$)alkoxyC(=O)—, R$^a$R$^b$NC(=O)—, (C$_{1-5}$)alkylC(=O)—, (C$_{6-10}$)arylC(=O)—, (C$_{6-10}$)aryl(C$_{1-4}$)alkylC(=O)—, (C$_{6-14}$)aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein R$^a$ and R$^b$ are each independently hydrogen, (C$_{1-5}$)alkyl, (C$_{3-6}$)cycloalkyl, (C$_{1-5}$)alkylNHC(=O)—, (C$_{1-5}$)alkylC(=O)—, (C$_{6-14}$)aryl, (C$_{6-10}$)aryl(C$_{1-4}$)alkyl, heteroaryl comprising 4 to 10 ring atoms with at least one heteroatom selected from O, S and N in the ring, or heterocyclyl(C$_{1-4}$) alkyl, the heterocycloalkyl group containing 2-10 carbon atoms and 1 to 4 heteroatoms selected from N, O or S;

R$_4$ is selected from the group consisting of (C$_{1-5}$)alkyl, (C$_{3-7}$)cycloalkyl, (C$_{3-6}$)cycloalkyl-(C$_{1-3}$)alkyl, (C$_{6-12}$)aryl and (C$_{5-6}$)carbocycloalkyl where 1, 2, or 3 carbon ring members are replaced by —NR'—, —O—, —S—, —S(=O)— or —S(=O)$_2$—, where R' is hydrogen or is selected from the group consisting of (C$_{1-5}$)alkyl, (C$_{1-5}$)alkylNHC(=O)—, (C$_{1-5}$)alkylC(=O)—, (C$_{3-6}$)cycloalkyl, heterocycloalkyl containing 2-10 carbon atoms and 1 to 4 heteroatoms selected from N, O or S, (C$_{6-12}$)aryl, (C$_{6-10}$)aryl(C$_{1-4}$)alkyl, (C$_{6-12}$) heteroaryl, (C$_{1-6}$)alkylaryl, (C$_{6-12}$)aryl(C$_{1-6}$)alkyl, (C$_{1-5}$)alkylC(=O)—, (C$_{1-5}$)alkoxyC(=O)— and —S(=O)$_2$NH(C$_{1-5}$)alkyl;

R$_5$ is selected from the group consisting of (C$_{1-5}$)alkyl, (C$_{1-5}$)alkoxy, (C$_{3-7}$)cycloalkyl, (C$_{3-6}$)cycloalkyl-(C$_{1-3}$)alkyl, (C$_{6-10}$)aryl, (C$_{6-10}$)aryloxy, (C$_{7-12}$)arylalkyl, (C$_{7-12}$)alkylaryl and (C$_{7-12}$)arylalkoxy;

and wherein W is a group other than —CH$_2$—, then X$_1$ and X$_2$ are as defined above;

and when W is the group —CH$_2$—, then X$_2$ is not hydrogen, chloro or bromo;

or optionally when W is a tertiary amine, or when —NR'— is a tertiary amine or an amine-oxide thereof; or a salt or derivative or bioisostere or prodrug thereof.

In certain compounds of formula III W is selected from the group consisting of =O—, —S(=O)$_2$—, —NR$_3$—, —CR$_3$R$_3$—, >C=CR$_3$R$_3$, —N[C(=O)NHR$_4$]—, —N[S(=O)$_2$R$_4$]—, —N[S(=O)$_2$NHR$_4$]—, —N[C(=O)R$_5$]— and —N[C(=O)OR$_5$]—; R$_3$, R$_4$ and R$_5$ are as defined above; Y is a single bond or a divalent (C$_{1-5}$)alkylenyl group; and Z is —SO$_3$H or —PO$_3$H$_2$; or a salt thereof.

A further aspect comprises compounds of formula IV:

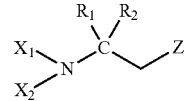

wherein:

R$_1$ is selected from the group consisting of (C$_{1-5}$)alkyl optionally substituted with 1 to 5 halogen atoms, (C$_{6-10}$)aryl and (C$_{6-10}$)aryl(C$_{1-4}$)alkyl;

R$_2$ is selected from the group consisting of (C$_{1-5}$) alkyl optionally substituted with 1 to 5 halogen atoms, (C$_{6-10}$)aryl and (C$_{6-10}$)aryl(C$_{1-4}$)alkyl;

X$_1$ is chloro or bromo;

X$_2$ is hydrogen or is selected from the group consisting of chloro, bromo, (C$_{1-5}$)alkyl, (C$_{3-6}$)cycloalkyl, (C$_{3-6}$)cycloalkyl(C$_{1-3}$)alkyl and halo(C$_{1-5}$)alkyl; and Z is selected from the group consisting of —SO$_3$H and —S(=O)$_2$NR$^c$R$^d$ wherein R$^c$ and R$^d$ are each independently hydrogen or selected from the group consisting of (C$_{1-5}$) alkyl, (C$_{1-5}$)alkylNHC(=O)—, (C$_{1-5}$)alkylC(=O)—, (C$_{3-6}$) cycloalkyl, (C$_{6-14}$)aryl, (C$_{6-10}$)aryl(C$_{1-4}$)alkyl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S in the ring; or a salt thereof.

In certain compounds of formula IV X$_1$ and X$_2$ are both chloro; or a salt thereof.

In certain compounds of formula IV R$_1$ is methyl; R$_2$ is CF$_3$; or a salt thereof. In a subgroup of these certain compounds X$_1$ and X$_2$ are both chloro; or a salt thereof. In other compounds of formula IV R$_1$ and R$_2$ are both —CF$_3$; X$_1$ and X$_2$ are both chloro, or X$_1$ is chloro and X$_2$ is (C$_{1-2}$)alkyl or halo(C$_{1-2}$)alkyl; or a salt or derivative or bioisostere or prodrug thereof.

A further group of compounds comprises compounds of formula V:

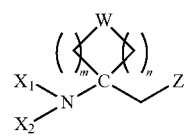

wherein:

m and n are each an integer of 0, 1, 2, 3, 4 or 5, and m and n together is 2, 3, 4 or 5;

W is selected from the group consisting of —O—, —S—, —S(=O)—, —NR$_3$—, —CR$_3$R$_3$—, >C=CR$_3$R$_3$, —N[C(=O)NHR$_4$]—, —N[S(=O)$_2$R$_4$]—, —N[S(=O)$_2$NHR$_4$]—, >C=O, and —N[C(=O)R$_5$]—;

Z is selected from the group consisting of —SO$_3$H, —PO$_3$H$_2$, —S(=O)$_2$NR$^c$R$^d$, —S(=O)$_2$NHC(=O)R$^e$, —S(=O)$_2$NR$^c$C(=O) NR$^c$R$^d$, —S(=O)$_2$C(=O)NR$^c$R$^d$ and —S(=O)$_2$(N=)C(OH)NR$^c$R$^d$, wherein R$^c$ and R$^d$ are each independently hydrogen or are each independently selected from the group consisting of $(C_{1-5})$alkyl, $(C_{1-5})$alkylNHC(=O)—, $(C_{1-5})$alkylC(=O)—, $(C_{3-6})$cycloalkyl, $(C_{6-14})$aryl, $(C_{6-10})$aryl$(C_{1-2})$alkyl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, and $R^e$ is hydrogen or is selected from the group consisting of $(C_{1-5})$alkyl, $(C_{3-6})$cycloalkyl, $(C_{6-14})$aryl, $(C_{6-10})$aryl$(C_{1-2})$alkyl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S;

$X_1$ is chloro or bromo;

$X_2$ is hydrogen or is selected from the group consisting of chloro, bromo, $(C_{1-5})$alkyl, $(C_{3-6})$cycloalkyl, $(C_{3-6})$cycloalkyl$(C_{1-3})$alkyl and halo$(C_{1-5})$alkyl;

$R_3$ is each independently selected from the group consisting of hydrogen, $(C_{1-5})$alkyl, $(C_{3-7})$cycloalkyl, $(C_{3-6})$cycloalkyl$(C_{1-3})$alkyl, $(C_{5-6})$carbocycloalkyl where 1, 2 or 3 carbon ring members are optionally replaced by —NR'—, —O—, —S—, —S(=O)— or —S(=O)$_2$—, where R' is hydrogen or is selected from the group consisting of Cl, Br, $(C_{1-5})$alkyl, $(C_{3-6})$cycloalkyl, $(C_{6-10})$aryl, $(C_{6-10})$aryl$(C_{1-4})$alkyl, $(C_{1-5})$alkylNHC(=O)—, $(C_{1-5})$alkoxyC(=O)—, $R^aR^bNC$(=O)—, $(C_{1-5})$alkylC(=O)—, $(C_{6-10})$arylC(=O)—, $(C_{6-10})$aryl$(C_{1-4})$alkylC(=O)—, $(C_{6-14})$aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, $(C_{1-5})$alkyl, $(C_{3-6})$cycloalkyl, $(C_{1-5})$alkylNHC(=O)—, $(C_{1-5})$alkylC(=O)—, $(C_{6-14})$aryl, $(C_{6-10})$aryl$(C_{1-4})$alkyl, heteroaryl comprising 4 to 10 ring atoms with at least one heteroatom selected from O, S and N in the ring, or heterocyclyl$(C_{1-4})$ alkyl, the heterocycloalkyl group containing 2-10 carbon atoms and 1 to 4 heteroatoms selected from N, O or S;

$R^4$ is selected from the group consisting of $(C_{1-5})$alkyl, $(C_{3-7})$cycloalkyl, $(C_{3-6})$cycloalkyl-$(C_{1-3})$alkyl, $(C_{6-12})$aryl and $(C_{5-6})$carbocyclyl where 1, 2 or 3 carbon ring members are replaced by —NR'—, —O—, —S—, —S(=O)— or —S(=O)$_2$—, where R' is hydrogen or is selected from the group consisting of $(C_{1-5})$alkyl, $(C_{1-5})$alkylNHC(=O)—, $(C_{1-5})$alkylC(=O)—, $(C_{3-6})$cycloalkyl, heterocycloalkyl containing 2-10 carbon atoms and 1 to 4 heteroatoms selected from N, O or S, $(C_{6-12})$aryl, $(C_{6-12})$heteroaryl, $(C_{1-6})$alkylaryl, $(C_{6-12})$aryl$(C_{1-6})$alkyl, $(C_{1-5})$alkylC(=O)—, $(C_{1-5})$alkoxyC(=O)— and —S(=O)$_2$NH$(C_{1-5})$alkyl; and $R_5$ is selected from the group consisting of $(C_{1-5})$alkyl, $(C_{1-5})$alkoxy, $(C_{3-7})$cycloalkyl, $(C_{3-6})$cycloalkyl-$(C_{1-3})$alkyl, $(C_{6-10})$aryl, $(C_{6-10})$aryloxy, $(C_{7-12})$arylalkyl, $(C_{7-12})$alkylaryl, $(C_{7-12})$arylalkoxy; or a salt or derivative or bioisostere or prodrug thereof.

In a preferred subgroup of the compounds of formula V m is 1; and n is 1, 2 or 3; or a salt thereof; in this subgroup W may be —CH$_2$—; $X_1$ and $X_2$ both may be chloro; or $X_1$ may be chloro and $X_2$ may be —CF$_3$.

In certain compounds of each of the above formulae I, II, IIA, III, IV and V in which $R_1$ and/or $R_2$ are halo-alkyl, such as a —CF$_2$-alkyl or —CF$_3$ group, under certain conditions said compounds may be found to be less stable than the corresponding compounds of the above formulae I, II, IIA, III, IV and V in which $R_1$ and/or $R_2$ are not halo-alkyl. Without being bound by any theory proposed herein, one skilled in the art will find it reasonable that the electronic-withdrawing inductive effect of one or more halo-alkyl groups $R_1$ and/or $R_2$ attached to the same carbon as the $X_1X_2N$— group may destabilize said compound. However, in certain compounds wherein $R_1$ and/or $R_2$, and/or $R_0$ and/or $R_{00}$, are also substituted with electron-donating substituents, such as a —OCH$_3$ group, the electron-donating inductive effect may counteract to stabilize said compound. One skilled in the art may readily design and prepare the compounds of the above formulae I, II, IIA, III, IV and V to provide compounds with both optimal biological activity and desired stability.

Certain compounds of formula V include compounds wherein W is —CHR$_3$— wherein R$_3$ is selected from the group consisting of $(C_{1-5})$alkyl, $(C_{3-7})$cycloalkyl, $(C_{3-6})$cycloalkyl$(C_{1-3})$alkyl, $(C_{5-6})$carbocycloalkyl where 1, 2 or 3 carbon ring members are optionally replaced by —NR'—, —O—, —S—, —S(=O)— or —S(=O)$_2$—, where R' is hydrogen or is selected from the group consisting of $(C_{1-5})$alkyl, $(C_{1-5})$alkylNHC(=O)—, $(C_{1-5})$alkylC(=O)—, $(C_{3-6})$cycloalkyl, heterocycloalkyl containing 2-10 carbon atoms and 1 to 4 heteroatoms selected from N, O or S, $(C_{6-12})$aryl, $(C_{6-12})$heteroaryl, $(C_{1-6})$alkyl$(C_{6-10})$aryl, $(C_{6-12})$aryl$(C_{1-6})$alkyl, $(C_{1-5})$alkylC(=O)—, $(C_{1-5})$alkoxyC(=O)—, >C=O, and —S(=O)$_2$NH$(C_{1-5})$alkyl; $X_1$ and $X_2$ both are chloro; or $X_1$ is chloro and $X_2$ is —CF$_3$; and Z is selected from the group consisting of —SO$_3$H and —S(=O)$_2$NR$^c$R$^d$ wherein R$^c$ and R$^d$ are each independently hydrogen or selected from the group consisting of $(C_{1-5})$alkyl, $(C_{1-5})$alkylNHC(=O)—, $(C_{1-5})$alkylC(=O)—, $(C_{3-6})$cycloalkyl, $(C_{6-14})$aryl, $(C_{6-10})$aryl$(C_{1-2})$alkyl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S; or a salt thereof, whereby the subgroup with $X_1$ is chloro is preferred.

Another group of compounds of formula V includes compounds wherein W is selected from the group consisting of —S—, —S(=O)—, —S(=O)$_2$— and —NR$_3$—; $X_1$ and $X_2$ both are chloro; or $X_1$ is chloro and $X_2$ is —CH$_3$ or —CF$_3$; R$_3$ is selected from the group consisting of $(C_{1-5})$alkyl, $(C_{3-7})$cycloalkyl and $(C_{3-6})$cycloalkyl-$(C_{1-3})$alkyl; or a salt thereof.

In certain compounds of formula I, $R_1$ and $R_0$ together with the two carbon atoms to which they are attached may form a ring with 4 to 6 or 7 ring members with the $(X_1X_2)$N-substituent being outside the ring. The remaining substituents $X_1$, $X_2$, $R_2$, $R_{00}$, Y and Z have the meanings attributed to formula I. The resulting N-halogenated amino compounds may be N-halo- or N,N-dihalo amino compounds. In most cases the ring members of the rings will be carbon atoms. In some cases, one or two carbon atoms may be replaced with nitrogen. The ring may be saturated or aromatic. If the ring is saturated one or two methylene groups may be replaced with a substituted methylene group (the substituents being $(C_{1-5})$ alkyl or halogen selected from the group of fluoro or chloro) or the >C=O group. In some rings the >C=O group may be adjacent to nitrogen. The ring becomes an aromatic ring (for example, a benzene ring) if, in addition, $R_{00}$ together with $R_2$ forms a double bond. Optionally in such an aromatic ring, one or two ring carbon atoms may be replaced with nitrogen (for example, forming a pyridine ring).

Typical but not limiting examples of these cyclic compounds are the compounds of

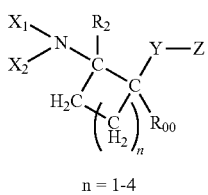

n = 1-4 formula VI wherein: $X_1$, $X_2$, $R_2$, $R_{00}$, Y and Z are as defined above; or a salt, or a derivative, or a bioisostere or a prodrug thereof.

In certain other compounds of formula VI, $R_0$ together with $X_2$ form an alkylene group with 1 to 4 carbon atoms. The remaining substituents $X_1$, $R_1$, $R_2$, $R_{00}$, Y and Z are as defined in formula I. The halogenated nitrogen atom together with $R_0$ and the carbon atom with the substituents $R_1$ and $R_2$ and the carbon atom with the group —YZ form a saturated ring. In this ring one or two methylene group may be replaced with a substituted methylene group (the substituents being $(C_{1-5})$ alkyl or halogen selected from the group of fluoro or chloro), —NR'— or the >C=O group R' may be hydrogen, $(C_{1-5})$ alkyl or halogen selected from the group of chloro or bromo. In some rings the >C=O group may be adjacent to nitrogen. It is preferred that the carbon atom adjacent to the $X_1$N— group does not have hydrogen to avoid dehydrohalogenation. If, in addition, R' is chloro or bromo the resulting amino compound will be dihalogenated. A typical example of these further cyclic compounds are the compounds of formula VII

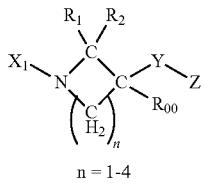

n = 1-4 wherein: $X_1$, $R_1$, $R_2$, $R_{00}$, Y and Z have the above meanings; or a salt, or a derivative, or a bioisostere or a prodrug thereof.

In a group of compounds of general formulae I, II, IIA, III, IV, V, VI and VII, the group $(X_1X_2)$N— is in beta, gamma or delta position of the moiety Z.

In a group of compounds of general formulae I, II, or IIA, the group $(X_1X_2)$N— is in epsilon or omega position of the moiety Z. In certain compounds of formula I, Y is a single bond. In certain compounds of formula I, II, or IIA, Y is a $(C_{1-12})$alkylenyl, preferably a $(C_{1-6})$ alkylenyl group.

In certain variations of the compounds of formulae I, II, IIA, III, IV, V, VI and VII, the variable R' at each occurrence in a formula is independently hydrogen or is selected from the group consisting of Cl, Br, $(C_{1-5})$alkyl, $(C_{3-6})$cycloalkyl, $(C_{6-10})$aryl, $(C_{6-10})$aryl$(C_{1-4})$alkyl, $(C_{1-5})$alkylNHC(=O)—, $(C_{1-5})$alkoxyC(=O)—, $R^aR^bNC(=O)$—, $(C_{1-5})$alkylC(=O)—, $(C_{6-10})$arylC(=O)—, $(C_{6-10})$aryl$(C_{1-4})$alkylC(=O)—, $(C_{6-14})$aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, $(C_{1-5})$alkyl, $(C_{3-6})$cycloalkyl, $(C_{1-5})$alkylNHC(=O)—, $(C_{1-5})$alkylC(=O)—, $(C_{6-14})$aryl, $(C_{6-10})$aryl$(C_{1-4})$alkyl, heteroaryl comprising 4 to 10 ring atoms with at least one heteroatom selected from O, S and N in the ring, or heterocyclyl$(C_{1-4})$ alkyl, the heterocycloalkyl group containing 2-10 carbon atoms and 1 to 4 heteroatoms selected from N, O or S.

In other variations of the compounds of formulae I, II, IIA, III, IV, V, VI and VII, the variable R' at each occurrence in a formula is hydrogen or is selected from the group consisting of $(C_{1-5})$alkyl, $(C_{3-6})$cycloalkyl, $(C_{6-10})$aryl, $(C_{6-10})$aryl$(C_{1-4})$alkyl, $(C_{1-5})$alkylNHC(=O)—, $(C_{1-5})$alkoxyC(=O)—, $(C_{1-5})$alkylC(=O)—, $(C_{6-10})$arylC(=O)—, $(C_{6-10})$aryl$(C_{1-4})$alkylC(=O)—, $(C_{6-14})$aryl, $(C_{6-10})$aryl$(C_{1-4})$alkyl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S.

The present application also includes the following compounds:

2-(dichloroamino)-2-trifluoromethyl-3,3,3-trifluoropropane-1-sulfonic acid;
2-(chloro(methyl)amino)-2-methylpropane-1-sulfonic acid;
2-(dichloroamino)-2-methyl-1,1-di-trifluoromethylpropane-1-sulfonic acid;
2-(chloro(methyl)amino)-1,1,2-trimethylpropane-1-sulfonic acid;
2-(dibromoamino)-2-methylpropane-1-sulfonic acid;
2-(bromo(trifluoromethyl)amino)-2-methylpropane-1-sulfonic acid;
2-(dibromoamino)-1,1,2-trimethylpropane-1-sulfonic acid;
2-(bromo(methyl)amino)-1,1,2-trimethylpropane-1-sulfonic acid;
3-(dichloroamino)-2,2,3-trimethylbutane-1-sulfonic acid;
3-(chloro(methyl)amino)-3-methylbutane-1-sulfonic acid;
2-(dichloroamino)-2-trifluoromethylpropane-1-sulfonic acid;
2-(chloro(trifluoromethyl)amino)-2-trifluoromethylpropane-1-sulfonic acid;
4-(dichloroamino)-3,3,4-trimethylpentane-1-sulfonic acid;
2-(dichloroamino)-1,2-di-methyl-1-ethylpropane-1-sulfonic acid;
3-(chloro(methyl)amino)-propylphosphonic acid;
5-(dibromoamino)-5-methyl-1-methylhexylphosphonic acid;
5-(bromo(trifluoromethyl)amino)-5-methylhexylphosphonic acid;
diethyl 2-(dichloroamino)-2-methylpropylphosphonate;
diethyl 2-(chloro(trifluoromethyl)amino)-2-ethylbutylphosphonate;
2-(dichloroamino)-2-cyclopropyl-1-methylpropylphosphonic acid;
2-(chloro(2',2',2'trifluoroethyl)amino)-2-methyl-1-methylpropylphosphonic acid;
2-(dichloroamino)-propylphosphonic acid;
2-(chloro(methyl)amino)-2-pentafluoroethylpropylphosphonic acid;
3-(dichloroamino)-3-methylbutylphosphonic acid;
6-(chloro(trifluoromethyl)amino)-2,6-dimethylheptylphosphonic acid;
4-(dichloroamino)-2,4-dimethypentylphosphonic acid;
8-(dichloroamino)-7,8-dimethylnonylphosphonic acid;
8-(chloro(methyl)amino)-8-methylnonylphosphonic acid;
3-(4-chlorophenyl)-2-(dichloroamino)-2-methylpropane-1-sulfonic acid;
3-(4-chlorophenyl)-2-(chloroamino)-2-methylpropane-1-sulfonic acid;
3-(2-(dichloroamino)-2-methylpropoxy)propane-1-sulfonic acid;

3-(2-(chloroamino)-2-methylpropoxy)propane-1-sulfonic acid;
3-(2-(dichloroamino)-2-methylpropoxy)-3-oxopropane-1-sulfonic acid;
3-(2-(chloroamino)-2-methylpropoxy)-3-oxopropane-1-sulfonic acid;
3-(2-(dichloroamino)-2-methylpropylamino)-3-oxopropane-1-sulfonic acid;
3-(2-(chloroamino)-2-methylpropylamino)-3-oxopropane-1-sulfonic acid;
3-((2-(dichloroamino)-2-methylpropyl)(methyl)amino)-3-oxopropane-1-sulfonic acid;
3-((2-(chloroamino)-2-methylpropyl)(methyl)amino)-3-oxopropane-1-sulfonic acid;
3-(2-(dichloroamino)-2-methylpropoxy)-2,2-dimethyl-3-oxopropane-1-sulfonic acid;
3-(2-(chloroamino)-2-methylpropoxy)-2,2-dimethyl-3-oxopropane-1-sulfonic acid;
2-(3-(dichloroamino)-3-methylbutanoyloxy)ethanesulfonic acid;
2-(3-(chloroamino)-3-methylbutanoyloxy)ethanesulfonic acid;
2-(2-(dichloroamino)-2-methylpropylsulfonyl)ethanesulfonic acid;
2-(2-(chloroamino)-2-methylpropylsulfonyl)ethanesulfonic acid;
2-(dichloroamino)-N,N-2-trimethylpropane-1-sulfonamide;
2-(chloroamino)-N,N-2-trimethylpropane-1-sulfonamide;
2-(dichloroamino)-N,2-dimethylpropane-1-sulfonamide;
2-(chloroamino)-N,2-dimethylpropane-1-sulfonamide;
N-(2-(dichloroamino)-2-methylpropylsulfonyl)acetamide;
N-(2-(chloroamino)-2-methylpropylsulfonyl)acetamide;
(1-(dichloroamino)cycloheptyl)methanesulfonic acid; and
(1-(chloroamino)cycloheptyl)methanesulfonic acid;

and the pharmaceutically acceptable salts thereof.

The compounds of formula I are preferred in which Z is —$SO_3H$; or a salt thereof. Among these preferred compounds $X_1$ is chloro; $X_2$ is selected from group consisting of hydrogen, Cl, $(C_{1-6})$alkyl, $(C_{1-6})$haloalkyl; $R_1$ and $R_2$ are each independently selected from the group consisting of $(C_{1-5})$alkyl, halo$(C_{1-5})$alkyl, $(C_{3-12})$cycloalkyl, $(C_{3-6})$cycloalkyl$(C_{1-3})$alkyl, $(C_{6-10})$aryl$(C_{1-4})$alkyl, and $(C_{6-14})$aryl; $R_1$ and $R_2$ together with atom to which they are linked can form a substituted or unsubstituted heterocyclic ring having 3-8 ring atoms, wherein 1-2 ring atoms in heterocyclic system are selected from N, O and S; $R_0$ and $R_{00}$ are independently selected from the group consisting of hydrogen, $(C_{1-5})$alkyl and $(C_{1-5})$haloalkyl; Y is a member selected from a single bond, —O—, and a divalent $(C_{1-18})$alkylenyl group in which optionally one or two methylene groups are replaced with a mono- or di-substituted methylene group, or optionally where one or two methylene groups are replaced with 1 or 2 —NR'—, —O—, —S—, —S(=O)—, >C=O, —C(=O)O—, —OC(=O)—, —C(=O)NH—, —NHC(=O)—, —C(=O)NR'—, —NR'C(=O)—, or —S(=O)$_2$—; and R' is selected from the group consisting of $(C_{1-6})$alkyl, $(C_{1-6})$haloalkyl, and $(C_{3-8})$ cycloalkyl.

Pharmaceutical Compositions

The present application also comprises a pharmaceutical composition comprising a compound or a salt described herein and a pharmaceutically acceptable excipient. This composition is suitable for the treatment of a bacterial, microbial, sporal, fungal or viral infection.

The compounds or salts and compositions described herein are useful in a method of preventing or treating an infection caused by a bacterial, a microbial, a sporal, a fungal or a viral activity in a mammal, the method comprising the administration of a bactericidal, antibacterial, anti-infective, antimicrobial, sporicidal, disinfectant, antifungal and antiviral amount of an N-halo- or N,N-dihalo-amino compound or salt thereof or a pharmaceutical composition containing the compound or salt thereof.

The compounds or salts described herein may be used for the preparation of a medicine for the treatment of a bacterial, a microbial, a sporal, a fungal or a viral activity in a mammal.

Compositions of the compounds of the formulae above may often be utilized in liquid form, for example, as solutions, or suspensions, emulsions and the like. In that case the concentration of the N-halo- or N,N-dihaloamino compounds or their derivatives will be up to about 1 M (molar), up to about 2 M, about 3 M, about 4 M or up to the saturation concentration of the N-halo- or N,N-dihaloamino compounds or their derivatives. As used herein, the compositions further comprising a solvent may include water to form an aqueous composition, and the solvent may comprise aqueous and organic solvents and their combinations. A preferred composition of the present application comprises a composition having a concentration of the N-halo- or N,N-dihaloamino compound or its derivative between about 0.001 mM to about 4 M (molar), 0.05 mM to about 2 M, about 0.01 mM to about 1 M, about 0.1 mM to about 0.1 M or about 0.1 to about 50 mM. The pH range of the solution may be between about 1 to about 13, about 2 to about 8, about 3 to about 4.8, about 3 to about 4.5, about 3.5 to about 4.5, or at about 3.5, or at about 2. The pH can be easily adjusted by various buffer systems known in the art.

The present application also provides new bactericidal, antibacterial, anti-infective, antimicrobial, germicidal, sporicidal, disinfectant, antiviral and antifungal compositions which include an N-halogenated amino compounds of the formulae I-VII.

With respect to the pharmaceutical compositions described herein formulae I-VII, the variables $X_1$, $X_2$, $R_1$, $R_2$, $R_0$, $R_{00}$, $R_3$, $R_4$, $R_5$, W, Y and Z assigned to each formula described herein apply.

Preferred derivatives of the compounds of formula III include pharmaceutically acceptable salts, lower alkyl or alkanoyl derivatives of the —NH— group of W. The pharmaceutically acceptable salts of compounds of formulae I-VII or their derivatives include salts with pharmaceutically acceptable cations. The compounds of formula I-VII include salts of bases with the —$SO_3H$, —$SO_2NH_2$ groups. Pharmaceutically acceptable salts also include ammonium, alkali metal, magnesium, or calcium salts, any organic amine salts or ion pairing with tetraalkylammonium salt $R_4N^+X^-$ or tetraalkylphosphonium salt $R_4P^+X^-$, where X is OH, Cl, Br or $HSO_4$. Alkali metal salts, Mg, Ca and Al salts are of interest. The alkali metal salts are of particular interest, particularly lithium, sodium, or potassium salts.

Examples of acid addition salts include, but are not limited to, mineral or organic acid salts of basic residues such as substituted amines (for example, when an —N(Me)— group is present and Z is —$SO_2NH_2$); alkali or organic salts of acidic residues Z. Pharmaceutically acceptable salts include, but are not limited to, hydrohalides, sulfates, methosulfates (quaternary ammonium sulfates), methanesulfonates, toluenesulfonates, nitrates, phosphates, maleates, acetates, lactates, oxalates, fumerates, succinates, and the like.

Lists of suitable salts are found, for example, in *Remington's Pharmaceutical Sciences,* 17th ed., Mack Publishing Company, Easton, Pa., 1985, p. 1418, or *The Merck Index,* Thirteenth Edition, 2001, Published by Merck Research Laboratories Division of Merck & Co., Inc. on pages MISC-22 and MISC-23, the disclosures of which are hereby incorporated by reference in their entirety. The pharmaceutically acceptable acid addition salts include salts among others with hydrochloric, sulfonic, phosphoric, nitric acid, acetic, benzenesulfonic, toluenesulfonic, methanesulfonic acid, camphorsulfonic acid, oxalic acid, succinic acid, fumeric acid, and other acids.

Further derivatives of the compounds of formula I-VII also include the N-halo amino compounds or the N,N-dihaloamino compounds in which certain groups of the amino compound molecule are protected by protecting groups.

The term "composition" as used herein, refers to various forms of the compounds or compositions of the present application, including solids such as powders, mixtures of powders and the like, emulsions, suspensions as well as solutions and gaseous formulations, such as aerosols.

In general, the compositions may be maintained in acidic form, that is at a pH below 7, for example about 6.8, that is at a pH between about 2.0 to about 7.0, about 2.0 to about 6.8, about 2.5 to about 6.5, about 2.5 to about 6.0, or about 2.5 to about 5.0, or about 3.0 to about 5.0, or at a pH of about 3.5. As described below, the pH may be kept below 5, that is, at a pH range of about 3.0 to about 4.5, or about 3.5 to about 4.5, or at a pH about 3.5. While preferred are compositions where the pH of the composition is acidic in certain compositions, the selection of the pH will depend on many factors, including the specific use of the N,N-dihaloamino or N-halo amino compound (whether in vitro or in vivo), the type of the infection treated (for example, whether the infection is caused by bacteria, yeast, fungi or viruses), the site of the infection (for example, whether it is an infection of the eye, the larynx or the urethra or any target tissue or organ), the severity of the infection, the sensitivity of the patient, etc. As noted above, the desired pH can be easily achieved by the appropriate selection of buffer systems as well known to the person skilled in the art.

In certain instances for the compositions of the present application, a pH between 7 and 13 may be suitable, a pH between 9 and 13, or a pH between 7 and 9 may be suitable. In certain variations, the compositions may be maintained in a neutral, slightly basic or basic form; that is at a pH of about 7, for example 7.2, or for example at a pH between about 7 to about 9, that is at a pH range between 7.0 to 7.2, at a pH of about 7.2 to about 7.5, at a pH of about 7.5 to about 8, or at a pH of about 8 to about 8.5, or at a pH of about 8.5 to about 9, or at a pH of about 8. The desired pH may depend, in part, on the stability of the compounds and compositions as well as their intended applications.

In another aspect of the composition, the solutions comprise N,N-dihaloamino or N-halo amino compounds in the concentration range of about 0.01 mM to about 4 M, about 1 M to about 4 M, about 2 M to about 4 M or about 3 M to about 4 M, or about 0.1 to about 100 millimolar (mM).

In a further aspect the composition is isotonic and physiologically balanced.

The N,N-dihaloamino and N-halo amino compounds differ significantly from HOCl because they maintain an oxidizing potential with significant stability and bactericidal activity, and yet they are less toxic than HOCl. N,N-dihaloamino or N-halo amino compounds are also stable enough to diffuse some distance (for example inside biofilm) before oxidizing susceptible target molecules. The low molecular weight N,N-dihaloamino or N-halo amino compounds of the present application with Y being a lower alkylene group with up to 6 methylene groups are more lipophilic molecules than N,N-dihaloamino or N-halo amino compounds in which Y is a single bond. N,N-dihaloamino compounds and N-haloamino compounds of the present application are stable as dry powders and dried solutions can be reconstituted to full potency.

Surprisingly, it has been found that, while the N,N-dihaloamino or N-halo amino compounds of the present application have effective bactericidal, antibacterial, anti-infective, antimicrobial, sporicidal, disinfectant, antifungal and antiviral properties, they also have low cytotoxicity. That is especially true when the compositions are acidic.

In a further aspect, the compositions are stabilized to meet the requirement of being useable as compositions for the treatment or prevention of bacterial, microbial, germ, spore, fungal and viral infections or contaminations.

In another aspect the stabilization of the composition is provided by storing the compositions in a receptacle that will ensure sufficient stability to control bacterial, microbial, spore, fungal and viral infections or contaminations. In one aspect, the compositions as disclosed herein may be prepared to be sufficiently stable, or the composition having long term stability and shelf life for the intended applications for at least two weeks, preferably at least one month, preferably at least about three months, more preferably at least about six months, more preferably at least about 12 months, and most preferably, at least about 24 months. Depending on the intended application for the compositions disclosed herein, the composition may be stored at room temperature or about 25° C., or below room temperature, such as at about 20° C., 15° C. or at about 10° C.

The present application provides pharmaceutical compositions which include an N,N-dihaloamino compound or N-haloamino compound of the formulae I-VII or their salts or derivatives, as described above. The preferred derivatives are pharmaceutically acceptable salts.

In another aspect, the compositions described herein comprising a mono- or dihaloamino compound of the formulae I-VII or their derivatives are compositions in which $X_1$ or $X_2$ is chloro. In yet another aspect, the compositions described herein comprising a mono-haloamino compound of the formulae I-VII or their derivatives are compositions in which the haloalkyl is linked to nitrogen, especially —$CF_3$ or —$C_2F_5$. In another aspect, the compositions of the present application further comprise a pharmaceutically acceptable carrier.

All the features, characteristics and ranges described in the present application, in any aspect, whether described as of interest or as particular or not, may be combined with one another. For example, a substituent of interest in the formulae depicted herein may be combined with another more broadly defined, not emphasized substituent described herein. For example, the substituent Z that is —$SO_3H$ may be combined with substituents $R_3$ and $R_4$ that are other than hydrogen.

Also provided are pharmaceutical compositions wherein the haloamino compounds of formulae I-VII or their derivatives are combined with halogenated compounds derived from hypohalous acid derivatives or a source of a hypohalous acid derivative. Such hypohalous derivatives include a hypohalous acid or a source of hypohalous acid or a salt of a hypohalous acid, in particular, sodium or potassium hypochlorite. Such pharmaceutical compositions have anti-inflammatory, immuno-modulatory, bactericidal, antibacterial, anti-infective, antimicrobial, sporicidal, disinfectant, antifungal and antiviral effect and tissue healing stimulation without exhibiting substantial stimulation of myeloperoxidase activity in a mammal. The hypochlorite titer of these pharmaceutical compositions is below or equal to about 1 mole/liter (1 molar) of available chlorine, particularly of a hypochlorite of an alkaline metal, especially sodium hypochlorite. The minimum titer of the composition is greater than or equal to about 1 picomole/liter. The N-chloramine titer of these compositions is less than or equal to about 5 moles/liter (5 molar) with a minimum of 0.01 femtomoles/liter. Among the hypohalous derivatives, the chloro and bromo derivatives are preferred. Most preferred are the chloro derivatives. In certain aspects, it is generally preferred to combine a mono- or di-halogenated amino compound with hypohalous derivative where in each case the halogen species are the same, for example chloro.

Processes for the Preparation of Compounds of the Application

The compounds of formulae I-VII can be prepared by the following methods. In one method, the preparation comprises the following steps using an amino acid with the amino group attached to a tertiary carbon atom (for example, an appropriately 5,5-disubstituted 2-pyrrolidone which can be hydrolyzed to the corresponding amino acid) or an amino alcohol with an amino group attached to a tertiary carbon obtained by condensation of a primary amine with a halo alkanol with two substituents attached to the carbon to which the halogen is attached (for example, the condensation of methyl amine with 2-methyl-2-chloropropanol, 2-methyl-2-bromo-propanol or 2-bromo-2-methyl-2-phenylethanol):

(1) Protection of the amino group;
(2) Double alkylation of carbon atom in α-position to amino group ("Enantioselective Synthesis of Alpha-Branched Alpha-Amino-Acids with Bulky Subtituents," *Liebigs Annalen*, (2):217-222, 1995 February, the disclosure of which is incorporated herein in its entirety)
(3) Reduction of a N-protected carboxylic acid to the amino alcohol (direct reduction of the acid or via an ester)—optional if amino acid is starting material;
(4) Introduction of the group Z (for example, —SO$_3$H or —PO$_3$H$_2$);
(5) Backbone elongation of Y (for example, by condensation)—optional if desired;
(6) Deprotection of amino group;
(7) Introduction of non-halo X$_2$ after deprotection of amino group (for example, by alkylation or acylation, optionally followed by reduction);
(8) Halogenation to introduce X$_1$ and X$_2$ or only X$_1$ if X$_2$ is non-halogen;
(9) Salt-formation of Z or any basic or acidic groups in molecule;
(10) Conversion of a salt into an acid or base;
(11) Conversion of one salt into another salt; or
(12) Derivatization of the Z or W group or other groups in the compounds described herein.

It is understood that the sequence of these various steps is not fixed, unless the different functional groups make a particular sequence mandatory, because, in general, the most reactive groups have to be introduced last in the sequence of steps. Under certain reaction conditions, depending on the nature and type of functional groups of the compounds that is used, controlled and selective oxidation of the compounds may be performed using the type and stoichiometry of the oxidizing agent, such that certain functional groups such as an amine, that may be selectively oxidized while maintaining another group, such as a thioether, un-oxidized. Similarly, the reaction conditions may be adjusted such that the selective oxidation to the correspond sulfoxide or sulfone may be obtained as known in the art.

Because the N-halo- and the N,N-dihalo groups are the most chemically reactive groups in the compounds of formulae I-VII, in general, the last step in the synthesis will be the halogenation of the amino group(s). Such halogenation may involve halogenation of a primary amino group in which one or both hydrogen atoms of the amino group are being replaced with halogen, leading to compounds of the formulae I-VII in which X$_1$ is chloro or bromo and X$_2$ is hydrogen, or X$_1$ and X$_2$ are both halogen atoms (chloro or bromo). Alternatively, the halogenation may involve halogenation of one or more secondary amino groups, leading to compounds of the formulae I-VII in which X$_1$ is chloro or bromo and X$_2$ is C$_{1-5}$alkyl, C$_{3-6}$cycloalkyl, C$_{3-6}$cycloalkyl C$_{1-3}$alkyl or halo C$_{1-5}$alkyl.

For the compounds of formulae I-VII in which X$_1$ is chloro or bromo and X$_2$ is hydrogen, or X$_1$ and X$_2$ are both chloro or bromo, the last step halogenation in general will be preceded by a step which introduces the group Z, for example, the sulfonic acid group. This can be achieved in a variety of ways. According to one embodiment, a leaving group, such as an alkyl or aryl sulfonate of a —CH$_2$OH group at the right end of the backbone (where Z will be located) will be replaced with a sulfite, for example, sodium sulfite, to afford the corresponding sulfonic acid.

Prior to the introduction of the group Z (for example, the —SO$_3$H group), the amino acid backbone may be extended by at least one but up to 18 —CH$_2$— groups, or —CH$_2$— groups interrupted by other groups capable of withstanding halogenation of the N-terminal or other amino groups present in the molecule, such as —O— or —S(=O)$_2$—.

In one embodiment, the carboxy group of an amino acid at the C-terminal end, such as α,α-dialkylated glycine may be reduced to the corresponding primary alcohol, as described in more detail below. Following the reduction step the primary alcohol will be esterified with an alkyl or aryl sulfonyl chloride, such methane sulfonyl chloride or benzene sulfonyl chloride, toluene sulfonyl chloride or chlorobenzene sulfonyl chloride which will then be converted into a sulfonic acid of the formulae I-VII as noted above.

For the compounds of the formulae I-VII in which X$_1$ is chloro or bromo and X$_2$ is C$_{1-5}$alkyl, C$_{3-6}$cycloalkyl, C$_{3-6}$cycloalkyl C$_{1-3}$alkyl or halo C$_{1-5}$alkyl, an appropriate α- or ω-halo alkanol, for example 2-methyl-2-chloropropanol or 2-methyl-2-bromopropanol, can be reacted with a C$_{1-5}$alkyl amine, such as methyl amine, under appropriate stoichiometric conditions to obtain the corresponding monoalkylated amino alcohol, which will be esterified after N-protection with an alkyl or aryl sulfonyl chloride acid, such methane sulfonyl chloride or benzene sulfonyl chloride toluene sulfonyl chloride, a bromo-benzene sulfonyl chloride to the corresponding ester, which will then be converted into a sulfonic acid. The sulfonic acid, in turn can be halogenated to obtain a compound of the formulae I-VII in which X$_1$ is chloro or bromo and X$_2$ is C$_{1-5}$alkyl, C$_{3-6}$cycloalkyl or halo C$_{1-5}$alkyl. Similarly, trifluoromethyl iodide can be used to monotrifluoromethylate an appropriate O-protected amino alcohol and to obtain the appropriate starting material for halogenation as described above.

Another method for preparing a secondary amine starting material involves amides which can be reduced to secondary amines with various reducing agents, for example, LiAlH$_4$.

Prior to esterification of the primary amino alcohol with methane-, benzene-, chlorobenzene- or toluene-sulfonyl chloride, the linking group may be extended by various methods, as for example described in U.S. Pat. No. 4,386,103 Pogany, the disclosure of which is herein incorporated by reference in its entirety. In one embodiment, the amino group may be protected and then the primary hydroxyl group subjected to various coupling or condensation reactions analogous to those as, for example, described by Pogany. For example, the appropriately N-protected amino alcohol may be reacted with 2-bromo ethanesulfonic acid [prepared as described in *Organic Syntheses*, Coll. Vol. 2, p. 558 (1943); Vol 10, p. 96 (1930), the disclosures of which are incorporated herein by reference in their entirety] to form an amino sulfonic acid in which the divalent linker Y contains an —O— group. This way the sulfonyl group can be introduced directly together with the extension of the linker Y.

Representative but not limiting synthetic procedures for preparing compounds provided herein are illustrated and described in detail below.

The N-halo- or N,N-dihaloamino phosphonic acids can be produced by halogenation, for example, chlorination, of the various amino phosphonic acids, the preparation of which is analogous to methods described in *JACS* Communications *J. Am. Chem. Soc.* 2004, 126, 4102-4103, *Organic Syntheses, Coll. Vol.* 10, p. 282 (2004); Vol. 75, p. 19 (1998), and in Chapter 13 "Asymmetric Synthesis of α-Substituted-β-Amino Phosphonates and Phosphinates and β-Sulfur Analogs" (Francisco Polacio et al.) in *Aminophosphonic and Aminophosphinic Acids: Chemistry and Biological Activity*, 1st edition, by Valery Kukhar and Harry R. Hundson, ISBN 04 71891495, Published May 1, 2000 by Wiley; and in *Enantioselective Synthesis of β-Amino acids*, 2$^{nd}$ edition, Eusebio Juaristi (Editor), V. A. Soloshonok (Editor), ISBN 0-471-46738-3, April 2005, the disclosure of all of which is incorporated herein by reference in their entirety.

A non-limiting specific procedure for preparing N,N-dihaloamino compounds is described below:

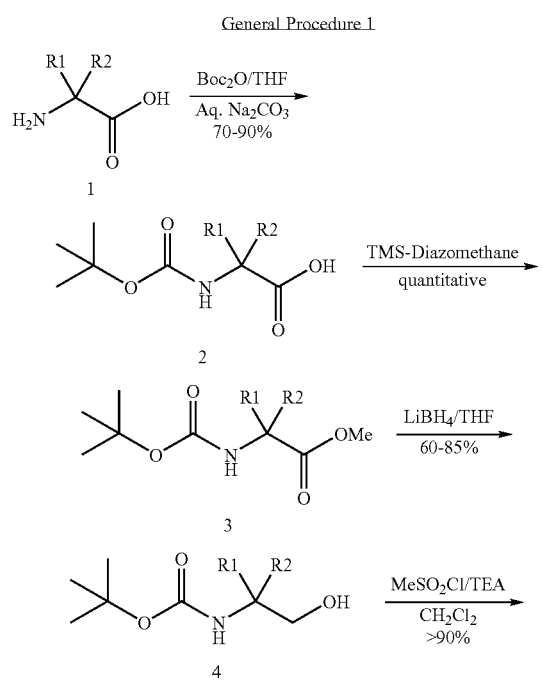

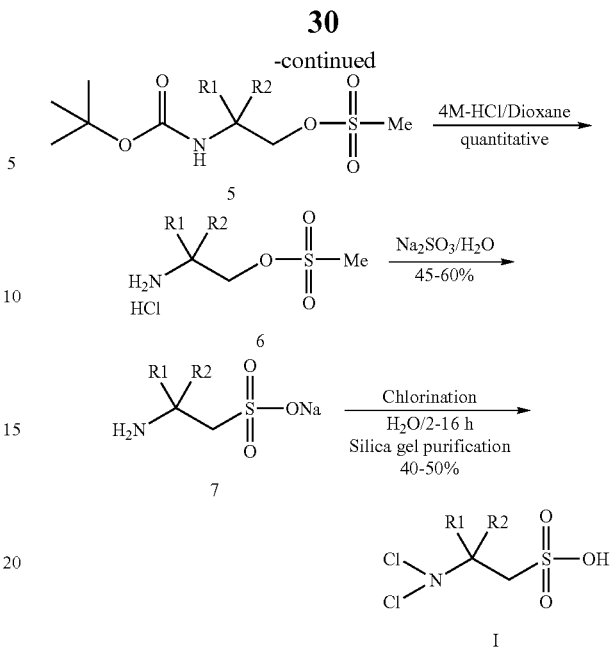

As shown in General Procedure 1, α-amino acid (1) is reacted with di-t-butyl dicarbonate ($Boc_2O$) in the presence of an organic or inorganic base to provide a Boc-protected amino acid (2). However, the protection of the amino group can also be carried out with other amino-protecting groups, for example, other carbobenzoxy groups, the FMOC group or trifluoroacetyl group. The transformation with $Boc_2O$ is typically carried out in an inert organic solvent, such as dioxane, tetrahydrofuran (THF), and the like, at low temperatures, e.g., from 0 to 25° C., such as 0° C. Suitable organic bases include triethylamine (TEA), pyridine, and suitable inorganic bases include sodium bicarbonate, sodium carbonate, sodium hydroxide and the like.

Methyl ester (3) of N-Boc-protected α-amino acid (2) can be generated by alkylation with a suitable methylating reagent such as trimethylsilyl-diazomethane, methyl iodide or other alkylating agents in the presence of an organic or inorganic base. A phase-transfer catalyst may also be used for this transformation. The transformation is typically carried out at low temperatures, e.g., 0° C., and after the addition, the reaction is allowed to warm to ambient temperature, e.g., about 25° C.

Compound (3) can be converted to a β-amino alcohol derivative (4) by using a number of reducing agents. For example, the transformation of the methylester to the hydroxymethyl substituent in (4) can be accomplished by reaction with lithium borohydride in a suitable solvent such as tetrahydrofuran, ethyl alcohol and methyl alcohol. Other suitable reducing agents are $LiAlH_4$ in dry ether at room temperature, or $BH_3$/THF. Alternatively, the acid (2) can be directly reduced to the alcohol (4) with $BH_3$/THF.

The N-protected β-amino alcohol derivative (4) is then converted to the methylsulfonate ester (5) by reacting with methanesulfonyl chloride (MsCl) or other sulfonyl chlorides, for example benzene sulfonyl chloride, toluene sulfonyl chloride, ethane sulfonyl chloride or the like and TEA in a non-polar organic solvent such as toluene, methylene chloride and the like. The reaction is carried out at ice cold to ambient temperature for about 2 to about 24 hours.

The methylsulfonate ester (5) is then treated with an acid to remove the t-butoxycarbonyl protecting group (Boc) and produce the salt (6). Removal of the protecting group may be carried out with acids, such as a trifluoroacetic acid (TFA), hydrochloric acid, p-toluenesulfonic acid, and the like, in an inert organic solvent such as dichloromethane, dioxane, THF, and the like. The deprotection is typically conducted at low to ambient temperatures (e.g., 0° C. to room temperature).

Reaction of mesylate derivative (6) with 1 M aqueous sodium sulfite in polar solvents such as water, DMF or THF affords respective β-amino sulfonate derivatives (7). Compound (7) is then converted to the N,N-dichloro derivative of formula I by electrophilic chlorination, for example, treatment with chlorine agents such as trichloroisocyanuric acid, This bromo compound is then converted to the sodium sulfonate derivative (10) by treatment with sodium sulfite in a polar solvent such as water and the like. The reaction is carried out at ambient temperature for about 2 to 6 hours. N-Chlorination of the amine (10), preferably in an inert solvent provided N,N-dichloro derivative I. This reaction can be performed with any number of known chlorinating reagents, trichloroisocyanuric acid, HOCl, HOBr or their salts (for example, NaOCl or KOCl, NaOBr), halohydantoins, such as dichlorohydantoin, chlorine gas and the like. The reaction is continued until completion, which typically occurs in from about 2 to about 12 hours.

Alternatively, N-protected β-amino alcohol derivatives (11) can be directly converted into the N,N-dichloroamine derivative of formula I as shown in another non-limiting General Procedure 3.

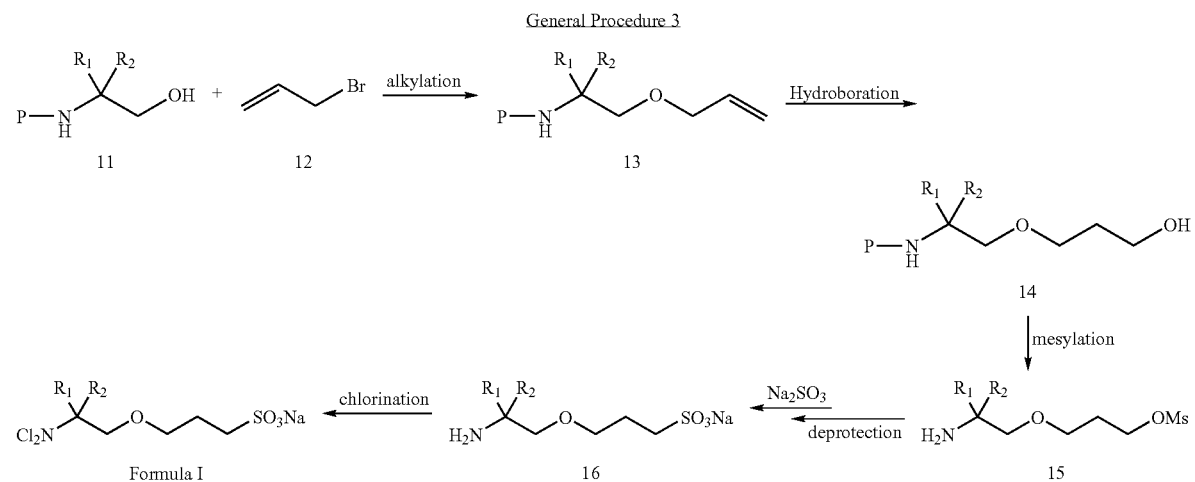

sodium hypochlorite, N-chloro succinimide, various N-chlorohydantoins and chlorine gas in a solvent such as water, N,N-dimethylformamide, methylene chloride and the like. The reaction is carried out at low temperature to ambient temperature for about 2 to about 24 hours.

Alternatively, β-amino alcohol derivatives (8) can be directly converted into the N,N-dichloroamine derivative of formula I in 3 steps as shown in another non-limiting General Procedure 2.

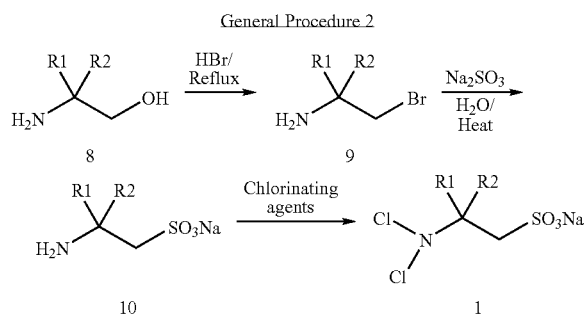

As shown in Scheme above, β-amino alcohol derivatives (8) (commercial or generated from respective carboxylic acid) is reacted with hydrobromic acid in water to provide the corresponding β-aminobromo derivatives (9).

As shown in General Procedure 3, the protected β-amino alcohol, (11) (where P is a suitable N-protecting group such as benzyloxycarbonyl or t-butyl dicarbonate) is reacted with allyl bromide. The reaction is carried out in a polar solvent such as DMF and in the presence of an inorganic base such as sodium hydride, potassium hydride, potassium carbonate and sodium carbonate and the like. The conversion of the intermediate (13) to the primary alcohol (14) is carried out using conditions and reagents well known to those skilled in the art, for example, by using 9-BBN in an appropriate solvent such as THF followed by oxidation with $H_2O_2$.

The intermediate primary alcohol (14) is then converted to the methylsulfonate ester (15) by reacting with methanesulfonyl chloride or other sulfonyl chlorides, for example, benzene-sulfonyl chloride, toluenesulfonyl chloride, ethanesulfonyl chloride, or the like, and TEA. The reaction is carried out at ice cold to ambient temperature for about 2 to about 24 hours. Conversion of the mesylate (15) through the intermediate β-amino sulfo derivative (16) to the N,N-dichloro derivative of formula I is carried out as described under General Procedure 1.

Further, N-protected β-amino alcohol derivatives (11) can be converted into the N,N-dichloroamine derivative of formula I as shown in another non-limiting General Procedure 4.

General Procedure 4

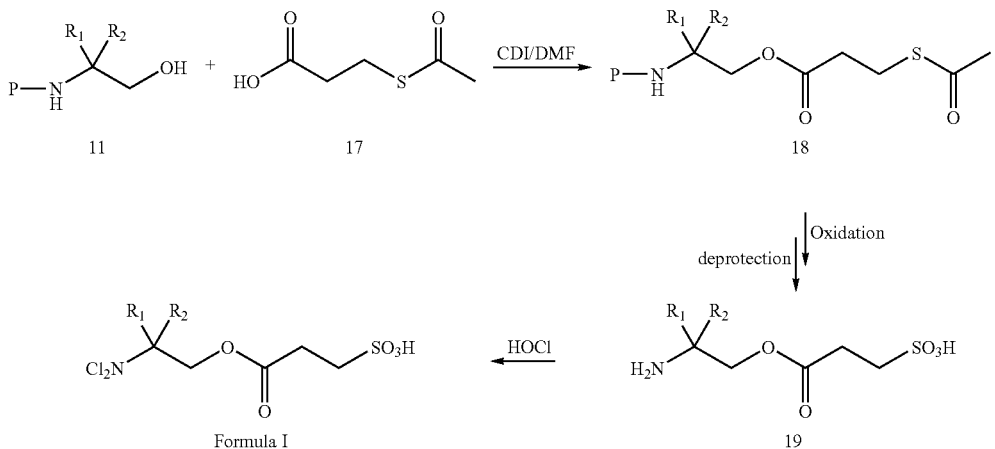

As shown in General Procedure 4, the N-protected (with suitable N-protecting groups such as benzyloxycarbonyl or di-t-butyl dicarbonate groups) amino alcohol (11) is coupled with 3-(acetylthio)propanoic acid (17), which may be prepared from commercially available 3-mercaptopropanoic acid by acetylation following the method described by An-Hu et al. (*J. Med. Chem.* 1999, 42, 706). The reaction is carried out in an inert solvent such as methylene chloride using an excess of acetyl chloride at ambient temperature for about 1 to about 2 days. The coupling is suitably carried out using conditions and reagents which are well known to those skilled in the art, for example, using coupling agents such as carbonyl diimidazole or dicyclohexyl carbodiimide in solvents such as THF or DMF.

The coupled product (18) is oxidized to the corresponding sulfonic acid using oxidants such as peracetic acid, performic acid, m-chloroperbenzoic acid following the general method described by L. Hu et al. (*J. Org. Chem.* 2007, 72, 4543). This oxidation is typically carried out at ambient temperature and takes from about 12 to about 24 hours.

The intermediate N-protected sulfonic acid is deprotected using standard methods. The deprotection method is determined by the protective group used, as is well known in the art. For example, the benzyloxycarbonyl group may be removed under hydrogenolysis condition, suitably using a catalytic transfer hydrogenation method, in solvents including alcohols such as methanol and ethanol.

The deprotected amino sulfonic acid (19) is converted to the N,N-dichloro derivative I using methods known in the art including chlorinating agents such as t-butylhypochlorite, trichloroisocyanuric acid, sodium hypochlorite, N-chloro succinimide, various N-chlorohydantoins, and chlorine gas in a solvent such as water, methanol, methylene chloride and the like. The reaction is carried out at low to ambient temperature for about 2 to about 24 hours.

Alternatively, diamine derivative (20) can be converted into the N,N-dichloroamine derivative of formula I as shown in another non-limiting General Procedure 5.

General Procedure 5

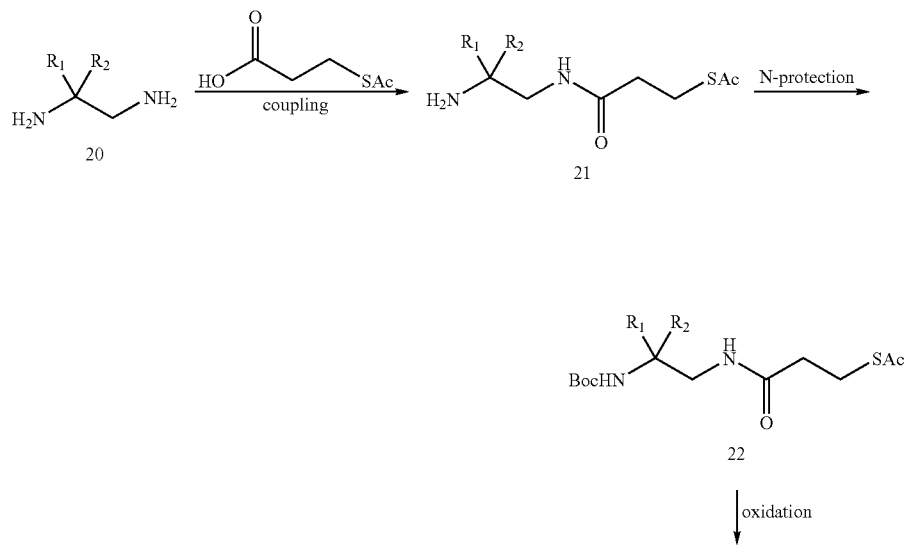

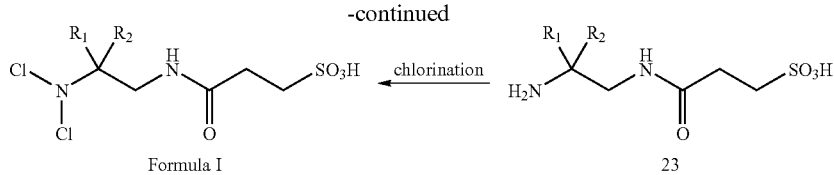

As shown in General Procedure 5, a diamine (20) is coupled with 3-(acetylthio)propanoic acid. The reaction is carried out as described in General Procedure 4. The amino group of the coupled product (21) is protected with groups such as di-t-butyl dicarbonate or benzyloxycarbonyl following conditions well known to those skilled in the art to give compound (22). Typical deprotection conditions depend on the type of protecting group used. For example di-t-butyl dicarbonate group may be deprotected by treatment with an acid such as hydrochloric acid, trifluoro acetic acid, formic acid and the like. The oxidation of the thioacetate functionality in compound (22) and subsequent conversion to the N,N-dichloro derivative I is carried out analogously as described in General Procedure 4.

Further, diamine derivatives (20) can be converted into the N,N-dichloroamine derivative of formula I as shown in another non-limiting General Procedure 6.

As shown in General Procedure 6, a diamine (20) is subjected to selective protection at each nitrogen using two different protecting groups under conditions known in the art. Such selective protection may be carried out in different sequences such that the reactivity at both the primary amines may be utilized in a sequential manner. As shown in General Procedure 6, for example, the protecting groups used are di-t-butyl dicarbonate to yield compound (24), then benzyloxycarbonyl to yield compound (25), using methods known to those skilled in the art.

The amino compound (26), prepared by the deprotection of compound (25), can be transformed to the N-formylated compound (27) by reaction with formic acid under standard peptide coupling conditions using solvents such as THF or DMF. The reaction is carried out at room temperature and is typically completed in about 4 to about 24 hours.

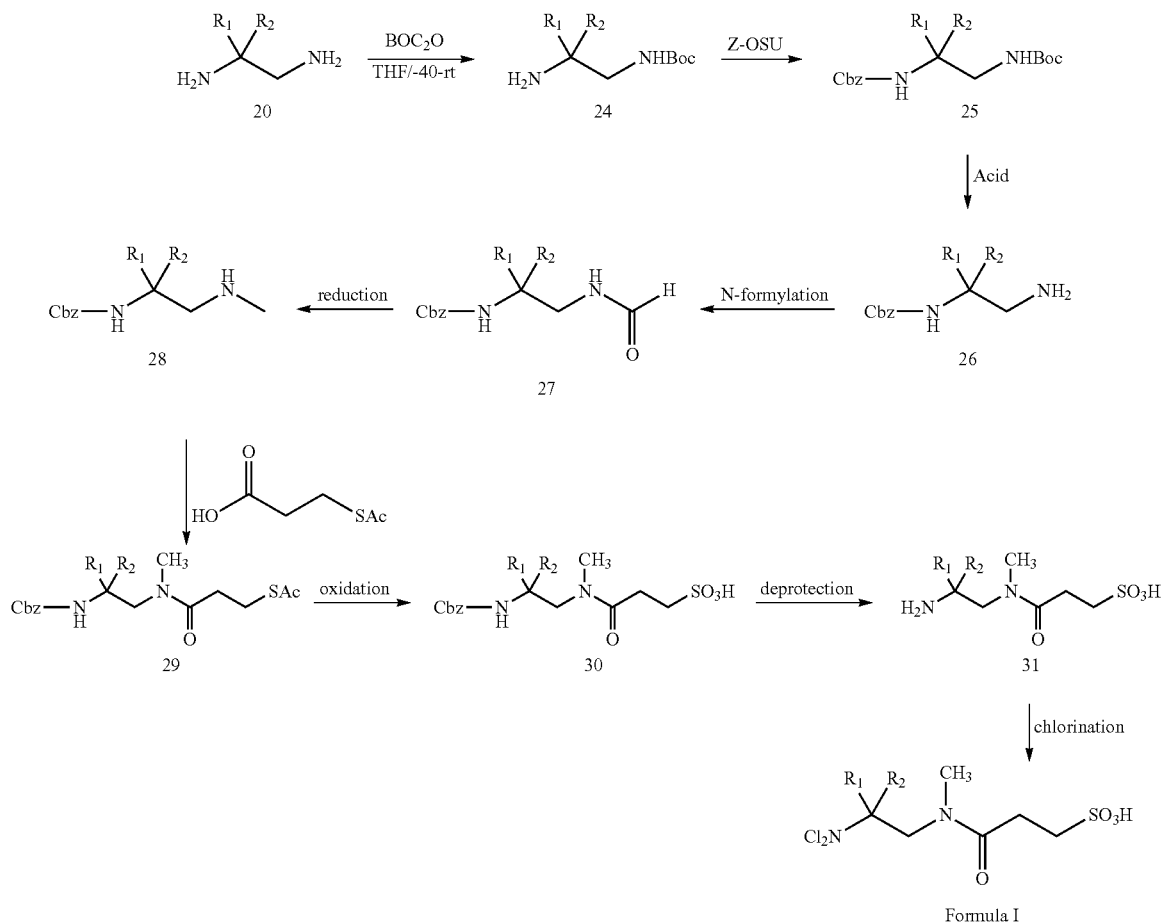

The reduction of the N-formylamine (27) to the N-methylamine (28) is accomplished in the presence of a borane-methylsulfide complex such as borane-dimethylsulfide complex. The reaction is carried out in an inert solvent such as THF. Methanol is added to complete the transformation, which is typically carried out at ambient temperature for about 2 to about 12 hours.

Formation of the amide (29) is accomplished by reaction of amine (28) with 3-(acetylthio)propanoic acid in the presence of 1,1'-carbonyldiimidazole in a solvent such as acetonitrile, DMF or THF. The reaction is typically carried out at reflux temperature for about 2 to about 12 hours. The N-methylamine compound (29) is transformed to the N,N-dichloro derivative I following steps analogous to those described in the General Procedure 4.

Alternatively, N-protected β-amino alcohol derivatives (11) can be converted into the N,N-dichloroamine derivative of formula I as shown in another non-limiting General Procedure 7.

Alternatively, a commercially available acrylic acid (35) can be converted into the N,N-dichloroamine derivative of formula I as shown in another non-limiting General Procedure 8.

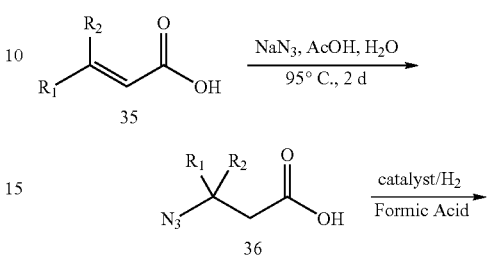

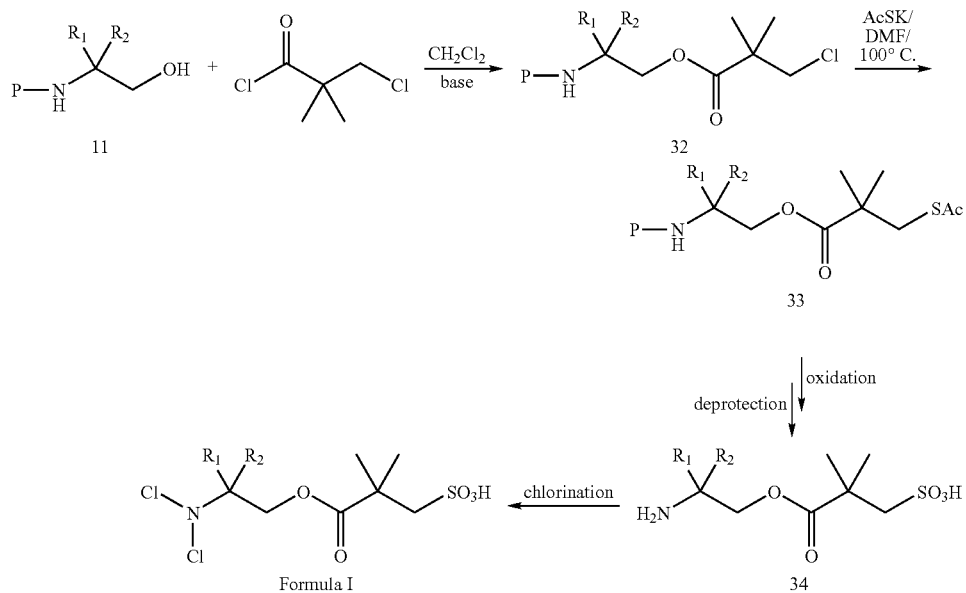

As shown in General Procedure 7, a protected amino alcohol (11) is esterified with chloropivaloyl chloride, which is commercially available, to yield compound (32). The esterification is done in an inert solvent such as methylene chloride in the presence of an organic base such as triethylamine, diisopropylethylamine and the like. Typically, the reaction is carried out at 0° C. to ambient temperature.

The ester intermediate (32) is reacted with potassium thioacetate to afford the thioacetate analog (33). This reaction is a typical nucleophilic substitution reaction well known to those skilled in the art. A polar aprotic solvent such as DMF is generally used. The reaction is carried out at ambient to reflux temperatures depending on the substrate reactivity until the reaction is completed as determined by methods well known to those skilled in the art.

The conversion of the thioacetate (33) to the N,N-dichloro derivative I is analogous to that described in General Procedure 4.

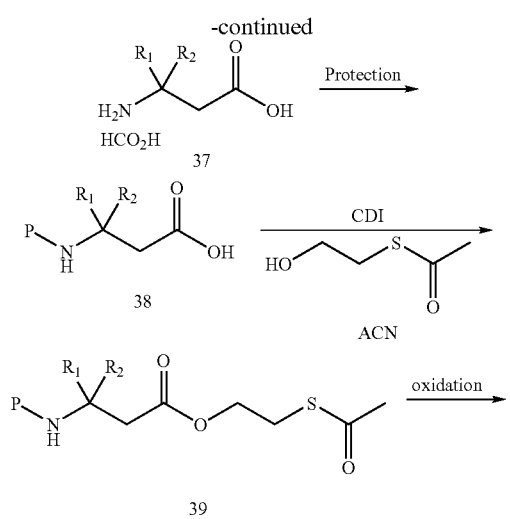

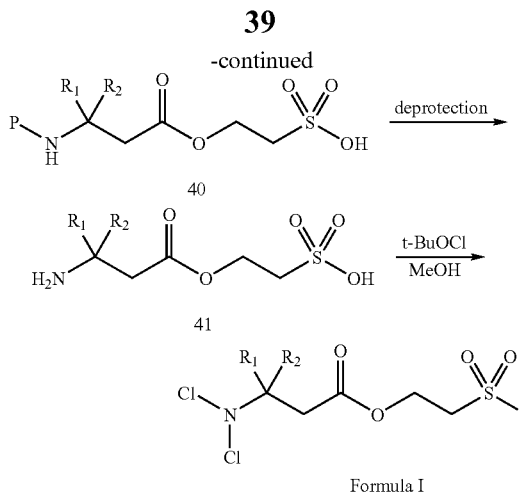

Formula I

As shown in General Procedure 8, the azido-carboxylic acid (36) can be synthesized following the method of Nagarajan and Ganem (*J. Org. Chem.* 1986, 51, 4856.) utilizing a commercially available 3,3-disubstituted acrylic acid. The reaction typically requires elevated temperatures for about 24 to about 72 hours.

The azide function of compound (36) is reduced in the presence of a transition metal catalyst such as 10% palladium on charcoal to yield amino compound (37). This transformation may also be carried out in the presence of platinum or with other catalytic systems such as Raney nickel. The reaction is carried out in a polar solvent such as formic acid, acetic acid or dimethylformamide, at ambient temperature and at atmospheric pressure in the presence of hydrogen.

N-Benzyloxycarbonyl protection of the amino group of compound (37) is accomplished by a suitable agent such as N-(benzyloxycarbonyl)succinimide in the presence of an inorganic base such as sodium hydroxide to yield compound (38). The protection of the amino function can also be carried out with other protecting agents such as di-t-butyldicarbonate [(BOC)$_2$O] or 9-fluorenylmethyl chloroformate (FMOCCl) and other bases such as TEA, diisopropylethylamine (DIPEA) or potassium hydroxide and the like. Suitable solvents for this reaction include methanol and THF, as well as mixtures of solvents including a mixture of methanol, THF and water. The combination of solvents can be adjusted by one skilled in the art to achieve the desired amino protection depending on the chosen protecting agent. The reaction temperature is usually from about 0° C. to about room temperature for about 4 to about 24 hours.

The coupling of compound (38) to S-2-hydroxyethyl ethanethioate to yield compound (39) is carried out using reagents and conditions which are well known to one skilled in the art. For example, coupling agents such as carbonyl diimidazole or diisopropylcarbodiimide can be utilized in solvents such as THF or DMF. The synthesis of the S-2-hydroxyethyl ethanethioate shown in General Procedure 8 is carried out with equimolar amounts of commercially available iodoethanol and potassium thioacetate in methanol at 60° C. for 1 hour. Procedures to obtain analogous compounds may use any available 2-haloethanol and react it with a sodium or lithium salt of thioacetic acid in solvents such as DMF or acetone at elevated temperatures of about 50 to about 80° C. for about 1 to about 8 hours.

The transformation of thioacetate (39) through intermediates (40) and (41) may be achieved following a procedure analogous to General Procedure 4.

Further, N-protected β-amino alcohol derivatives (11) can be converted into the N,N-dichloroamine derivative of formula I as shown in another non-limiting General Procedure 9.

General Procedure 9

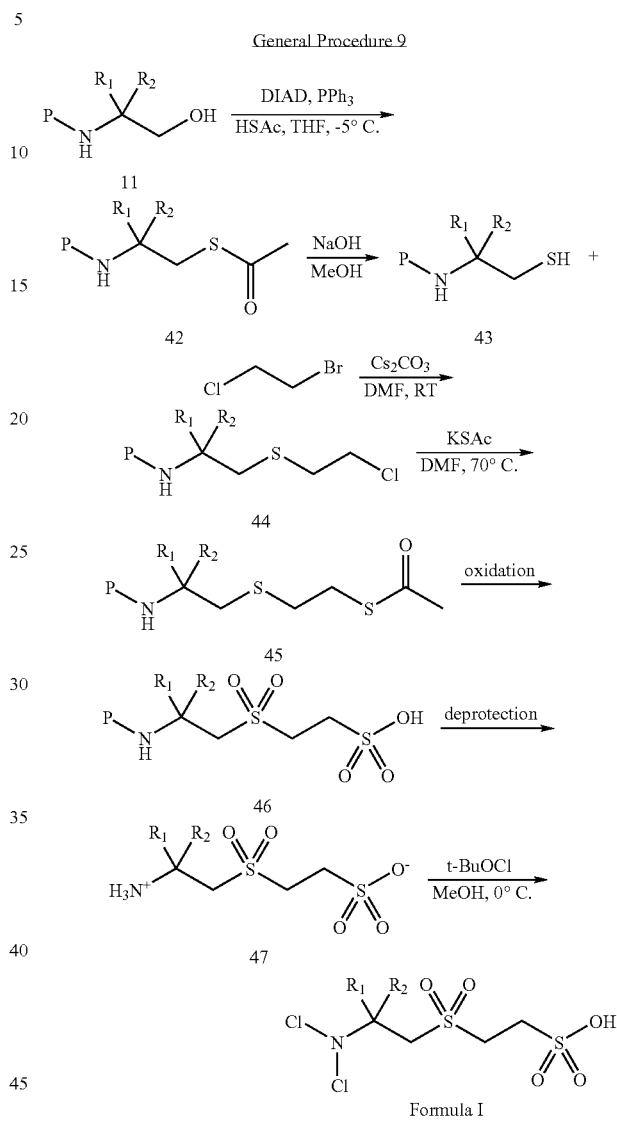

Formula I

As shown in General Procedure 9, the protected β-amino alcohol, (11) (where P is a suitable N-protecting group such as benzyloxycarbonyl or t-butyl dicarbonate) may be transformed into thioacetate (42) using a Mitsunobu reaction according to the method of Bach et al. (*J. Org. Chem.*, 1998, 63, 1910). These reaction conditions require the formation of a betaine adduct between DIAD and PPh$_3$ prior to the addition of alcohol (11) and thioacetic acid at −5° C. in THF. The Mitsunobu reaction can be carried out with diethyl azodicarboxylate or di-t-butyl azodicarboxylate or other di-substituted azodicarboxylates as well as other trisubstituted phosphines such as tri-n-butylphosphine or a water-soluble tris (dimethylamino)phosphine. The reaction occurs under mild conditions (−5° C. to RT) and tolerates a variety of functional groups. The solvents are typically nonpolar since they accelerate the reaction, thus THF, diethyl ether and methylene chloride are preferred solvents, although acetonitrile and DMF can be used.

The hydrolysis of compound (42) to yield compound (43) requires the presence of an aqueous inorganic base, such as sodium hydroxide or potassium hydroxide, for about 15 minutes to about an hour at room temperature. Any inorganic base can be utilized in this reaction in a solvent such as methanol or ethanol. As the thiol function has a high propensity to form disulfide in the presence of oxygen, care must be taken to utilize an inert atmosphere such as nitrogen during the reaction and reduce the thiol to excessive exposure to the atmosphere during workup and isolation.

The thiol (43) is reacted with 1-bromo-2-chloroethane to form the sulfide intermediate (44). This reaction is a nucleophilic substitution as well known to one skilled in the art. Polar aprotic solvents such as DMF accelerate the rate of reaction and are typically used in a temperature range, depending on the substrate, from room temperature to reflux. As shown in General Procedure 9, the bromine atom is more reactive and is selectively displaced at room temperature in DMF. The base utilized to form the nucleophile (RS−) also has an affect on the rate of reaction. For example, cesium carbonate may be utilized to facilitate selective reaction at the bromine-carbon bond. Since large cations are more easily dissolved into polar aprotic solvents, potassium and cesium inorganic base are preferred in nucleophile substitution reactions. The hindered organic bases such as DBU or DIPEA may also be utilized in this type of reaction.

Transformation of the sulfide intermediate (44) through compounds (45) and (46) to (47) is carried out analogously to the methods described in General Procedure 4.

Alternatively, N-protected β-amino alcohol derivatives (11) can be converted into the N,N-dichloroamine derivative of formula I as shown in another non-limiting General Procedure 10.

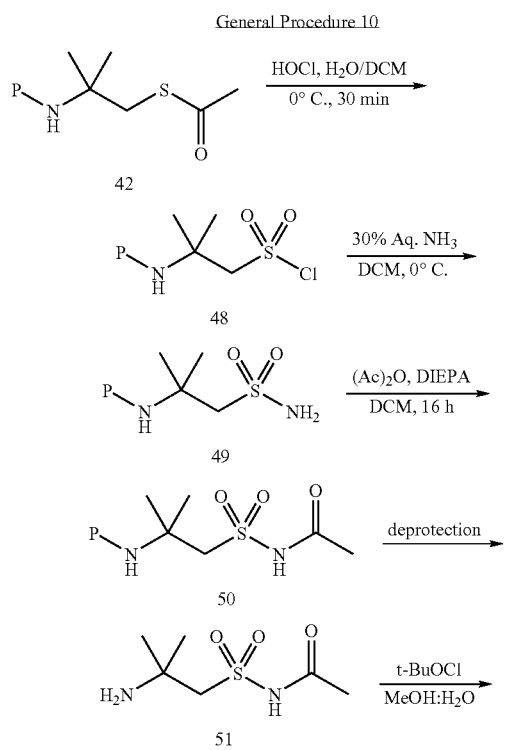

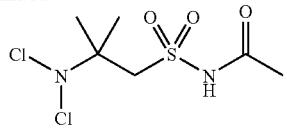

Formula I

The formation of thioacetate (42) has been described in General Procedure 9. As shown in General Procedure 10, compound (42) is oxidatively chlorinated with HOCl in DCM at 0° C. to form the intermediate sulfonyl chloride (48) under mild conditions and in good yield utilizing a modified method from Wright and Hallstrom (*J. Org. Chem.* 2006, 71(3), 1080.) Other reaction combinations such as acetonitrile, water, N-chlorosuccinimide and HCl have been utilized by Nishiguchi et al. (*Synthesis*, 2006, (24), 4131) to obtain sulfonyl chlorides from thioacetates under mild conditions in high yield. Hill et al. (*J. Org. Chem.* 2006, 71(21), 8190) also react thioacetate with HOCl generated from bubbling chlorine gas into a mixture of water and DCM to form sulfonyl chlorides.

The reaction of sulfonyl chlorides with amine nucleophiles are well known to one skilled in the art. A dry inert atmosphere is not required for this reaction as the nucleophile, ammonia was dissolved in water. The reactivity of amines especially ammonia is an order of magnitude more reactive than water. The reaction may have been completed successfully with gaseous ammonia to improve the yield.

The acetylation of compound (49) to yield compound (50) is done with acetic anhydride in the presence of a DIPEA at low temperature under an inert atmosphere. This reaction may also be carried out with acetyl chloride and other organic bases such as pyridine or TEA or aqueous inorganic base if desired. Exact conditions may be determined by methods known to one skilled in the art.

The deprotection of (50) to yield compound (51) and the chlorination of (51) to give the N,N-dichloroamine derivative of formula I follows methods similar to those discussed in General Procedure 4.

Further, the cycloalkene (52) can be converted into the N,N-dichloroamine derivative of formula I as shown in another non-limiting General Procedure 11.

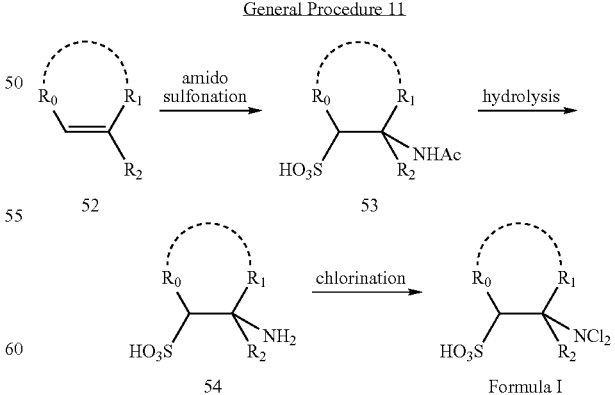

As shown in General Procedure 11, the appropriate commercially available alkene (52) is subjected to amido sulfonation as described by F. M. Cordero et al. (*Eur. J. Org. Chem.* 2002, 1407) to yield compound (53). This reaction is typically carried out by treating the alkene with a sulfur trioxide source such as its complex with DMF, triethylamine or pyridine in acetonitrile as solvent.

The amido sulfonic acid (53) is subjected to acid hydrolysis using a protic acid such as hydrochloric acid or sulfuric acid to give the free aminosulfonic acid (54). This reaction is typically carried out at high temperatures from about 100° C. to about 150° C. for about 12 to about 24 hours.

The chlorination of the aminosulfonic acid (54) is carried out in analogous manner as detailed in General Procedure 4 to give the N,N-dichloroamine derivative of formula I.

A number of the starting materials for the above General Procedures are commercially available, for example, from Sigma-Aldrich Chemical Co. (Milwaukee, Wis., USA), Bachem (Torrance, Calif., USA), Toronto Research Chemicals (North York, ON, Canada), Anaspec (San Jose, Calif., USA), Chem-Impex International (Wood Dale, Ill., USA), Spectrum (Gardena, Calif., USA), PharmaCore (High Point, N.C., USA).

The further non-limiting halogen sources may be used to produce the N-halo or N,N-dihalo amino compounds and their derivatives: bromine itself, N-haloarylsulfonamide salts, wherein the aryl group contains from 6 to 15 carbon atoms with 1 or 2 aromatic rings, 6 to 10, or 6 to 8, carbon atoms and one aromatic ring, such as N-halobenzene-sulfonamide or N-halo-4-alkylbenzenesulfonamide, wherein the alkyl group is lower alkyl from 1 to 4 carbons, methyl or ethyl. The N-halobenzene-sulfonamides or N-halo-4-alkyl-benzenesulfonamides are often used in the form of their salts, for example, alkali salts, for example, their sodium or potassium salts. In this group the most frequently used reagents will be N-chlorobenzenesulfonamide and N-chloro-4-methyl-benzenesulfonamide in form of their sodium salts, because they are readily commercially available. Other non-limiting halogen releasing agents or sources may be HOCl, N-chloro-succinimide or N-bromosuccinimide, N-iodosuccinamide, or combinations of the agents.

If one molecule of the halogen source releases one halogen, obviously for each starting amine of the amino acid or derivative molecule at least one or two molecules of the halogen source will be used to achieve the desired halogenation. More details of the preparation of N-halo or N,N-dihalo amino acids and their derivatives are set forth in the examples.

When not commercially available, the phosphonic acid starting materials for the preparation of the compounds of the present application may be also prepared according to procedures well known to one skilled in the art. See for example Yuan, C. et al., "New Strategy for the Synthesis of Functionalized Phosphonic Acids," *Heteroatom Chem.* 1997, 8 (2) 102-122; Yuan, C., et al., "New strategy for the Synthesis of Functionalized Phosphonic Acids," *Pure Appl. Chem.* 1996, 68(4), 907-12; "A Versatile Route to Substituted Organophosphonic Acids", *J. Am. Chem. Soc.,* 1990, 31, 2933; G. M. Kosolapoff, "The Synthesis of Phosphonic and Phosphinic Acids," *Organic Reactions*, Vol. 6, 1951, and references cited therein, the disclosures of all of which are incorporated by reference herein in their entirety.

Compounds according to the present application can also include their individual stereoisomers (enantiomers and diastereoisomers) as well as the racemic mixtures of the compound. The individual isomers, such as the pure R, S, RR, SS, RS, SR, etc., may be prepared by treating the isomeric mixture with an optically active resolving agent to form a pair of diastereoisomeric compounds. The diastereoisomeric compounds may be separated and the optically pure enantiomer or diastereomer may be isolated using procedures well known in the art. Because diastereomers have distinct physical properties (such as the melting points, boiling points, solubilities, reactivity, etc.), they can be readily separated by taking advantage of these dissimilarities. The diastereomers can be separated by chromatography or, preferably, by separation or resolution techniques based upon differences in solubility. A more detailed description of the techniques applicable to the resolution of stereoisomers of compounds from their racemic mixture can be found in Jean Jacques Andre Collet, Samuel H. Wilen, *Enantiomers, Racemates and Resolutions*, John Wiley & Sons, Inc. (1981) and references cited therein.

Derivatives of the N-monohalo- and N,N-dihalo-amino compounds may be prepared by protecting the amino group with an amino-group protecting agent as disclosed herein, for example, by forming the benzyloxycarbonyl (CBZ) derivative, followed by the formation of the sulfonyl chloride which may be converted into sulfonamides, for example with a lower alkyl amine, such as methylamine. Similarly, the sulfonyl chloride may be reacted with benzylamine, and the resulting benzylsulfonamide may be converted to the group —$SO_2NH_2$. Thereafter the protecting group may be removed by methods known per se to chemists skilled in the art. A comprehensive list of suitable protecting groups that may be used may be found in T. W. Greene, *Protecting Groups in Organic Synthesis,* 3rd edition, John Wiley & Sons, Inc. 1999, the disclosure of which is incorporated herein in its entirety.

Pharmaceutically acceptable salts of the compounds of the present application may be prepared by reacting the free acid or base forms of these compounds with a stoichiometric or greater amount of the appropriate base or acid in water or in an organic solvent, or in a mixture of the two; generally, for example, non-aqueous media like ether, ethyl acetate, ethanol, isopropanol. The salts of the present application may also be prepared by ion exchange, for example.

Salts may also be prepared by reacting the N-halo- and N,N-dihaloamino compounds in other manners known per se including a method analogous to the method described in German Patent Application 4041703 W. Gottardi, the disclosure of which is incorporated herein in its entirety.

The sodium salts of the N-halo- or N,N-dihaloamino compounds may be converted into the lower alkyl esters by reacting the sodium salt with a lower dialkyl sulfate, such as dimethyl or diethyl sulfate in the presence of sodium bicarbonate.

The sulfonamides in which the substituent Z is —$SO_2$—$NH_2$ are produced in a manner well-known to chemists skilled in the art.

Methods of Use for Compounds of the Application

The N-halo- or N,N-dihaloamino compounds and their derivatives are antimicrobial agents which kill microbes at relatively low concentrations and can be tolerated by eukaryotic cells at significantly high concentrations. In the preferred N-halo- or N,N-dihaloamino compounds, halo is chloro. This range of therapeutic activity and favorable therapeutic index is absolutely critical considering the physiological role of chloramines in the destruction of pathogens in vivo. For an antimicrobial product that is applied to vital, soft and sensitive tissues such as ophthalmic, skin or any other sensitive areas its safety and efficacy cannot be compromised. Thus, use of such product(s) in humans for treating infections is supported by our positive results.

The compounds of formulae I-VII or their derivatives have the following areas of application: contact lens cleanser, bacterial inactivation, ophthalmic, general surgical preparation including oncology, surgical instrument disinfection, medical device and instrument disinfection, dental instruments disinfection and application in food sanitation including disinfection of surface areas. They are also useful in vaccine formulations (as preservative and potentially adjuvant), as compounds with viricidal effect, for the viral inactivation of both DNA and RNA classes of viruses including HIV, hepatitis A, respiratory syncytial virus, Adenovirus, West Nile virus, HSV-1, HSV-2, SARS, influenza and para-influenza viruses, picornaviruses, and vaccinia virus (as a Model for Poxviruses). In addition, these compounds are also useful for the treatment of fungal infections, such as acute or chronic *Rhinosinusitis* or other fungal infections such as *Otitis, Dermatitis, Bronchitis, Pneumonia's* such as *Pneumocystis carinii*, the fungal infections of sex organs, such as *Colpitis, Endometritis, Balnitis*, fungal infections of the gastrointestinal tract, such as *Stomatitis, Oesophagitis, Enteritis*, or fungal infections of the urethra, such as *Pyelonephritis, Ureteritis, Cystitis*, or *Urethritis*. Furthermore, the compositions described herein have antimicrobial activity against many other microorganisms, including *H. influenzae, Escherichia coli, E. faecium, E. faecalis, Listeria monocytogenes, Staphylococcus aureus*, methicillin-resistant *S. aureus* (MRSA), *S. epidermidis, S. pneumoniae, Pseudomonas aeruginosa, P. mirabilis, K. pneumoniae, Lactobacillus, A. junii*, yeast, including *Candida albicans*, vancomycin-resistant *enterococcus*, molds, and spores, including spores of anthrax and cysts of Acanthamoeba. In particular, the solutions of the present application may be useful in the treatment of several different strains of *Bacillus anthraces*. Vancomycin-resistant bacteria, MRSA, and others are easily destroyed by the compositions of the present application. Examples of bacteria implicated in periodontal disease and destroyed by the compositions of the present application are *Bacteriodes gingivalis, B. intermedius, Actinomyces actinomycetemcomitans* and *B. forsythus*. Examples of bacteria that are implicated in mastitis (infection of cow udder) and killed by the compositions are *Streptococcus agalactiae* and *Streptococcus infantarius*. The compositions destroy biofilms and are therefore effective against microbes growing in both planktonic form and in biofilms.

In a further aspect of the present application, there is provided a method for the treatment of various medical conditions selected from the groups consisting of promoting wound healing, reduction of pathogens in open wounds, wound decontamination, wound bed irrigation/preparation, ocular disinfection or decontamination, oral disinfection, nasopharyngeal therapy, antifungal therapy, ophthalmic, oral surgery and dentistry, otology applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis or other diseases that produces biofilms, treatment of viral infections, treatment of skin diseases, and tissue repair and regeneration, which method comprises using the solution of the present application by applying the solution to the site where treatment is required such as pre- and post-operative surgery, cardiovascular, re-secting solid tumor in oncology.

As an example, the dosage for use on chronic wounds of an approximate size of 25 square cm may be in the range of 30 mL of solution containing 2 to 200 mg of an N-halo- or N,N-dihaloamino compound. Compounds that may be used include 3-(4-chlorophenyl)-2-(dichloroamino)-2-methylpropane-1-sulfonic acid or any other halogenated amino compound described herein or a derivative thereof. The solution may be applied from one to ten times per day or as deemed necessary for effectively treating the wound. In certain instances the composition may contain about 0.01 mM to about 1 M, or about 0.1 to about 100 mM of N-halo- or N,N-dihaloamino compounds. In certain variations of the composition, one or more of N-halo- or N,N-dihaloamino compounds may be used. Dosages in other applications would be adjusted to the local area depending on where the antimicrobial activity is required and the severity of infection.

The Compositions of the Application

In one aspect the compositions in form of solutions are osmotically balanced, and have minimal mammalian cytotoxicity. In another aspect, the compositions are not osmotically balanced and have minimal mammalian cytotoxicity. In another aspect the compositions described herein have a therapeutic index of about 20 to about 5,000.

Because the compositions of the present application are substantially nontoxic to mammals and have antibacterial properties, they are useful in any application in which antimicrobial properties are desirable. Such applications include, without limitation, treatment of wounds, burns, and canker sores; irrigation; the treatment of various fungal infections such as onychomycosis (fungal nail infections on fingers and toes) cleaning of tissue sites (e.g., pre- and post-operative); ophthalmic applications (e.g., in contact lens cleaning solutions or for irrigation of the eye before, during, or post ophthalmic surgery); for nasal or nasopharyngeal applications including, but not limited to, the treatment of rhinosinusitis or rhinitis caused by viral, bacterial or fungal infections; for dermatological applications, facial cleansing of microbial infection, cold sore, pimples, psoriasis; and numerous applications which are readily apparent to one skilled in the art, such as dental applications including the treatment of gingivitis or periodontitis, and animal health applications (including treatment of mastitis). Application also includes the elimination or reduction of pathogens on surfaces including medical equipment, instruments, organ preservation, implant disinfection, devices or food (without limiting to meat, fruits, vegetables) and food contact surfaces including the elimination or reduction bacterial biofilms. Unlike many anti-infective compositions used in similar applications, the compositions of the present application have minimal to no side effects.

The compositions of the present application which comprise N-halo- or N,N-dihaloamino compounds of the formulae I-VII and their derivatives may be incorporated into a variety of applications, including bandages or wound dressings. The compositions in form of physiologically balanced, acidic solutions may be used in combination with specially designed bandages in a wound treatment protocol. The specialized bandage may include an opening or "window" through which topical treatment materials such as the solution of the present application may be applied. The compositions may also be applied in applications (for example treatment of burns) where it is desirable to maintain a moist and sterile environment without disturbing the dressing. In one such example a perforated tube is placed between the dressing and the outer bandage or wrap. Periodically the composition is passed through the tube thus irrigating the dressing with fresh antimicrobial solution.

Also disclosed herein is an article of manufacture comprising the composition of the present application packaged in a container. Surfaces of the container which are in contact with the composition of the present application are made of material which is not reactive with an oxidizing agent.

The stability of a solution of N-halo- and N,N-dihaloamino compounds and their derivatives permits the use of different forms of packaging that would be practical for use by patients. The solution may be packaged in several single-use 20 to 40 mL or 30 mL clear or amber glass bottles with Teflon-lined screw caps and sealed with tape to ensure gas tightness. In one aspect, the same solution may be packaged in a 250 mL amber glass bottle or in a 250 mL non-reactive plastic bottle. However, up to 5 liter bottles may be used, because such larger volumes are practical for treatment of burns. Storage in these receptacles ensures long-term stability required for the uses of the compositions described herein in detail. A solution containing a compound described herein within the concentration range described herein in a vial stored in a refrigerator has a loss of no more than 10% at time t=0 after a period of three months. Additionally, packaging may include a dual chamber system where component A is mixed with component B to form the final product, N,N-dihaloamino compound or its derivatives. The N-halo- and N,N-dihaloamino compounds may be used in appropriate concentrations and delivery vehicles or carriers that are non-irritating and suitable for delivering the active compound to the intended site of action, such as lotions, solutions, creams, emulsions, ointments, balms, pastes, sprays, aerosols, gels, patches, solids, sticks, aqueous solutions, organic solvents, or other foundation compositions. Generally, such carrier systems can be described as being solutions, creams, emulsions, gels, solids and aerosols. Delivery may also include special means for delivery, such as a pessary or suppository. The compounds may also be incorporated as active agents or inactive precursors into or onto medical devices, such as catheters, stents, pace makers, needles or tubings.

In one aspect, the solutions of the present application may be stored in single-use containers. In another aspect, the solutions of the present application may be stored in single-use containers of various different sizes, configurations, and having different volumes as suitable for the desired applications as disclosed herein. In some applications, for example, the solution of the present application may be stored in single-use 30 mL, optionally disposable containers. In one aspect the present composition may be stored as powder together with pharmaceutically accepted excipients, optionally under inert gas, at room temperature.

The compositions of the present application may include the following pharmaceutically acceptable carriers: sodium chloride to attain isotonicity, buffers, stabilizers, solvents, flavoring agents (in case of oral or nasopharyngeal administration and food industry), preserving agents, diluents, extenders and other auxiliary substances or excipients. Specific examples of pharmaceutically acceptable carriers and excipients that may be used are described in *Remington: The Science and Practice of Pharmacy*, A. Gennaro, ed., 20th edition, Lippincott, Williams & Wilkins, Philadelphia, Pa.; *Advances in Pharmaceutical Sciences* (David Ganderton, Trevor Jones, Eds., 1992); *Advances in Pharmaceutical Sciences*, Vol. 7 (David Ganderton, Trevor Jones, James McGinity, Eds., 1995), the disclosures of which are incorporated herein in their entirety. In general, water, a suitable oil, saline, lower alcohols, and glycols such as propylene glycol or polyethylene glycols may be suitable carriers for solutions. In one aspect solutions contain the active ingredient in a water soluble or aqueous medium soluble form, for example as a salt, together with suitable stabilizing agents, and if necessary, buffer substances. In addition, solutions may contain preservatives, such as benzalkonium chloride, methyl- or propyl-paraben, and chlorobutanol.

The compositions may further comprise other active ingredients, such as HOCl or other antibacterials as long as they do not interfere with the stability or function of the N-halo- or N,N-dihaloamino compounds of the present application.

The amounts or concentrations of N-halo- or N,N-dihaloamino compound in the compositions of the present application may vary over broad ranges. For example, a composition may contain from about 0.001 to about 100% by weight of the composition of the N-halo- or N,N-dihaloamino compound. In case of about 100%, the composition may be applied in the form of a powder without any carrier substance. A typical range of the composition include about 0.1 to about 95% by weight of the composition of the N-halo- or N,N-dihaloamino compound, for example, about 0.1 to about 50%, or about 0.1 to about 10%, for example, about 0.5 to about 5%. In solutions, usually a lower concentration of the N-halo- or N,N-dihaloamino compound may be applied. For example, a concentration of 1 to 2% may be appropriate in case of a rinse or spray. In another range, the concentration of the compound or its derivatives may be about 0.01% to about 20% of the composition by weight.

In case of nasopharyngeal application a catheter for nasal application containing a about 0.5 to about 5%, for example a 1% solution of the N-halo- or N,N-dihaloamino compound or its salt with a pH of about 2 to about 8, preferably about 3.5 to about 5 may be used for several weeks using about 5 to about 50 mL, for example, 10 to 15 mL of the solution for each treatment. After each treatment, the rinsing solution may be removed, such as by absorbing with gauze, rinsing with water or saline or by suction.

The present application includes pharmaceutical compositions that comprise at least one halogenated compound. The halogenated compound is selected from a N-halogenated or N,N-dihalogenated compound described herein or a derivative thereof. More specifically, such compositions include a N-halogenated or N,N-dihalogenated derivative of formulae I-VII or a derivative thereof. In one aspect, the halogenated compound is an alkaline metal hypohalide, such as sodium hypochlorite, but more preferably a hypohalous acid, most preferably hypochlorous acid. These binary pharmaceutical compositions have anti-inflammatory, immuno-modulatory, bactericidal, antibacterial, anti-infective, antimicrobial, sporicidal, disinfectant, antifungal and antiviral effect and tissue healing stimulation without exhibiting substantial stimulation of myeloperoxidase activity in a mammal. The hypochlorite titer of these pharmaceutical compositions is below or equal to 1 mole/liter (1 M) of available chlorine, particularly of a hypochlorite of an alkaline metal, especially sodium hypochlorite or hypochlorous acid. Its minimum titer is greater than or equal to about 1 picomole/liter. The N-chloramine or N,N-dichloroamine titer of these compositions is less than or equal to about 5 moles/liter (5 M) with a minimum of 0.01 femtomoles/liter.

The binary compositions of the present application may be combined with excipients or carriers that are appropriate for a particular use. For liquid compositions water is a preferred excipients or carrier, although other non-oxidizable compatible carriers may also be used. Some aqueous compositions may contain osmotic (isotonic) purified water. Other compositions do not require osmotic balancing. The aqueous compositions may also contain diverse agents that are compatible with the halogenated compound and the N-halogenated or N,N-dihalogenated derivative of at least of a compound selected from compounds described herein, as well as compatible with the use to which the composition will be put. If the compositions are destined for a pharmaceutical use and administration to humans or animals, the excipients or carriers must be pharmaceutically acceptable, such as substantially non-toxic and not interfere with the intended use of the pharmaceutical compositions. The skilled person will be aware that the characteristics of the composition can be varied or modified. Such modification can be effect with regard to stability, for example, by including stabilizers; with regard to pH by including pH adjusting agents, such as buffers, bases or acids; with regard to density by agents that influence density, for example diluents that reduce density or by density-increasing agents that that have a higher density than water; with regard to solubility by adding solubilizers; with regard to viscosity by adding agents that will affect viscosity, either by increasing it, for example by adding biocompatible polymers, or by reducing it by adding agents that have a low viscosity profile; with regard to coloring by adding compatible dyestuffs or coloring agents that are not oxidized by the binary halogenated components; with regard to wetting properties by adding appropriate surface-active agents or surfactants; with regard to olfactory or gustatory properties of the binary compositions by adding agents that display an attractive smell or flavor, for example, to facilitate use of the compositions for certain uses or users.

The preparation of the binary composition depends on its form, whether it is in solid, liquid or gaseous form. Solid compositions may be in form of a powder, or gel. Semisolid compositions may be in form of an ointment or cream. Liquid compositions may be in form of a solution, emulsion or suspension or an oil. Gaseous compositions may be in form of an aerosol. Details for such preparations for pharmaceutical uses can be found in Remington; details for such preparations for consumer products can be found in *The Chemical Formulary*, H. Bennett Ed., Chemical Publishing Company (1998), vol. XXXIV.

Specific Methods for Using Compositions of the Application

In one aspect, the compositions of the present invention are administered or used topically. The formulations of compounds of the present invention may be used in treating a number of patients with deep wounds, which do not respond to usual medications and locally applied treatments. In one aspect, the present invention provides a method for the treatment of various medical conditions such as promoting wound healing, reduction of pathogens in open wounds, wound decontamination, ocular disinfection or decontamination, oral disinfection, antifungal therapy, ophthalmic applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis and related diseases, treatment of viral infections, treatment of skin diseases, and tissue repair and regeneration, which method comprises using solutions of compounds of the present invention by applying the solution to the site where treatment is required. Non-limiting examples of biofilm that may be treated using the solutions of the present invention include those cited in the review article entitled "*Is there a role for quorum signals in bacterial biofilms?*" by S. Kjelleberg, and S. Molin, PMID: 12057677 (PubMed-indexed for MEDLINE).

The compounds of the present invention or compositions thereof are effective in reducing bacterial load thus improving wound healing. The compositions are well-tolerated, improve the granulation of wound tissue, reduce the need for debridement compared to prior art compositions with patients reporting less pain during their treatment and could potentially dampen the inflammatory response through cytokine regulations. (See: A. Mainnemare et al., "Hypochlorous acid and taurine-N-monochloramine in periodontal diseases", *J. Dent. Res.* 2004, November 83(11):823-31; Review.)

Oral Care

Compounds of the invention may be formulated as solutions, which may be used to treat canker sores (mouth ulcers) or cold sores by rinsing the affected area. For example, such solutions can be used by soaking the cold sore 3-4 times a day, each time with 2-3 applications, and putting the solution in contact with the sore for 20-30 seconds. The solutions may also be used as a mouth rinse for dental and mouth hygiene and to control infection. In this instance, the solution may be used as a gargling solution to fight throat infection. The solution may be applied with the help of a cotton swab for more specific areas. The solution can be used once or several times a day according to a patient's needs and condition.

Dental Equipment Care

The choice of specific cleaning or disinfecting agents of the present invention is largely a matter of judgment, guided by product label claims and instructions and government regulations. A single liquid chemical composition might not satisfy all disinfection requirements in a given dental practice or facility. Realistic use of a liquid composition containing a N-halo- or N,N-dihalo amino compound, optionally in conjunction with an inorganic hypohalous compound, depends on consideration of multiple factors, including the degree of microbial killing required; the nature and composition of the surface, item, or device to be treated; and the cost, safety, and ease of use of the available agents. Selecting one appropriate product with a higher degree of potency to cover all situations might be more convenient.

Dental Care and Hygiene

Periodontal disease is a general term used to describe diseases that affect the gingival and supporting tissue connected to bone and teeth in the jaw. See "Periodontal Disease", Ray Williams, *New England Journal of Medicine*, 322: 373-382, 1990. Gingivitis (an early stage of the disease) and periodontitis are caused by specific bacteria and the host's reaction to the disease. For example, an increase in *actinomyces* and also the presence of *Fusibacterium nucleatum*, species of *lactobacillus, veillonella* and *treponema* has been implicated in causing gingivitis. Adult periodontitis is associated with *Bacteriodes gingivalis, B. intermedius, Actinimyces actinomycetemcomitans* and *B. forsythus*. A number of other species may also participate in active periodontal disease.

Commonly considered, antimicrobial therapy is the use of ingested antibiotics to help fight periodontal (gum) disease which is caused by certain oral bacteria. Typically, ingested antibiotics are used in conjunction with scaling and root planing. Some dentists use antimicrobial therapy only as a last resort, while others use it more frequently. In some cases, antimicrobial therapy can eliminate the periodontal disease. In others, periodontal surgery still is needed. However, the use of the compositions of the present invention formulated for dental applications, referred herein as the "dental compositions", has the key advantage over the use of ingested antibiotics that it does not induce antibiotic resistance, gastrointestinal discomfort or allergic effects, in addition to a general advantage of topical therapy over systemic therapies in that less compound is needed to achieve the same local concentration.

Most people with periodontal disease do not receive antimicrobial therapy. This form of therapy generally is used for certain situations, including:

Necrotizing ulcerative gingivitis (NUG), a rare, aggressive form of periodontal disease that occurs mostly in people aged 15 to 35;

Rapidly progressive periodontal disease;

Periodontal disease that has not responded to other types of treatment;

Patients who have weakened immune systems or other serious medical conditions.

However, because use of the dental compositions of the present invention does not involve treatment with an ingested antibiotic, the dental compositions of the present invention can more frequently be used to control microbial infections or plaque (the collection of bacteria that accumulates on teeth) which may be the cause of dental caries. Although the mouth contains many different bacterial strains, only certain strains appear to cause dental decay. The dental compositions of the present invention are effective against the large number of bacteria found in the mouth, in particular against acid-producing bacteria which are the ones that cause tooth decay, for example, *Streptococcus mutans*. The compositions of the present invention are effective to control or prevent smooth surface decay, pit and fissure decay as well as decay in the enamel. In case a patient has especially active decay-causing bacteria in their mouth, the dentist may prescribe a mouth rinse which includes the dental compositions of the present invention for several weeks to kill off the bacteria that cause tooth decay.

The dental compositions of the present invention are also useful for the co-treatment of pulpitis, a painful inflammation of the tooth pulp, for the treatment of a periapical abscess, which is a collection of pus or cellulitis originating from a bacterial infection. The dental compositions of the present invention may be used in conjunction with antibiotics.

The dental compositions of the present invention are also suitable for the treatment of periodontal diseases caused by accumulation of bacteria, such as gingivitis, herpetic gingivostomatitis caused by viral infection, gingivitis of pregnancy caused by hormonal changes, pericoronitis where the gum swells over a tooth that has not fully emerged or gingivitis of leukemia, or periodontitis, a type of gingivitis extending to the supporting structures of the tooth.

The dental compositions of the present invention may be used in conjunction with professional dental hygiene performed that is either during cleaning of the teeth or pockets using scaling, or after professional care, on patients by dental hygienists. Before choosing the compositions of the present invention, a dentist may decide to take a sample of the bacteria and send it to a lab. The lab grows the bacteria, identifies them, and determines which concentration or formulation of the compositions of the present invention would work best against them. The dentist or periodontist will then use this information to prescribe the dental composition that is most effective for the infection. However, because the dental compositions of the present invention are so effective in killing the bacteria effecting dental diseases, this step often may be omitted.

Therapy for periodontal disease can be given systemically or locally. Local therapy is given in the dentist's chair, and involves placing the dental composition directly into the affected parts of the mouth. There are several types of local therapy, including:

- Gel—The dentist injects a gel containing the compositions of the present invention under the gums. The area is sealed and covered with a special bandage to prevent leakage. After seven to 10 days, the dentist removes the bandage and any remaining gel.
- Chip—The dentist places a chip containing a dental composition containing the N-halo- or N,N-dihalo amino compounds under the gums. The chip dissolves over seven to 10 days.
- Powder—The dentist squirts a powder containing the compositions of the present invention under the gums. The powder dissolves over a three-week period.
- Ribbon—The dentist places a floss-like fiber under the gums that slowly releases N-halo- or N,N-dihalo amino compounds. The ribbon is removed after about 10 days.
- Microspheres—The compositions of the present invention are formulated in compatible carrier materials as bioerodible or biodegradable microspheres, microparticles or microcapsules that are placed in the gum pocket and slowly release the compositions. The carrier polymer should be substantially resistant against the N-chloro or N,N-dihalo amino compounds and dissolve over time. Examples of such polymers can be found in an article by J. C. Middleton, A. J. Tipton in *Medical Plastics and Biomaterials Magazine*, March 1998, p. 30.

Antimicrobial therapy usually lasts one to two weeks. Once the dentist has decided on using the composition comprising N-halo- or N,N-dihalo amino compounds, for example, the patient first will undergo scaling and root planing. This procedure removes plaque and calculus (tartar) from under the gum line and smoothes any bumps or irregular areas on the tooth roots, where plaque can easily accumulate. After scaling and root planing, the dentist may prescribe some type of local antimicrobial therapy.

Dental Aftercare

The dentist will recheck a patient after two or three months to see if the therapy is effective. If the disease does not respond to treatment with the composition comprising N-halo- or N,N-dihalo amino compound, the next step will depend on several factors, including the severity of the disease. The dentist can prescribe an ingested antibiotic or schedule periodontal surgery. Some patients may receive several rounds of treatment of N-halo- or N,N-dihalo amino compounds before their disease responds. Others need to be on long-term antibiotic therapy to keep their disease under control. Once a patient has undergone successful treatment for periodontal disease, it is important to help prevent recurrence. Impregnated dental floss may also be used after a visit with the dentist to provide continuous contact of the affected areas with the N-halo- or N,N-dihalo amino compound compositions. Maintenance therapy involves regular visits to the dentist or periodontist; this is usually every two to four months for people treated for periodontitis and every six months for people treated for gingivitis.

The dental compositions of the present invention have the benefit that they avoid the risks of ingested antibiotic therapy, such as antibiotic resistance or an allergic reaction to the antibiotic medication or adverse reactions (such as rash, hives or stomach upset). As with other types of infections, inappropriate use of ingested antibiotics can lead to organisms becoming resistant to the effects of these medications. As part of preventive therapy the patient may use the compositions as a solution for oral rinse or direct application to gums (pockets) using an applicator.

Ophthalmic Care

A physiologically balanced, acidic solution of compounds of the present invention may be used in place of a saline solution to remove a foreign body from, to rinse, or to irrigate the eyes. It can also be applied topically before or after surgery to disinfect an eye and surrounding tissues. The solution can be used once or several times a day according to a patient's needs and condition. The solution can be applied by dropping it directly into the eyes as necessary. It can also be applied by soaking a gauze and applying the saturated gauze to the eyes for one or several minutes. It can also be used to clean the eyes by gently wiping the eyes with saturated gauze. The solution can also be poured into a small eye washer, then the washer is inverted over the eye and the eyelid opened and closed several times.

The physiologically balanced, acidic solution of compounds of the present invention may be used for the treatment of ocular disinfection or decontamination. In addition, it may be used as a replacement for silver nitrate in the disinfection of the eyes of neonates.

The solutions of compounds of the present invention may be used for the cleaning eyes in adults and in pediatrics. For example, various viral infections, bacterial or fungal infections, or pathogenic agents may be effectively treated with a solution of compounds of the present invention. Non-limiting examples of pathogenic agents that could be successfully treated with the solution of the present invention include *Chlamydia trachomatis*, gonorrhea as well as other bacterial, fungal, and viral infections. The compositions of the present invention may be used especially for pre- and post-operative disinfection.

The reader will see that a solution of compounds of the present invention has applications in the treatment of many different types of wounds, including, without limitation, diabetic ulcers, gangrene, venous ulcers, decubitus ulcers, pressure ulcers, wounds due to bites, acute trauma wounds, surgical wounds and burns. The composition of the present invention is also useful as an irrigation solution, for example, during dental, periodontal, and ophthalmic procedures. The composition of the present invention can also be used for pre- and post-operative cleaning of tissue sites, and as a gargling solution for treatment of canker sores.

Methods of Using a Composition for Skin Disinfection

The composition of the present invention may also be used to treat skin that is infected. In a skin of a patient showing medical signs of infection, the composition of the present invention may be applied directly to the area of the skin that is infected. After at least one application of the composition onto the infected skin using standard methods of application known in the art, the disinfective properties of the composition may be noted.

Reduction of Pathogens in Pulmonary Infections

The composition of the present invention may be used for the reduction of pathogens in pulmonary infections. For example, various viral or bacterial and fungal infections may be effectively treated with the composition of the present invention. Non-limited examples of infections that may be effectively treated using the composition of the present invention include anthrax spores present in the lungs, and the reduction of pneumonia causing bacteria in the lungs, including *Streptococcus* bacteria and the like.

Methods of Using the Solutions of the Invention in Gynecology

The composition of the present invention may be used for the treatment of gynecological infections, such as vaginal infections and the like. For example, various microorganisms, yeasts (e.g., *Monilia, Candida albicans*, etc.), bacterial infections, HSV-2, HIV or other pathogenic agents may be effectively treated with the composition of the present invention. Optionally, the application of the compositions of the present invention can be used with other medications for the treatment of gynecological infections. For example, use as a lavage of birth canal in pregnant female patients with suspected venereal diseases, and potentially as bathing and cleansing solution on babies right after birth in the deliver rooms of hospitals or as disinfectant on catheters and shunts in dialysis rooms.

Method of Use as a Treatment for Topical Infections

The compounds of the present invention may be used to treat topical infections by incorporating them into creams, ointments or lotions for use in such conditions. Such creams, ointments or lotions might be used a broad variety of skin conditions and may incorporate penetration enhancers in order to deliver the antimicrobial activity of the compound to microbes present beneath the outer (epidermis) layers of the skin and cleansers which remove layers of oil above the epidermis.

Method of Use to Prevent Surgical Site Infections

Isotonic solutions of the present invention may be used as an irrigant during surgery in order to prevent the development of surgical site infections, that frequently lead to prolonged hospitalizations and, occasionally, in death. The use of a solution of the present application in place of saline could substantially reduce the risks of such infections especially in the case of gastric surgery and of prolonged operations, where the rate of infections may be as high as 10%.

Method of Use for Disinfection of Medical Devices and Surgical Implements

The solution of the present application may be used for the reduction of pathogens on the surfaces of medical devices and surgical implements to prevent infection to the patient on whom the implements and devices are used, or in whom they are implanted. The solution may also be used for the reduction or elimination of infections that occur at the entry ports of catheters and shunts that are particularly prone to such infections.

The solution of the present application may be used for the eradication of bacteria in a biofilm, such as, but not limited to, that on the lumen of a catheter, or the destruction of the corresponding biofilm matrix which clears the bacterial load from the catheter. Biofilms are a group of microorganisms attached to a substrate and are often associated with the excretion of extracelullar polymeric substance [R. M. Donlan, *Emerg. Infect. Dis.*, 2002, 8(9), 881-90]. The demonstrated resistance of biofilms to antimicrobials has caused problems in human health and has had a significant impact on the success of medical implants, for example, catheters [J. W. Costerton et al., *Science,* 1999, 284(5418), 1318-22]. Once catheters are colonized, biofilms will develop on the outer and inner surfaces and cause infections. Reduction of the bacterial load by prevention of the formation of biofilm (Williams, J. F.; Worley, S. D. *J. Endourology* 2000, 14(5), 395-400; Lewis, K.; Klibanov, A. M. *TRENDS in Biotech.* 2005, 23, 7, 343-348), destruction of an existing biofilm (Wood, P.; Jones, M.; Bhakoo, M.; Gilbert, P. *Appl. Env. Microb.* 1996, 62(7), 2598-2602) and killing bacteria in biofilm (Gilbert, P.; McBain, A. J. *Am. J. Infect. Control* 2001, 29, 252-255) are strategies towards lowering microbial load and reducing biofilm-related infection from any catheters and shunts, such as but not limited to urinary and central venous catheters, implanted artificial joints, implanted artificial hearts, gastric feeding tubes, and colostomy tubes.

Method of Use for Surface Disinfection

The solution of the present invention may be applied directly or through delivery from a device that creates a mist (aerosolization) to the surfaces of a room, vehicle interior or other such largely confined space in order to reduce or eliminate infectious pathogens that may be suspected to be present. In such an application, it could be used to decontaminate operating theaters where infectious pathogens have been detected or rooms, vehicles and other surfaces where biological warfare agents have been dispersed, as well as operating rooms and hospital waiting rooms where infectious pathogens are likely to reside and multiply.

Method of Use for Improving Food Safety

The solution of the present invention may be used for reducing pathogens on food (including, without limitation, meats, fruits and vegetables). The solution could be applied as a wash or mist to the food, or the food could be dipped in the solution. The solution of the present invention may also be applied to surfaces and implements used in the preparation of foods to prevent the transfer of pathogens from such surfaces and implements to the food.

Method of Use as an Antimicrobial Preservative

The compounds of the present invention may be used as a means of ensuring that microbes cannot survive in solutions intended for use in injection, infusion or for use in the eye by incorporation of an appropriate amount of such compound into the solution at the time of manufacture.

Method of Use as an Antimicrobial

A formulation of compounds of the present invention may be used as a means of safely and rapidly disinfecting the hands of surgeons and nurses to reduce the risk of transporting infectious agents into an operating theatre. Additionally, a formulation of compounds of the present invention may be used to eliminate the infectious agent from the skin of patients (pre- and post-operative) in the area of a surgical incision.

Method of Wound Care

Patients suffering from long-lasting non-healing wounds should be treated with the acidic composition of the present invention on a daily basis, typically about once or twice a day.

The solution of the present invention may be used as follows: a gauze material or gauze pad is presoaked with enough solution to saturate it and is then squeezed to remove excess solution. This removes species present in the gauze which would react with and reduce the effectiveness of the solution of the present invention. The gauze is wetted after this procedure, but not soaked. Additional solution is then applied to completely wet the gauze, which is then immediately applied to the wound. In the alternative, the gauze may be applied to the wound and then additional solution is applied. Typically the wound site is packed with the solution-soaked gauze, and optionally, a Vaseline gauze can be applied on top of the packed wound to keep it moist and free of contaminating germs. The wound site is then wrapped with wound dressings as is standard in the art. The solution may also be used to clean a wound by pouring it directly on the wound site to remove any necrotic tissue by a mechanical procedure, and also as a cleanser or irrigant.

The patient may also make use of a "wound care kit," which permits the patient to periodically pour the solution of the present invention onto the wound site without having to remove the dressing. This kit provides ease-of-use, portability and dramatically reduces exposure of the wound to/from re-infection. The wound care kit includes a package containing the solution of the present invention and bandaging material. Often the kit contains a package containing the solution of the present invention and a specialized bandage for use in combination with the solution. The specialized bandage keeps the skin surrounding the wound dry while the wound is treated. Further, the bandage may be applied in a physician's office or at a hospital, with the patient continuing care at home; may be applied and used at home under the instructions of a physician; or for minor injuries, the wound care kit may be used as an "over the counter" treatment by the patient alone.

Packaging for Certain Uses

In another aspect of the present invention, the formulations of the present invention may be packaged to contain the composition in individual, single use containers. The single-use containers may be used for example, for application in single change of dressing or equivalents thereof. The single-use containers of the present invention may be used in conjunction with commonly used bandages. In another aspect of the present invention, a wound care kit may comprise single-use containers of the solutions of the present invention with the specialized bandages for various applications.

In another aspect of the present invention, the solutions of the present invention may be produced in-situ by the use a dual-chamber apparatus or packaging as shown in the FIGURE with or without a third mixing chamber.

The Dual-Chamber may consist of two syringes or pouches. To make NNCA (N,N-dichloro amino acid) solution with a concentration of 3.2 mM at pH 3.5, for example, chamber A is filled with 12.8 mM NaOCl solution, chamber B is filled with 3.3 mM of 2-amino-2-methylpropane-1-sulfonic acid dissolved in acidified 1.8% of saline solution. The acidity of the solution in chamber B is adjusted with 1 M HCl so that when the solutions in two chambers are mixed either in a common delivery tube or in a mixing chamber C, the reaction will give desired NNCA concentration and pH value. Since 2-amino-2-methylpropane-1-sulfonic acid is stable in acidic solution, and NaOCl is stable at room temperature, the use of the on-site preparation method described above can avoid any stability problem with NNCA solutions. In other applications of the above process, the corresponding sodium sulfonate salt may be used to prepare the solution instead of the sulfonic acid as described above.

Specific Compositions of the Invention

In another aspect of the invention, there is provided a composition having a concentration of the N-halo- or N,N-dihaloamino compound or its derivative between about 0.001 mM to about 4 M (molar), 0.05 mM to about 2 M, about 0.01 mM to about 1 M, about 1 M to about 2 M, about 2 M to about 3 M, about 3 M to about 4 M, about 0.1 mM to about 0.1 M or about 0.1 to about 50 mM. The pH range of the solution may be between about 1 to about 13, about 7 to about 9, about 9 to about 12, about 12 to about 13, about 2 to about 8, about 3 to about 4.8, about 3 to about 4.5, about 3.5 to about 4.5, or at about 3.5, or at about 2. The pH can be easily adjusted by various buffer systems known in the art.

In yet another aspect, there is provided a stabilized composition with bactericidal, antibacterial, anti-infective, antimicrobial, sporicidal, disinfectant, antifungal and antiviral activity comprising an N-halo- or N,N-dihalo-amino compound of the formulae I-VII or the derivatives thereof; the composition having a concentration of the N-haloamino compound or N,N-dihaloamino compound or its derivative between about 0.1 to about 50 mM and a pH range between about 1 to about 13. In certain application, the composition has a pH range of about 2.0 to about 7.0, about 3.0 to about 6.0, about 3.0 to about 4.8, about 3.0 to about 4.5, or about 3.5 to about 4.5, or at about 3.5. In one variation, the composition having a concentration of the N-haloamino compound or N,N-dihaloamino compound or its derivative is between about 0.01 mM to about 1 M.

In one aspect of the above, the composition is in a receptacle ensuring its long-term stability required by its bactericidal, antibacterial, anti-infective, antimicrobial, sporicidal, disinfectant, antifungal or antiviral use. That is, the compositions disclosed herein may be stored in a receptacle ensuring its long-term stability and shelf life sufficient for its application as a bactericidal, antibacterial, anti-infective, antimicrobial, sporicidal, disinfectant, antifungal or antiviral agent.

In one variation, the concentration of the N-haloamino compound or the N,N-dihaloamino compound or its derivative between about 0.1 to about 100 mM, preferably about 0.3 to about 50 mM. In another aspect, the composition is in stabilized form. In yet another aspect, the composition is stored in a receptacle ensuring its long-term stability required by its bactericidal, antibacterial, anti-infective, antimicrobial, sporicidal, disinfectant, antifungal or antiviral use.

In one variation, there is provided a method of preventing or treating an infection caused by a bacterial, a microbial, a sporal, a fungal or a viral activity in a mammal, the method comprising the administration of a bactericidal, antibacterial, anti-infective, antimicrobial, sporicidal, disinfectant, antifungal and antiviral amount of an N,N-dihalo-amino compound of the formulae I-VII. In another aspect, the composition has a therapeutic index of about 20 to about 5,000.

In yet another aspect of the present invention, there is provided a method for controlling or preventing the growth of bacteria, microbes, spores, fungi or viruses or the proliferation of infections and the source of infections, the method comprising the application of an effective amount of a composition of the present invention to an area, space or material requiring the control or prevention of growth or proliferation. In one variation, the pH of the composition is between about 2 to about 7, about 3.0 to about 6.8, about 3 to about 6, about 3 to about 5, or about 3.5.

In one aspect of the above methods, the N,N-dihalo amino compound or derivative thereof is prepared in situ. In one variation of the above methods, the material to be treated is selected from the class consisting of food, animal feed, surgical instruments, surgical equipment, medical devices and equipment used for such purposes.

In one variation, the composition has a concentration of the specific N-halo- or N,N-dihaloamino compound or its derivative between about 0.01 mM to about 1 M, about 0.1 and about 100 mM, or about 0.3 to about 50 mM and a pH range between about 3 to about 4.8, about 3.0 to about 4.5, or about 3.5 to about 4.5, or at about 3.5.

In another aspect, the composition is in stabilized form, the composition having a concentration of the specific N-halo- or N,N-dihaloamino compound or its derivative between 0.1 and 100 mM or 0.1 to 50 mM and a pH range between about 2 to about 7, 3 to 6, 3 to 4.8, 3 to 4.5, or 3.5 to 4.5, or at about 3.5. The pH may be adjusted using suitable buffer systems well-known to a person skilled in the art. In one variation the composition being in a receptacle ensuring its long-term stability required by its bactericidal, antibacterial, anti-infective, antimicrobial, sporicidal, disinfectant, antifungal or antiviral use.

In one aspect of the present invention, there is provided the use of an N-halo- or N,N-dihalo-amino compound of the present invention in the preparation of a bactericidal, antibacterial, anti-infective, antimicrobial, sporicidal, disinfectant, antifungal and antiviral activity composition. In another aspect, there is provided a composition as described above, further comprising a halogenated compound selected from the group consisting of a hypohalous acid or a salt thereof. In one variation of the above, the composition is acidic.

In a particular variation of the method described above, the method further comprising the use of a halogenated compound selected from the group consisting of a hypohalous acid or a salt thereof. In one variation of the above method, the administered composition is acidic.

Various methods may be developed for preparing the compounds of the present invention. Representative methods for preparing these compounds are provided in the Examples. However, the compounds of the present invention may also be synthesized by other synthetic routes as is well known in the art of synthetic chemistry. Some of the present compounds have chiral centers. The preparation of the compounds of the present invention may result in the formation of mixtures of different stereoisomers (enantiomers, diastereomers). Unless a particular stereochemistry is specified, recitation of a compound is intended to encompass all of the different possible stereoisomers. The compounds of the present invention can also be prepared as a pharmaceutically acceptable acid addition salt by reacting the free base form of the compound with a pharmaceutically acceptable inorganic or organic acid. The base addition salts may also be prepared by reacting the acid with a pharmaceutically acceptable inorganic or organic base.

EXAMPLES

The starting materials and reagents used in preparing the compounds described herein are either available from commercial suppliers such as Aldrich-Sigma Chemical Co. (Milwaukee, Wis., USA), Bachem (Torrance, Calif., USA), Torento Research Chemicals (North York, ON, Canada), Anaspec (San Jose, Calif., USA), Chem-Impex International (Wood Dale, Ill., USA), Spectrum (Gardena, Calif., USA), PharmaCore (High Point, N.C., USA) or are prepared by methods known to those skilled in the art following procedures set forth in references such as Fieser and Fieser's *Reagents for Organic Synthesis*, Volumes 1-5 and Supplementals (Elsevier Science Publishers, 1989), *Organic Reactions*, Volumes 1-40 (John Wiley and Sons, 1991), *March's Advanced Organic Chemistry*, (John Wiley and Sons, 4$^{th}$ Edition), and Larock's *Comprehensive Organic Transformations* (VCH Publishers Inc., 1989).

Example 1

3-(4-chlorophenyl)-2-(dichloroamino)-2-methylpropane-1-sulfonic acid (Compound 570) and its sodium salt

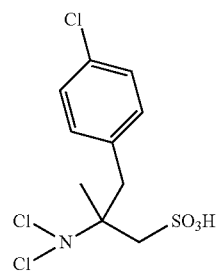 [SMILES: CC(Cc1ccc(Cl)cc1)(CS(=O)(=O)O)N(Cl)Cl]

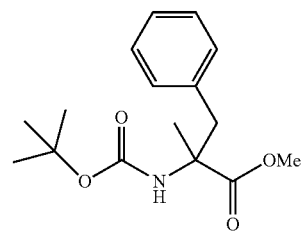 [SMILES: COC(=O)C(C)(Cc1ccccc1)NC(=O)OC(C)(C)C]

a) Methyl 2-(t-butylcarboxyamino)-2-methyl-3-phenyl-1-propionate. N-t-butyl-oxycarbonyl-α-methyl-phenylalanine (5 g) was dissolved in THF (50 mL) and MeOH (50 mL), and cooled to 0° C. Trimethylsilyldiazomethane (2.0 M in hexanes, 10 mL, 20 mmol) was added, dropwise, over 15 min, and the solution slowly warmed to RT over 3 h. The solution was evaporated to give the crude product as a clear oil (5.0 g, 71%) which was used as such for the next step.

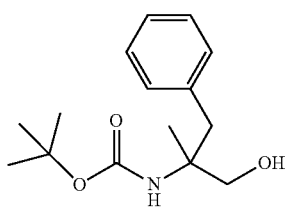 [SMILES: CC(CO)(Cc1ccccc1)NC(=O)OC(C)(C)C]

b) 2-(t-Butylcarboxyamino)-2-methyl-3-phenylpropan-1-ol. A solution of methyl-2-(t-butylcarboxyamino)-2-methyl-3-phenyl-1-propionate (5.0 g, 17 mmol) in THF (100 mL) was cooled to 0° C. and lithium borohydride (1.87 g, 85 mmol) in THF (20 mL) was added, dropwise, over 30 min. The reaction mixture was warmed to RT slowly and stirred vigorously for 20 h, during which time a thick white precipitate formed. The slurry was quenched by the addition of sat. NH$_4$Cl, and extracted with 5×100 mL EtOAc. The organic layers were combined, dried over Na$_2$SO$_4$, and evaporated. The crude material was purified by flash chromatography (1:4 EtOAc/hexanes) to afford the title product as a white solid (4.3 g, 95%). $^1$H NMR (DMSO-d$_6$, 400 MHz): δ 1.06 (s, 3H), 1.41 (br s, 9H), 2.49 (br s, 1H), 2.82 (d, J=12.8 Hz, 1H) 3.31-3.33 (m, 2H), 4.74-4.77 (m, 1H), 5.99 (br s, 1H), 7.14-7.27 (m, 5H).

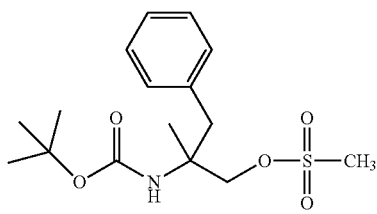 [SMILES: CC(COS(C)(=O)=O)(Cc1ccccc1)NC(=O)OC(C)(C)C]

c) 2-(t-Butylcarboxyamino)-2-methyl-3-phenyl-1-propanylmethanesulfonate. A solution of 2-(t-butylcarboxyamino)-2-methyl-3-phenyl-1-propanol (4.1 g, 15.5 mmol) in 40 mL CH$_2$Cl$_2$ and triethylamine (3.24 mL, 23.3 mmol) was cooled to 0° C. and methanesulfonyl chloride (2.1 gm, 18.6 mmol) in 20 mL CH$_2$Cl$_2$ was added, dropwise, over 30 min. The reaction was stirred at 0° C. for 5 h. The reaction mixture diluted with 400 mL CH$_2$Cl$_2$, washed with 2×100 mL sat. NaHCO$_3$, 2×100 mL 10% citric acid, 1×100 mL sat. NaCl, dried on Na$_2$SO$_4$, and evaporated. The crude product was purified with flash chromatography (1:9 to 1:1 EtOAc/hexanes) to afford the title product (5.2 g, 98%). $^1$H NMR (CDCl$_3$, 400 MHz): δ 1.21 (s, 3H), 1.46 (br s, 9H), 2.74 (d, J=13.2 Hz, 1H), 3.03 (s, 3H), 3.22 (d, J=13.6 Hz, 1H), 4.27 (d, J=9.6 Hz, 2H), 4.55 (d, J=9.6 Hz, 1H), 7.16-7.18 (m, 2H), 7.26-7.33 (m, 3H).

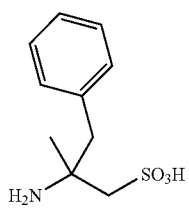

d) 2-Amino-2-methyl-3-phenylpropane-1-sulfonic acid. 2-(t-Butylcarboxy-amino)-2-methyl-3-phenyl-1-propanylmethanesulfonate (5 g, 14.6 mmol) was dissolved in 4 M HCl in 1,4-dioxane (50 mL), and the solution stirred for 16 h. The solution was evaporated and the residue dissolved in 1.0 M Na$_2$SO$_3$ (50 mL). The solution was stirred for 46 h, evaporated, and the resulting white residue was extracted with warm EtOH (5×20 mL). The ethanol portions were combined and evaporated to give the title compound as an amorphous solid (2.5 g, 68%).

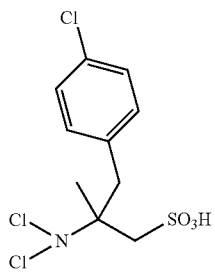 [SMILES: CC(Cc1ccc(Cl)cc1)(CS(=O)(=O)O)N(Cl)Cl]

e) 3-(4-Chlorophenyl)-2-(dichloroamino)-2-methylpropane-1-sulfonic acid. 2-Amino-2-methyl-3-phenylpropane-1-sulfonic acid (1.25 g, 5 mmol) was dissolved in H$_2$O (40 ml) and bleach (approx. 0.67 M NaOCl, 15 ml) was added. The pH of the solution was adjusted with dropwise addition of 1.0 M HCl in H$_2$O. Another 20 mL bleach was added, dropwise, with adjustment of the pH to 7 after every drop, and the resulting solution stirred for 2 h at RT. The solution was evaporated, and the resulting material extracted with EtOH:CH$_2$Cl$_2$(1:2, 3×10 mL). The organic phases were combined, filtered, and evaporated, and the crude material purified by flash chromatography (1:6 to 1:2 MeOH:CH$_2$Cl$_2$) to give the title compound as an amorphous solid (0.61 g, 37%). $^1$H NMR (CD$_3$OD, 400 MHz): δ 1.45 (br s, 3H), 3.25 (d, J=16 Hz, 1H), 3.48 (d, J=12 Hz, 1H), 3.65 (d, J=12 Hz, 1H), 4.17 (d, J=16 Hz, 1H), 7.20-7.26 (m, 2H), 7.35-7.37 (m, 1H), 7.52-7.54 (s, 1H). ES–MS (–ve) for C$_{10}$H$_{12}$Cl$_3$NO$_3$S (332.96); found: 330.1, 332.1, 334.1.

f) Sodium salt. $^1$H NMR (CD$_3$OD, 400 MHz): δ 1.45 (br s, 3H), 3.25 (d, J=16 Hz, 1H), 3.48 (d, J=12 Hz, 1H), 3.65 (d, J=12 Hz, 1H), 4.17 (d, J=16 Hz, 1H), 7.20-7.26 (m, 2H), 7.35-7.37 (m, 1H), 7.52-7.54 (s, 1H). ES–MS (–ve) for C$_{10}$H$_{12}$Cl$_3$NO$_3$S (332.96); found: 330.1, 332.1, 334.1.

Example 2

3-(2-(Dichloroamino)-2-methylpropoxy)propane-1-sulfonic acid

Compound 607

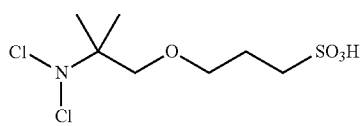

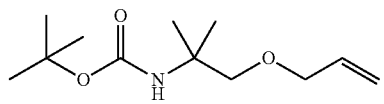 [SMILES: C=CCOCC(C)(C)NC(=O)OC(C)(C)C]

a) t-Butyl-1-(allyloxy)-2-methylpropan-2-ylcarbamate. t-Butyl-1-hydroxy-2-methylpropan-2-ylcarbamate (Regis Technologies, Inc., IL, USA) (5.75 g, 30.4 mmol) in DMF (60 mL) was cooled at 0° C. and sodium hydride (60% suspension, 1.34 g, 33.4 mmol) was added and stirred for 10 min. Allyl bromide (3.08 mL, 36 mmol) was added and the mixture was stirred over night at RT. DMF was removed under reduced pressure and the residue suspended in ethyl acetate (150 mL), washed with water, then brine, and dried over sodium sulfate. The resulting solution was concentrated and purified over silica gel using 2% EtOAc/hexane as eluent to afford 6.3 g (91%) of the title compound. ¹H NMR (CDCl₃, 400 MHz) δ 1.3 (s, 6H), 1.34 (s, 9H), 3.37 (s, 2H), 3.99-4.01 (m, 2H), 4.75 (br s, 1H), 5.17-5.30 (m, 2H), 5.86-5.94 (m, 1H).

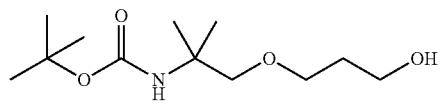 [SMILES: CC(C)(COCCCO)NC(=O)OC(C)(C)C]

b) t-Butyl 1-(3-hydroxypropoxy)-2-methylpropan-2-ylcarbamate. t-Butyl-1-(allyloxy)-2-methylpropan-2-ylcarbamate (3 g, 13.1 mmol) in THF (40 mL) was cooled at 0° C. and 9-BBN (5M, 26 mL, 13.1 mmol) was added. The mixture was heated and stirred at 65° C. for 2 h, then cooled in ice. H₂O₂ (30%, 1.63 mL) was added followed by 5N NaOH (1 mL) and the mixture stirred for 30 min. The solution was evaporated under reduced pressure and purified over silica gel using 40% EtOAc/hexane to afford 2.77 g (84%) of the title compound. ¹H NMR (CDCl₃, 400 MHz) δ 1.25 (s, 6H), 1.43 (s, 9H), 1.81-1.87 (m, 2H), 2.32 (br s, 1H), 3.43 (s, 2H), 3.65 (t, J=6 Hz, 2H), 3.75-3.80 (m, 2H), 4.67 (br s, 1H).

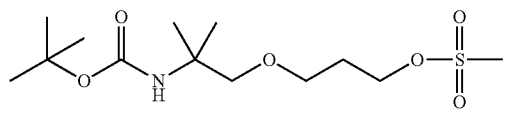 [SMILES: CC(C)(COCCCOS(C)(=O)=O)NC(=O)OC(C)(C)C]

c) 3-(2-(t-Butoxycarbonylamino)-2-methylpropoxy)propylmethanesulfonate. t-Butyl-1-(3-hydroxypropoxy)-2-methylpropan-2-ylcarbamate (2.45 g, 9.9 mmol) was dissolved in CH₂Cl₂ (30 mL) and triethylamine (1.65 mL, 11.9 mmol) was added. The mixture was cooled in ice and methanesulfonyl chloride (0.84 mL, 10.9 mmol) was added. The mixture was stirred for 3 h at RT and water (20 mL) was added. The organic layer was separated and the aqueous layer was extracted with CH₂Cl₂ (3×50 mL). The combined organic layers were washed with water and dried over sodium sulfate. Upon concentration, the mesylate was obtained as a light yellow solid which was used for the next step without further purification (2 g, 63%).

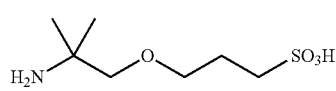

d) 3-(2-Amino-2-methylpropoxy)propane-1-sulfonic acid. 3-(2-(t-butoxycarbonyl-amino)-2-methylpropoxy)propylmethanesulfonate (2 g, 6.15 mmol) was dissolved in 4 M HCl in 1,4-dioxane (20 mL), and the solution stirred for 1 h. The solution was evaporated, and the residue dissolved in H₂O (10 ml) and 1M Na₂SO₃ (12.3 mL, 12.3 mmol) was added. The solution was heated at 50° C. for 16 h and evaporated to dryness. The resulting white residue was extracted with warm EtOH (4×50 mL). The ethanol portions were combined and evaporated. The crude material was purified by flash chromatography (30% MeOH/CH₂Cl₂) to give the title compound as a white solid (750 mg, 53%). LCMS (ESI-neg) m/z 210 (M-H).

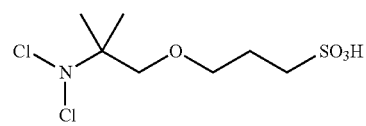

e) 3-(2-(Dichloroamino)-2-methylpropoxy)propane-1-sulfonic acid. Commercial bleach (3.6 mL, 5% NaOCl, 2.4 mmol) was adjusted to pH 5 with dropwise addition of 6 M HCl. This solution was added dropwise to a solution of 3-(2-amino-2-methylpropoxy)propane-1-sulfonic acid (250 mg, 1.4 mmol) in H₂O (5 mL). The solution was stirred for 1 h, until the starting amino sulfonic acid had been completely consumed (followed by LCMS). The solution was evaporated and the residue was subjected to column chromatography over silica gel using 10% MeOH/CH₂Cl₂ to afford the dichloramine as a white powder (200 mg, 51%). ¹H NMR (CD₃OD, 400 MHz) δ 1.34 (s, 6H), 2.03-2.07 (m, 2H), 2.89-2.93 (m, 2H), 3.54 (s, 2H), 3.59 (t, J=6 Hz, 2H). LCMS (ESI-Neg) for C₇H₁₅C₁₂NO₄S (279.01); found: 278 (M-H).

Example 3

3-(2-(Dichloroamino)-2-methylpropoxy)-3-oxopropane-1-sulfonic acid

Compound 614

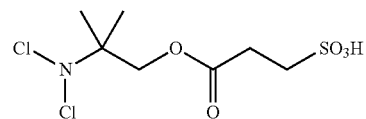 [SMILES: CC(C)(COC(=O)CCS(=O)(=O)O)N(Cl)Cl]

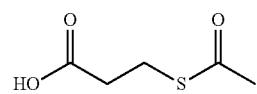

a) 3-(Acetylthio)propanoic acid. Following the method of A.-H. Li et al. (*J. Med. Chem.* 1999, 42, 706), a solution of 3-mercaptopropanoic acid (5 g, 47.1 mmol) in a mixture of glacial acetic acid (20 mL) and methylene chloride (20 mL) was kept in ice water. Acetyl chloride (18.5 mL, 233.5 mmol) was added and the mixture allowed to warm to RT. The mixture was stirred at RT for 30 h and concentrated. Column purification on silica gel using 10% EtOAc/Hexane afforded the thioacetate in 78% (5.3 g) yield. $^1$H NMR (CDCl$_3$, 400 MHz) δ (s, 3H), 2.7 (t, J=6.8 Hz, 2H), 3.11 (t, J=7.2 Hz, 2H).

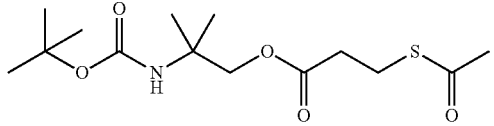 [SMILES: CC(=O)SCCC(=O)OCC(C)(C)NC(=O)OC(C)(C)C]

b) 2-(t-Butoxycarbonylamino)-2-methylpropyl 3-(acetylthio)propanoate. To a solution of 3-(acetylthio)propanoic acid (2.3 g, 15.9 mmol) in DMF (30 mL), 1,1'-carbonyl diimidazole (2.6 g, 15.9 mmol) was added. After stirring for 20 min, t-butyl 1-hydroxy-2-methylpropan-2-ylcarbamate (3 g, 15.9 mmol) was added and the mixture was heated at 60° C. for 3 days. DMF was removed under vacuum and the residue was suspended in EtOAc. The organic layer was washed successively with 1 N HCl, water and brine. Concentration and column purification over silica gel using 20% EtOAc/hexane afforded the thioacetate (2 g, 40%). $^1$H NMR (CDCl$_3$, 400 MHz) δ 1.3 (s, 6H), 1.43 (s, 9H), 2.34 (s, 3H), 2.67 (t, J=7.2 Hz, 2H), 3.13 (t, J=7.2 Hz, 2H), 6.16 (s, 2H), 4.5 (br s, 1H).

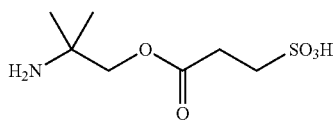

c) 3-(2-Amino-2-methylpropoxy)-3-oxopropane-1-sulfonic acid. According to the method of L. Hu et al. (*J. Org. Chem.* 2007, 72, 4543), hydrogen peroxide (30%, 5.7 mL, 50.2 mmol) was added to 90% formic acid (20 mL) at 0° C. and was stirred at RT for 1 h. The solution was recooled to 0° C. and 2-(t-butoxycarbonylamino)-2-methylpropyl-3-(acetylthio)propanoate (2 g, 6.3 mmol) was added. The mixture was stirred at RT for 24 h and concentrated. Upon the addition of 50% MeOH/CH$_2$Cl$_2$, the aminosulfonic acid was precipitated out, then filtered and dried (1.1 g, 78%). $^1$H NMR (CD$_3$OD, 400 MHz) δ 1.39 (s, 6H), 2.81-2.85 (m, 2H) 3.15-3.18 (m, 2H), 4.19 (s, 2H). LCMS (ESI–Neg) for C$_7$H$_{15}$NO$_5$S (225.07); found: 224 (M–H).

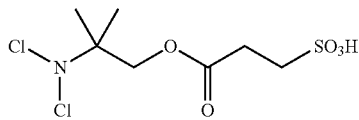 [SMILES: CC(C)(COC(=O)CCS(=O)(=O)O)N(Cl)Cl]

d) 3-(2-(Dichloroamino)-2-methylpropoxy)-3-oxopropane-1-sulfonic acid. Prepared analogously to Example 2, step (e), starting from the above aminosulfonic acid (700 mg, 3 mmol) and sodium hypochlorite (5%, 9.2 mL) Yield 520 mg (57%). $^1$H NMR (CDCl$_3$, 400 MHz) δ 1.42 (s, 6H), 2.81-2.85 (m, 2H), 3.09-3.13 (m, 2H), 4.27 (s, 2H). LCMS (ESI–Neg) for C$_7$H$_{13}$C$_{12}$NO$_5$S (292.99); found: 292 (M–H).

Example 4

3-(2-(Dichloroamino)-2-methylpropylamino)-3-oxopropane-1-sulfonic acid

Compound 616

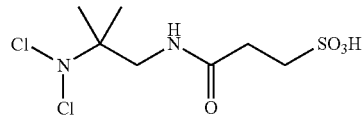 [SMILES: CC(C)(CNC(=O)CCS(=O)(=O)O)N(Cl)Cl]

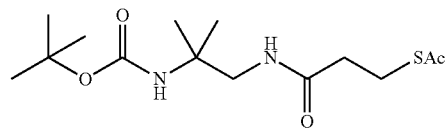

a) S-3-(2-(t-Butoxycarbonylamino)-2-methylpropylamino)-3-oxopropyl ethanethioate. A solution of 3-(acetylthio)propanoic acid (2 g, 13.5 mmol) in THF (50 mL) was treated with 1,1'-carbonyldiimidazole (2.19 g, 13.5 mmol). After 20 min, a solution of 2-methylpropane-1,2-diamine (1.2 g, 13.6 mmol) in THF was added at –40° C. The solution was stirred at this temperature for 1 h and allowed to warm at RT in 3 h. A few drops of methanol were added to make the solution clear and di-t-butyldicarbonate (4.4 g, 20.2 mmol) was added. The resulting mixture was stirred 16 h, concentrated under reduced pressure and purified on silica gel using 15% EtOAc/hexane. Yield 3.4 g (79%). $^1$H NMR (CDCl$_3$, 400 MHz) δ 1.27 (s, 6H), 1.43 (s, 9H), 2.33 (s, 3H), 2.53 (t, J=6.8 Hz, 2H), 3.16 (t, J=6.8 Hz, 2H), 3.43 (d, J=5.6 Hz, 2H), 4.66 (br s, 1H).

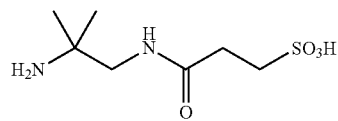

b) 3-(2-Amino-2-methylpropylamino)-3-oxopropane-1-sulfonic acid. Prepared analogously to Example 3, step (c), from S-3-(2-(t-butoxycarbonylamino)-2-methylpropylamino)-3-oxopropyl ethanethioate (3.4 g, 10.7 mmol) and H$_2$O$_2$ (30%, 9.7 mL, 85.6 mmol). Yield 1 g (42%). $^1$H NMR (CD$_3$OD, 400 MHz) δ 1.35 (s, 6H), 2.71-2.74 (m, 2H), 3.18-3.25 (m, 2H), 3.40 (s, 2H). LCMS (ESI–Neg) for C$_7$H$_{16}$N$_2$O$_4$S (224.08); found: 223 (M–H).

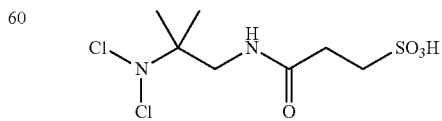

c) 3-(2-(Dichloroamino)-2-methylpropylamino)-3-oxopropane-1-sulfonic acid. Prepared analogously to Example 2, step (e), from 3-(2-amino-2-methylpropyl-amino)-3-oxopropane-1-sulfonic acid (1 g, 4.5 mmol) and sodium hypochlorite (5%, 13.3 mL, 9 mmol). Yield 0.6 g, 46%. $^1$H NMR (CD$_3$OD, 400 MHz) δ 1.36 (s, 6H), 2.68-2.72 (m, 2H), 3.05-3.09 (m, 2H), 3.52 (s, 2H). LCMS (ESI–Neg) for C$_7$H$_{14}$C$_{12}$N$_2$O$_4$S (292.01); found: 291 (M–H).

Example 5

3-((2-(Dichloroamino)-2-methylpropyl)(methyl)amino)-3-oxopropane-1-sulfonic acid Compound 619

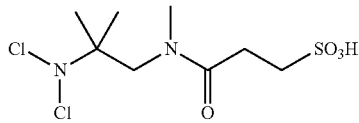 [SMILES: CN(CC(C)(C)N(Cl)Cl)C(=O)CCS(=O)(=O)O]

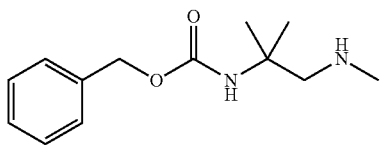 [SMILES: CNCC(C)(C)NC(=O)OCc1ccccc1]

a) Benzyl-2-methyl-1-(methylamino)propan-2-ylcarbamate. Di-t-butyldicarbonate (9.75 g, 44.7 mmol) in methanol (20 mL) was added dropwise to a solution of 2-methylpropane-1,2-diamine (3.94 g, 44.7 mmol) in methanol (40 mL) at −78° C. The mixture was left in the cooling bath until it reached RT. It was concentrated, re-dissolved in THF (60 mL) and cooled in ice. Benzyl N-succinimidyl carbonate (11.1 g, 44.7 mmol) was added and the mixture was stirred overnight, concentrated and re-dissolved in ethyl acetate. The mixture was washed successively with water, then brine, and dried over sodium sulfate and concentrated. The oily residue was stirred with 4N HCl (30 mL) at RT for 2 h and concentrated to get the CBZ-protected amine hydrochloride, which was stirred with 50% aqueous K$_2$CO$_3$ and extracted with chloroform. The chloroform layer was dried over sodium sulfate and concentrated to get the CBZ-protected amine. This amine (5 g, 22.5 mmol) was added to a pre-stirred mixture of formic acid (0.84 mL, 22.5 mmol) and 1,1'-carbonyl-diimidazole (3.64 g, 22.5 mmol) in THF, stirred for 2 h and concentrated. The residue was suspended in EtOAc and washed with sat. NaHCO$_3$, dried over sodium sulfate and concentrated to yield the N-formyl derivative (5.5 g, 98%). The N-formyl amine (5 g, 20 mmol) was dissolved in anh. THF (50 mL) and boranemethanesulfide (2M, 15 mL, 30 mmol) was added at 0° C. The mixture was stirred overnight and methanol was added (100 mL) followed by 2M HCl (20 mL) in methanol. After stirring for 1 h, the mixture was concentrated and suspended in EtOAc and then stirred with sat. K$_2$CO$_3$ solution. The organic layer was separated, dried and concentrated to yield the crude N-methyl amine, which was purified over silica gel using MeOH/CH$_2$Cl$_2$ to yield 3.2 g (68%) in pure form. $^1$H NMR (CDCl$_3$, 400 MHz) δ 1.31 (s, 6H), 2.43 (s, 3H), 2.59 (s, 2H), 5.04 (s, 2H), 7.34-7.35 (m, 5H).

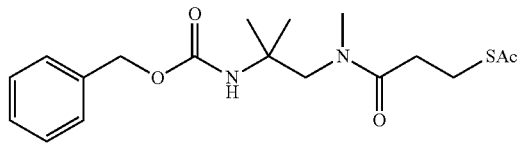

b) S-3-((2-(Benzyloxycarbonylamino)-2-methylpropyl)(methyl)amino)-3-oxopropyl ethanethioate. To a solution of 3-(acetylthio)propanoic acid (1.88 g, 12.7 mmol) in THF, 1,1'-carbonyldiimidazole (2.05 g, 12.7 mmol) was added and the solution stirred at RT for 20 min. Benzyl-2-methyl-1-(methylamino)propan-2-ylcarbamate (3 g, 12.7 mmol) was added and the mixture refluxed for 2 h. The solution was concentrated, suspended in EtOAc and washed successively with 1 N HCl, sat. NaHCO$_3$, and brine and was concentrated. Column purification over silica gel using 20% EtOAc/hexane afforded the thioacetate (2 g, 43%). $^1$H NMR (CDCl$_3$, 400 MHz) δ 1.35 (s, 6H), 2.30 (s, 3H), 2.65 (t, J=6.8 Hz, 2H), 3.01 (s, 3H), 3.15 (t, J=6.8 Hz, 2H), 3.50 (s, 2H), 5.06 (s, 2H), 7.29-7.35 (m, 5H).

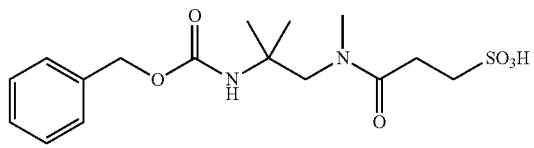 [SMILES: CN(CC(C)(C)NC(=O)OCc1ccccc1)C(=O)CCS(=O)(=O)O]

c) 3-((2-(Benzyloxycarbonylamino)-2-methylpropyl)(methyl)amino)-3-oxopropane-1-sulfonic acid. Prepared analogously to Example 3, step (c), from S-3-((2-(benzyloxy-carbonylamino)-2-methylpropyl)(methyl)amino)-3-oxopropyl ethanethioate in a yield of 90% (1.8 g). LCMS (ESI–Neg) for C$_{16}$H$_{24}$N$_2$O$_6$S (372.14); found: 371 (M–H).

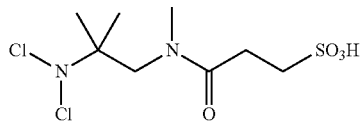 [SMILES: CN(CC(C)(C)N(Cl)Cl)C(=O)CCS(=O)(=O)O]

d) 3-((2-(Dichloroamino)-2-methylpropyl)(methyl)amino)-3-oxopropane-1-sulfonic acid. 3-((2-(Benzyloxycarbonylamino)-2-methylpropyl)(methyl)amino)-3-oxopropane-1-sulfonic acid (1 g, 2.7 mmol) was dissolved in methanol and 10% Pd—C (4 mg) was added. The mixture was hydrogenated at atmospheric pressure for 12 h. The catalyst was filtered off and concentrated to yield the aminosulfonic acid which was re-dissolved in methanol. The solution was cooled in ice-water and treated with t-butyl hypochlorite (0.6 g, 5.4 mmol). The solution was stirred at RT for 30 min and concentrated. The residue was purified over silica gel using 10% MeOH/CH$_2$Cl$_2$ to afford 800 mg (75%) of the desired N,N-dichloramine. $^1$H NMR (CD$_3$OD, 400 MHz) δ

1.37 (s, 6H), 2.81-2.84 (m, 2H), 3.17-3.20 (m, 2H), 3.26 (s, 3H), 3.57 (s, 2H). LCMS (ESI–Neg) for $C_8H_{16}C_{12}N_2O_4S$ (306.02); found: 305 (M–H).

Example 6

3-(2-(Dichloroamino)-2-methylpropoxy)-2,2-dimethyl-3-oxopropane-1-sulfonic acid Compound 625

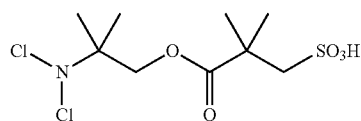 [SMILES: CC(C)(CS(=O)(=O)O)C(=O)OCC(C)(C)N(Cl)Cl]

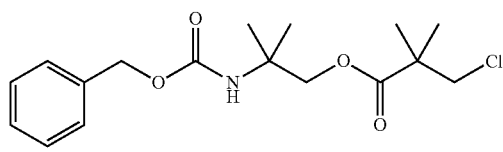 [SMILES: CC(C)(COC(=O)C(C)(C)CCl)NC(=O)OCc1ccccc1]

a) 2-(Benzyloxycarbonylamino)-2-methylpropyl 3-chloro-2,2-dimethylpropanoate. Benzyl 1-hydroxy-2-methylpropan-2-ylcarbamate (5 g, 22.4 mmol) was dissolved in dichloromethane (90 mL) and cooled in ice. Diisopropylethylamine (9.0 ml, 33.6 mmol) was added followed by 3-chloropivaloyl chloride (3.47 g, 22.4 mmol) dropwise. The mixture was stirred at RT for 2 days and concentrated. The residue was suspended in ethyl acetate and washed successively with 1 N HCl, sat. NaHCO$_3$ and finally with water. The solution was dried over sodium sulphate, concentrated and purified over silica gel using 10% EtOAc/hexane. Yield (5.6 g, 73%). $^1$H NMR (CDCl$_3$, 400 MHz) δ 1.23 (s, 6H), 1.35 (s, 6H), 3.14 (s, 2H), 4.14 (s, 2H), 5.06 (s, 2H), 7.26-7.35 (m, 5H).

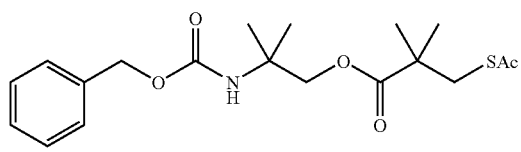

b) 2-(Benzyloxycarbonylamino)-2-methylpropyl 3-(acetylthio)-2,2-dimethylpropanoate. 2-(Benzyloxycarbonylamino)-2-methylpropyl-3-chloro-2,2-dimethylpropanoate (5 g, 14.7 mmol) was dissolved in DMF (60 mL). Potassium thioacetate (2.5 g, 22 mmol) was added and the mixture was heated at 100° C. for 5 h. DMF was removed under reduced pressure and the residue suspended in ethyl acetate. The organic layer washed with water, then brine and concentrated. The crude material was purified over silica gel to afford the thioacetate in 71% (4 g) yield. $^1$H NMR (CDCl$_3$, 400 MHz) δ 1.23 (s, 6H), 1.34 (s, 6H), 2.30 (s, 3H), 3.14 (s, 2H), 4.12 (s, 2H), 5.06 (s, 2H), 7.30-7.35 (m, 5H).

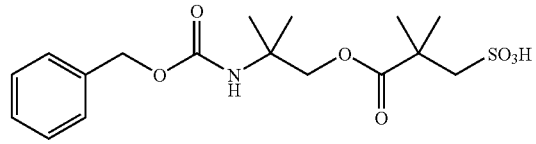 [SMILES: CC(C)(COC(=O)C(C)(C)CS(=O)(=O)O)NC(=O)OCc1ccccc1]

c) 3-(2-(Benzyloxycarbonylamino)-2-methylpropoxy)-2,2-dimethyl-3-oxopropane-1-sulfonic acid. Hydrogen peroxide (30%, 46.9 mmol, 5.3 mL) was added to 90% formic acid (20 mL) at 0° C. The mixture was stirred at RT for 1 h and cooled to 0° C. 2-(Benzyloxycarbonylamino)-2-methylpropyl-3-(acetylthio)-2,2-dimethylpropanoate (2 g, 5.9 mmol) in 90% formic acid (10 mL) was added and the mixture was stirred at RT for an additional 24 h. It was concentrated and purified over silica gel using 20% MeOH/CH$_2$Cl$_2$. Yield 76% (1.7 g). LCMS (ESI–Neg) for $C_{17}H_{25}NO_7S$ (387.14); found: 386 (M–H).

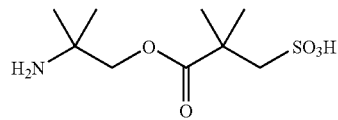 [SMILES: CC(C)(N)COC(=O)C(C)(C)CS(=O)(=O)O]

d) 3-(2-Amino-2-methylpropoxy)-2,2-dimethyl-3-oxopropane-1-sulfonic acid. 3-(2-(Benzyloxycarbonylamino)-2-methylpropoxy)-2,2-dimethyl-3-oxopropane-1-sulfonic acid (1.5 g, 3.94 mmol) was dissolved in methanol (20 mL) and 10% Pd—C (20 mg) was added. The mixture was hydrogenated at atmospheric pressure for 16 h. The catalyst was filtered off and the solution concentrated to afford the aminosulfonic acid in nearly quantitative yield (900 mg). LCMS (ESI–Neg) for $C_9H_{19}NO_5S$ (253.10); found: 252 (M–H).

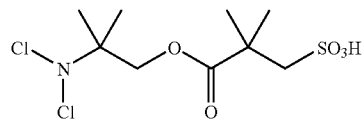 [SMILES: CC(C)(CS(=O)(=O)O)C(=O)OCC(C)(C)N(Cl)Cl]

e) 3-(2-(Dichloroamino)-2-methylpropoxy)-2,2-dimethyl-3-oxopropane-1-sulfonic acid. 3-(2-Amino-2-methylpropoxy)-2,2-dimethyl-3-oxopropane-1-sulfonic acid (500 mg, 1.9 mmol) was dissolved in methanol (20 mL). The solution was cooled in ice water and treated with t-butyl hypochlorite (0.41 g, 3.8 mmol). The resulting mixture was stirred at RT for 30 min and then concentrated. The residue was purified over silica gel using 10% MeOH/CH$_2$Cl$_2$ to afford 550 mg (87%) of the dichloramine. $^1$H NMR (CD$_3$OD), 400 MHz) δ 1.37 (s, 6H), 1.44 (s, 6H), 3.21 (s, 2H), 4.22 (s, 2H). LCMS (ESI–Neg) for C$_9$H$_{17}$C$_{12}$NO$_5$S (321.02); found: 320 (M–H).

Example 7

2-(3-(Dichloroamino)-3-methylbutanoyloxy)ethanesulfonic acid

Compound 628

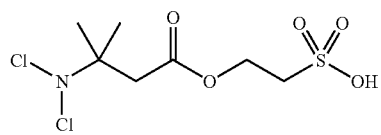 [SMILES: CC(C)(CC(=O)OCCS(=O)(=O)O)N(Cl)Cl]

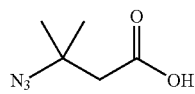

a) 3-Azido-3-methylbutanoic acid. According to the method of S. Nagarajan et al. (*J. Org. Chem.*, 1986, 51, 4856), to a stirred solution of 3,3-dimethylacrylic acid (20 g, 0.2 mol) in glacial acetic acid (50 mL) was added a solution of sodium azide (52 g, 0.8 mol) in water (100 mL) in one portion. The clear yellow solution was stirred for 1 h at RT and then heated in an oil bath at 95° C. for 2 days. Water (50 mL) was added to the cooled orange solution. This solution was poured into a separatory funnel and extracted with ether (5×200 mL). The combined organic extracts were dried over anh. MgSO$_4$ and concentrated to an orange oil (26.0 g, 91%). This oil was used without further purification.

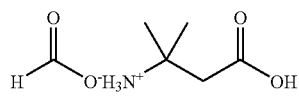

b) 1-Carboxy-2-methylpropan-2-ammonium formate. To an ice cold solution of crude 3-azido-3-methylbutanoic acid (14.00 g, 97.2 mmol) in formic acid (100 mL) was added 10% Pd/C (0.500 g) under a nitrogen atmosphere. The flask was sealed with a septum and the suspension was degassed with applied vacuum and a hydrogen flush (3 times). An oil bubbler was attached to the flask and the reaction was removed from the ice bath. After approximately 15 min, the flask became warm and hydrogen was liberated. After hydrogen ceased to be liberated from the reaction, the flask was fitted with a balloon filed with hydrogen and left to stir for 17 h. The suspension was filtered through a pad of Celite and the solid was washed with water (2×50 mL). The filtrate was concentrated to a light green oil. The residue was dissolved into water (200 mL) and extracted with ethyl acetate (2×200 mL). The aqueous layer was concentrated to a pale yellow oil (16.0 g, quantitative). This oil was used without further purification.

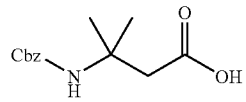

c) 3-(Benzyloxycarbonylamino)-3-methylbutanoic acid. N-(Benzyloxycarbonyloxy)succinimide (24.4 g, 1 equiv, 98 mmol) was added to a solution of 3-amino-3-methylbutanoic acid (16.0 g, 97.2 mmol) in methanol and water (200 mL: 100 mL) followed by the addition of THF (100 mL) to give a clear solution. The solution was cooled in an ice bath for 15 min and a solution of 5 N sodium hydroxide (39 mL, 2 equiv) was added over 15 min. The solution was stirred at 0° C. for an additional hour and stirred at RT for 17 h. The organic solvent was removed and the aqueous was extracted with ethyl acetate (2×200 mL) The aqueous layer was acidified with 6 N HCl (50 mL) and extracted with ethyl acetate (4×200 mL). The organic layer was dried over anh. MgSO$_4$, filtered, and concentrated to an orange yellow oil (16.2 g, 65.7%). This oil was used without further purification. LRMS (ESI–ve) for C$_{13}$H$_{17}$NO$_4$ (251.1); found: 250.

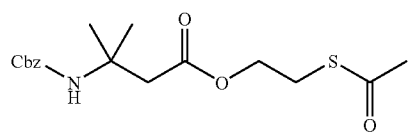 [SMILES: CC(=O)SCCOC(=O)CC(C)(C)NC(=O)OCc1ccccc1]

d) 2-(Acetylthio)ethyl 3-(benzyloxycarbonylamino)-3-methylbutanoate. 3-(Benzyloxycarbonylamino)-3-methylbutanoic acid (4.00 g, 15.9 mmol) was dissolved into anh. acetonitrile. Carbonyldiimidazole (2.83 g, 1.1 equiv, 17.5 mmol) was added to the flask in one portion and the flask sealed with a rubber septum. An oil bubbler was attached to the flask and the reaction stirred at RT for 30 min and S-2-hydroxyethyl ethanethioate (2.29 g, 1.2 equiv, 19.1 mmol) was added to the reaction via syringe in one portion. [S-2-hydroxyethyl ethanethioate was prepared from equimolar amounts of 2-iodoethanol and potassium thioacetate dissolved in methanol (0.5 M). The solution was heated at 60° C. for 1 h to give a suspension. The suspension was filtered and the filtrate concentrated to a red oil which was used without further purification.] The reaction was heated in an oil bath at 60° C. for 16 h. The solvent was removed and the residue was dissolved into a mixture of ethyl acetate (200 mL) and water (50 mL). The layers were separated and the organic layer was washed with water (2×50 mL), brine (50 mL), dried over anh. MgSO$_4$, filtered and concentrated to an oil. This material was purified by flash chromatography through silica gel with gradient elution from 10% ethyl acetate in hexanes to 30% ethyl acetate in hexanes. The fractions were collected and concentrated in vacuo to an oil which solidified on drying, (2.30 g, 41%). This material was used without further purification.

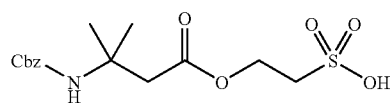 [SMILES: CC(C)(CC(=O)OCCS(=O)(=O)O)NC(=O)OCc1ccccc1]

e) 2-(3-(Benzyloxycarbonylamino)-3-methylbutanoyloxy)ethanesulfonic acid. 2-(Acetylthio)ethyl 3-(benzyloxycarbonylamino)-3-methylbutanoate (2.30 g, 6.51 mmol) was dissolved into formic acid (12 mL) and 30% hydrogen peroxide (6 mL) was added in one portion to the colorless solution and stirred at RT for 16 h. The solvent was removed to give a thick oil. The oil was flash chromatographed through silica gel with gradient elution from 2% methanol in dichloromethane to 10% methanol in dichloromethane. Two compounds were isolated; the faster running compound was 3-(benzyloxycarbonylamino)-3-methylbutanoic acid and the slower running compound was the desired product, (1.15 g, 49%). $^1$H NMR (CD$_3$OD, 400 MHz): δ 1.33 (s, 6H), 2.75 (s, 2H), 3.11 (t, 7.2 Hz, 2H), 4.40 (t, 7.2 Hz, 2H), 5.04 (s, 2H), 7.34 (m, 5H). LRMS (ESI–ve) for C$_{15}$H$_{21}$NO$_7$S (359.1); found: 358.

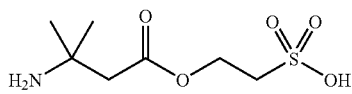

f) 2-(3-Amino-3-methylbutanoyloxy)ethanesulfonic acid. 2-(3-(Benzyloxycarbonyl-amino)-3-methylbutanoyloxy) ethanesulfonic acid (1.1 g, 3.06 mmol) was dissolved into methanol (20 mL) and cooled in an ice bath for 15 min and 10% Pd/C (107 mg) was added to the reaction in one portion. The flask was sealed and degassed with vacuum hydrogen flush (3 times). The reaction was stirred at RT for 16 h. The suspension was filtered through a pad of Celite and the solids washed with methanol (50 mL). The filtrate was concentrated to an oil. The oil was redissolved into a mixture of methanol: water (20 mL, 1:1, v:v). The suspension was filtered through a 0.45 μm membrane and concentrated to an oil and dried under high vacuum to give a white foam, (0.69 g, quant). This material was used without further purification. $^1$H NMR (D$_2$O, 400 MHz): δ 1.48 (s, 6H), 2.80 (s, 2H), 3.30 (t, 5.6 Hz, 2H), 4.55 (t, 5.6 Hz, 2H). LRMS (ESI–ve) for C$_7$H$_{15}$NO$_5$S (225.1); found: 224.

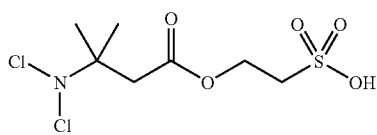 [SMILES: CC(C)(CC(=O)OCCS(=O)(=O)O)N(Cl)Cl]

g) 2-(3-(Dichloroamino)-3-methylbutanoyloxy)ethanesulfonic acid. 2-(3-(Dichloro-amino)-3-methylbutanoyloxy) ethanesulfonic acid was synthesized from 2-(3-amino-3-methylbutanoyloxy)ethanesulfonic acid following a procedure similar to the synthesis of 2-(dichloroamino)-N,N2-trimethylpropane-1-sulfonamide in Example 9, step (e), (0.51 g, 49%) $^1$H NMR (D$_2$O, 400 MHz): δ 1.48 (s, 6H), 2.92 (s, 2H), 3.27 (t, 6 Hz, 2H), 4.47 (t, 6 Hz, 2H). LRMS (ESI–ve) for C$_7$H$_{13}$Cl$_2$NO$_5$S (293.0); found: 292, 294.

Example 8

2-(2-(Dichloroamino)-2-methylpropylsulfonyl) ethanesulfonic acid

Compound 630

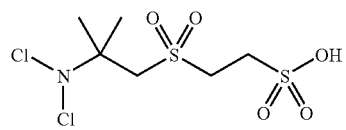 [SMILES: CC(C)(CS(=O)(=O)CCS(=O)(=O)O)N(Cl)Cl]

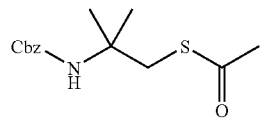 [SMILES: CC(=O)SCC(C)(C)NC(=O)OCc1ccccc1]

a) S-2-(Benzyloxycarbonylamino)-2-methylpropyl ethanethioate. According to the method of T. Bach et al., (*J. Org. Chem.*, 1998, 63, 1910), diisopropyl azodicarboxylate (DIAD) (11.8 g, 1.3 equiv, 58.2 mmol) was added at –5° C. in one portion to a vigorously stirred solution of triphenylphosphine (15.3 g, 1.3 equiv, 58.2 mmol) in anh. THF (225 mL, 0.2 M). A white suspension formed within 15 min. After stirring for 30 min, a solution of benzyl 1-hydroxy-2-methylpropan-2-ylcarbamate (10.0 g, 44.8 mmol) and thioacetic acid (4.43 g, 1.3 equiv, 58.2 mmol) in anh. THF (100 mL) was added dropwise over an hour. The suspension was left to stir and warm overnight. The deep yellow solution was concentrated to a viscous oil. The oil was triturated with a 200 mL of 20% ethyl acetate in hexanes. The solid was filtered and rinsed with 20% ethyl acetate in hexanes (3×50 mL). The filtrate was concentrated to a yellow oil, which was flash chromatographed through silica gel (600 g) with gradient elution from 5 to 10% ethyl acetate in hexanes. Yielded 8.31 g, light yellow oil, 66%. $^1$H NMR (CDCl$_3$, 400 MHz): δ 1.35 (s, 6H), 2.35 (s, 3H), 3.30 (s, 2H), 4.90 (br s, 1H), 5.05 (s, 2H), 7.35 (m, 5H). LRMS (ESI+ve) for C$_{14}$H$_{19}$NO$_3$S (281.1); found: (M+H$^+$) 282 and (M+Na$^+$) 304.

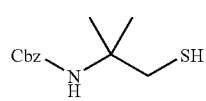

b) Benzyl 1-mercapto-2-methylpropan-2-ylcarbamate. S-2-(Benzyloxy-carbonylamino)-2-methylpropyl ethanethioate (3.00 g, 11.0 mmol) was dissolved into methanol (25 mL). 1 N Sodium hydroxide solution (3 equiv, 32 mL, 32 mmol) was added to the methanol solution in one portion and stirred at RT for 15 min. TLC (20% ethyl acetate in hexanes) analysis of reaction mixture indicated all the starting material was consumed. The organic solvent was removed and the resulting aqueous solution was made acidic (~pH 4) with 1 N HCl, while cooled in an ice bath. The aqueous suspension was extracted with ethyl acetate (2×100 mL) and the combined organic layer washed with brine (50 mL), dried over anh.

MgSO$_4$, filtered and concentrated to a pale yellow oil (2.54 g, 97%). The material was used without further purification.

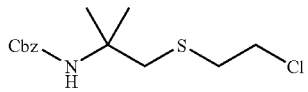 [SMILES: CC(C)(CSCCCl)NC(=O)OCc1ccccc1]

c) Benzyl 1-(2-chloroethylthio)-2-methylpropan-2-ylcarbamate. The crude benzyl 1-mercapto-2-methylpropan-2-ylcarbamate (2.54 g, 10.6 mmol) from the previous reaction was dissolved into DMF (100 mL). Cesium carbonate (7.00 g, 21.35 mmol) was added in one portion to the solution to give a suspension. 1-Bromo-2-chloroethane (1.8 mL, 2 equiv, 21.4 mmol) was added via syringe to the flask. The flask was sealed with a septum and vigorously stirred under nitrogen atmosphere for 16 h. The suspension was filtered through a sintered glass funnel and the solid washed with DMF (2×25 mL). The filtrate was concentrated to an oily residue. This material was mixed with ethyl acetate (150 mL) and water (50 mL). The layers were separated and the organic layer was washed with water (3×50 mL). The organic layer was dried over anh. MgSO$_4$, filtered and concentrated to a yellow oil. Crude weight after drying under high vacuum was 3.03 g (95%). This material was used without further purification.

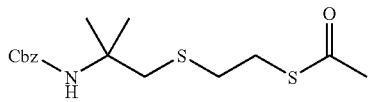 [SMILES: CC(=O)SCCSCC(C)(C)NC(=O)OCc1ccccc1]

d) S-2-(2-(Benzyloxycarbonylamino)-2-methylpropylthio) ethyl ethanethioate. The crude benzyl 1-(2-chloroethylthio)-2-methylpropan-2-ylcarbamate (3.03 g, 10.0 mmol) from the previous reaction was dissolved into DMF (50 mL). Potassium thioacetate (2.28 g, 2 equiv, 20.0 mmol) was added to the flask to give a pale yellow solution. The flask was sealed with a rubber septum and heated at 70° C. overnight. The suspension formed was concentrated to an oily residue. This material was mixed with ethyl acetate (200 mL) and water (50 mL). The layers were separated and the organic layer was washed with water (3×100 mL) and brine (50 mL). The organic layer was dried over anh. MgSO$_4$, filtered and concentrated to a dark yellow oil. The crude weight was 3.49 g. The oil was purified by flash column chromatography on silica gel with 5% ethyl acetate in hexanes as the packing solvent. The eluent was 7.5% ethyl acetate in hexanes (1 L) followed by 10% ethyl acetate in hexanes (1 L). Fractions were pooled and concentrated to give 2.66 g (78%) of a dark yellow oil. $^1$H NMR (CDCl$_3$, 400 MHz): δ 1.37 (s, 6H), 2.33 (s, 3H), 2.66 (m, 2H), 2.97 (s, 2H), 3.03 (m, 2H), 4.89 (br s, 1H), 5.06 (s, 2H), 7.30 (m, 5H). LRMS (ESI+ve) for C$_{16}$H$_{23}$NO$_3$S$_2$. (341.1); found: (M+H$^+$) 342.

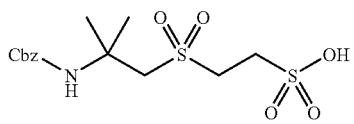 [SMILES: CC(C)(CS(=O)(=O)CCS(=O)(=O)O)NC(=O)OCc1ccccc1]

e) 2-(2-(Benzyloxycarbonylamino)-2-methylpropylsulfonyl)ethanesulfonic acid. S-2-(2-(Benzyloxy-carbonylamino)-2-methylpropylthio)ethyl ethanethioate (2.66 g, 7.8 mmol) was dissolved into 88% formic acid (16 mL) and added in one portion to a premixed solution of 88% formic acid (10 mL) and 30% hydrogen peroxide (10 mL). The reaction was stirred at RT for 17 h. The solvent was removed and the residue was flash chromatographed through silica gel with 30% methanol in DCM as eluent to give a white solid, 2.38 g (80.7%). The product was contaminated with a small amount of 2-(benzyloxycarbonylamino)-2-methylpropane-1-sulfonic acid from the disulfide. This material was used without further purification. LRMS (ESI−ve) for C$_{14}$H$_{21}$NO$_7$S$_2$ (379.1); found: (M−H) 378.

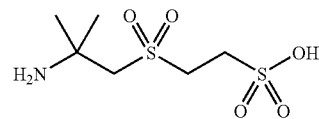

f) 2-(2-Amino-2-methylpropylsulfonyl)ethanesulfonic acid. 2-(2-(Benzyloxy-carbonylamino)-2-methylpropylsulfonyl)ethanesulfonic acid (1.92 g, 5.06 mmol) was dissolved into methanol (80 mL). The flask was flushed with nitrogen for 5 min and 10% Pd/C (200 mg) was added to the solution in one portion. The reaction mixture was degassed under vacuum and flushed with hydrogen (3 times). The reaction was then stirred under atmospheric pressure with a balloon filled with hydrogen for 17 h. The suspension was filtered through a pad of Celite wetted with methanol and the solid was rinsed with methanol (75 mL). The methanol filtrate was discarded and the solid washed with water (4×30 mL) into a fresh filtration flask. The aqueous filtrate was concentrated to give a white solid (0.619 g, 81.0%). This material was used without further purification. $^1$H NMR (DMSO-d6, 400 MHz): δ 1.41 (s, 6H), 2.83 (m, 2H), 3.40 (m, 2H), 3.57 (s, 2H), 7.5 (br s, 3H). LRMS (ESI−ve) for C$_6$H$_{15}$NO$_5$S$_2$ (245.0); found: (M−H) 244.

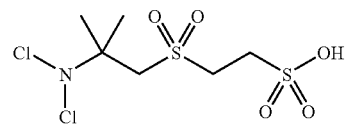 [SMILES: CC(C)(CS(=O)(=O)CCS(=O)(=O)O)N(Cl)Cl]

g) 2-(2-(Dichloroamino)-2-methylpropylsulfonyl)ethanesulfonic acid. 2-(2-2-Aminoethylpropylsulfonyl)ethanesulfonic acid (0.500 g, 2.04 mmol) was dissolved into a mixture of methanol (20 mL) and water (20 mL) which was cooled in an ice bath for 15 min. t-BuOCl (0.60 mL, 2.5 equiv, 5.09 mmol) was added in one portion via syringe to the colorless solution to give a deep yellow solution. The reaction mixture was stirred for 1 h at 0° C., then concentrated under reduced pressure to yield a white solid. This solid was dissolved into water and purified via reverse phase chromatography on a Shimdazu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a white solid, (0.60 g, 94%). $^1$H NMR (D$_2$O, 400 MHz): δ 1.63 (s, 6H), 3.37 (m, 2H), 3.68 (m, 2H), 3.92 (s, 2H). $^{13}$C NMR (CD$_3$OD, 100 MHz): δ 23.6, 24.8, 59.2, 74.2, 172.0. LRMS (ESI−ve) for C$_6$H$_{13}$Cl$_2$N$_2$O$_5$S$_2$ (313.0); found: 312, 314.

Example 9

2-(Dichloroamino)-N,N-2-trimethylpropane-1-sulfonamide

Compound 613

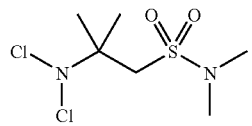

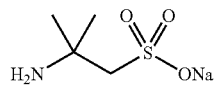

a) Sodium 2-amino-2-methylpropane-1-sulfonate. This compound was prepared from 2-amino-2-methylpropan-1-ol according to the method of D. Braghiroli et al., (*Tet. Lett.*, 1996, 37, 7319).

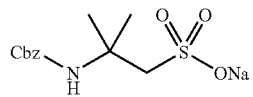

b) Sodium 2-(benzyloxycarbonylamino)-2-methylpropane-1-sulfonate. Sodium 2-amino-2-methylpropane-1-sulfonate (7.5 g, 42.8 mmol) was dissolved into water (100 mL) with sonication. N-(Benzyloxycarbonyloxy)succinimide (0.95 equiv, 10.13 g, 40.7 mmol) was dissolved into THF (50 mL) and added dropwise to the aqueous solution with vigorous stirring. After complete addition, the reaction was left to stir at RT for 16 h. The reaction mixture was concentrated to a small volume to give a biphasic mixture. This mixture was extracted with DCM (5×20 mL) and dried over anh. MgSO$_4$, filtered, and concentrated to give a colorless oil, (11.6 g, quant). This material was used without further purification.

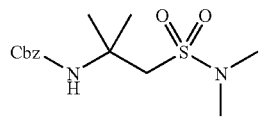 [SMILES: CN(C)S(=O)(=O)CC(C)(C)NC(=O)OCc1ccccc1]

c) Benzyl 1-(N,N-dimethylsulfamoyl)-2-methylpropan-2-ylcarbamate. Sodium 2-(benzyloxycarbonylamino)-2-methylpropane-1-sulfonate (1.42 g, 4.6 mmol) was dissolved into DCE (12 mL) and SOCl$_2$ (2 mL, 6.0 equiv, 27.4 mmol) was added to the solution in one portion. The flask was fitted with a condenser and a drying tube packed with anh. MgSO$_4$. The reaction was heated at 60° C. for an hour and the yellow solution was concentrated under reduced pressure to a yellow oily residue. The residue was suspended into anh. THF (20 mL) and cooled in an ice bath. A 2 M THF solution of dimethylamine (11.5 mL, 5 equiv, 24 mmol) was added dropwise to the ice cold solution of sulfonyl chloride. The reaction was stirred for 1 h at RT and was concentrated to an oily residue which was dissolved into DCM (100 mL). The DCM solution was washed with water (3×20 mL), brine (20 mL), dried over anh. MgSO$_4$, filtered and concentrated to a yellow oil which was flash chromatographed through silica gel with 40% ethyl acetate in hexanes as eluent. Fractions were collected and concentrated to give a pale yellow oil, (0.75 g, 50%). This material was used without further purification for the next step.

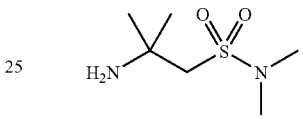

d) 2-Amino-N,N-2-trimethylpropane-1-sulfonamide. Benzyl 1-(N,N-dimethyl-sulfamoyl)-2-methylpropan-2-ylcarbamate (0.75 g, 2.39 mmol) was dissolved into methanol (15 mL). The flask was flushed with nitrogen for 5 min and 10% Pd/C (67 mg) was added to the solution in one portion. The reaction mixture was degassed utilizing a vacuum hydrogen purge (3 times). The reaction was then stirred at atmospheric pressure with a balloon filled with hydrogen for 17 h. The suspension was filtered through a pad of Celite wetted with methanol. The solid was rinsed with methanol (3×20 mL). The filtrate was concentrated to give white solid, (0.39 g, 91%). $^1$H NMR (D$_2$O, 400 MHz): δ 1.31 (s, 6H), 2.86 (s, 6H), 3.22 (s, 2H). LRMS (ESI+ve) for C$_6$H$_{16}$N$_2$O$_2$S (180.1); found: 181 (M+H$^+$). This material was used without further purification.

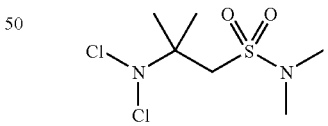

e) 2-(Dichloroamino)-N,N-2-trimethylpronane-1-sulfonamide. 2-Amino-N,N-2-trimethylpropane-1-sulfonamide (0.100 g, 0.5 mmol) was dissolved into methanol (1.5 mL) and cooled in an ice bath for 15 min. t-BuOCl (0.13 mL, 2 equiv, 1.11 mmol) was added in one portion via syringe to the colorless solution to give a deep yellow solution. The reaction mixture was stirred for 1 h at 0° C. The reaction mixture was concentrated to a pale yellow solid. This solid was purified via reverse phase chromatography on a Shimadzu Prep-LC utilizing water/acetonitrile and 0.05% acetic acid as modifier. Fractions were collected monitoring at 215 nm. Fractions were pooled and concentrated via rotovap with the water bath set at 25° C. to give a white solid, (0.12 g, 90%). $^1$H NMR (CD$_3$OD, 400 MHz): δ 1.60 (s, 6H), 2.90 (s, 6H), 3.45 (s, 2H).

Example 10

2-(Dichloroamino)-N,2-dimethylpropane-1-sulfonamide

Compound 626

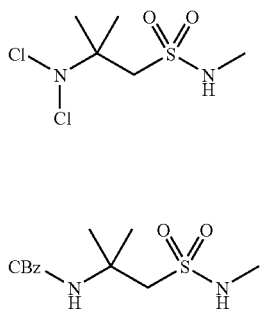

a) Benzyl 2-methyl-1-(N-methylsulfamoyl)propan-2-ylcarbamate. Benzyl 2-methyl-1-(N-methylsulfamoyl)propan-2-ylcarbamate was synthesized following a procedure similar to Example 9, step (c), to yield 1.45 g (74%). LRMS (ESI+ve) for C$_{13}$H$_{20}$N$_2$O$_4$S (300.1); found: 323 (M+Na$^+$).

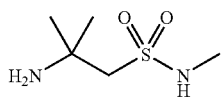

b) 2-Amino-N-2-dimethylpropane-1-sulfonamide. 2-Amino-N2-dimethylpropane-1-sulfonamide was synthesized following a procedure similar to Example 9, step (d), to give a white solid, (0.286 g, 96%). LRMS (ESI+ve) for C$_6$H$_{16}$N$_2$O$_2$S (180.1); found: 181 (M+H$^+$).

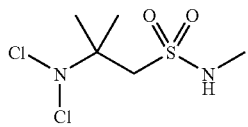

c) 2-(Dichloroamino)-N,2-dimethylpropane-1-sulfonamide. 2-(Dichloro-amino)-N-2-dimethylpropane-1-sulfonamide was synthesized following a procedure similar to Example 9, step (e), to give a white solid, (0.307 g, 76%). $^1$H NMR (CD$_3$OD, 400 MHz): δ 1.63 (s, 6H), 3.30 (s, 3H), 3.85 (s, 2H).

Example 11

N-(2-(Dichloroamino)-2-methylpropylsulfonyl)acetamide

Compound 627

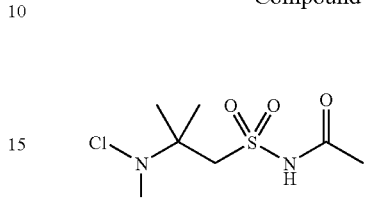

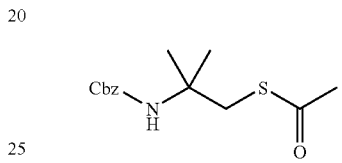

a) S-2-(Benzyloxycarbonylamino)-2-methylpropyl ethanethioate. Obtained as described in Example 8, step (a).

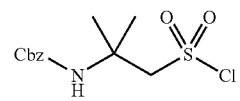

b) Benzyl 1-(chlorosulfonyl)-2-methylpropan-2-ylcarbamate. S-2-(Benzyloxy-carbonylamino)-2-methylpropyl ethanethioate (3.5 g, 12.4 mmol) was dissolved into DCM (50 mL) and cooled in an ice bath for 15 minutes. A solution of bleach (5% NaOCl, 18.0 mL, 3 equiv, 37.3 mmol) was acidified to ~pH 5 with 1 M HCl (38 mL) in an ice bath. The ice cold solution of HOCl was added to the DCM solution in one portion. This biphasic mixture was vigorously stirred for 30 min at 0° C. The mixture was poured into a separatory funnel and the organic layer was separated and dried over anh. MgSO$_4$, filtered and concentrated to a pale yellow oil which was dried under high vacuum for 2 h. This material was used without further purification, (3.56 g, 94%).

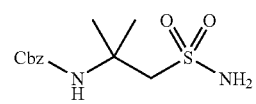

c) Benzyl 2-methyl-1-sulfamoylpropan-2-ylcarbamate. The crude benzyl 1-(chlorosulfonyl)-2-methylpropan-2-ylcarbamate (3.56 g, 11.6 mmol) was dissolved into DCM (50 mL) and a 30% solution of ammonia in water (6.8 mL, 5 equiv, 58.0 mmol) was added at 0° C. The reaction was vigorously stirred for 1 h. The mixture was poured into a separatory funnel and the layers separated. The organic layer was washed with water (3×10 mL) and brine (10 mL), dried over anh. MgSO$_4$, filtered and concentrated to a yellow oil which solidified while drying under high vacuum (2.94 g, 82.6%). The crude solid was used without further purification.

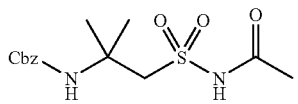

d) Benzyl 1-(N-acetylsulfamoyl)-2-methylpropan-2-yl-carbamate. Benzyl 2-methyl-1-sulfamoylpropan-2-ylcarbamate (2.94 g, 10.3 mmol) was dissolved into DCM (50 mL) and cooled in an ice bath. Diisopropylethylamine (1.5 equiv, 2.70 mL, 15.4 mmol) and acetic anhydride (1.76 mL, 15.4 mmol) was added to the reaction mixture via syringe. The reaction was stirred under nitrogen for 16 h. The reaction mixture was washed successively with water (3×20 mL), brine (10 mL), dried over anh. MgSO$_4$, filtered and concentrated to a yellow oil which solidified on standing. The solid was purified by flash chromatography on silica gel utilizing 80% ethyl acetate in hexanes as eluent to give a white solid, (2.51 g, 74%). $^1$H NMR (CDCl$_3$, 400 MHz): δ 1.52 (br s, 6H), 2.08 (s, 3H), 3.92 (br s, 2H), 5.08 (br s, 2H), 5.19 (br s, 1H), 7.34 (m, 5H), 8.50 (br s, 1H). LRMS (ESI–ve) for C$_{14}$H$_{20}$N$_2$O$_5$S (328.1); found: 327.

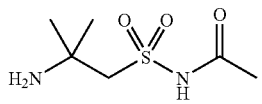

e) N-(2-Amino-2-methylpropylsulfonyl)acetamide. Benzyl 1-(N-acetylsulfamoyl)-2-methylpropan-2-ylcarbamate (1.00 g, 3.0 mmol) was dissolved into acetic acid (25 mL) and DCM (25 mL) by sonication. The flask was flushed with nitrogen for 5 min and 10% Pd/C (250 mg) was added to the solution in one portion. The reaction mixture was degassed under vacuum and flushed with hydrogen (3 times). The reaction was then stirred under atmospheric pressure with a balloon filled with hydrogen for 17 h. The suspension was filtered through a pad of Celite wetted with methanol. The solid was rinsed with water (3×20 mL) and methanol (3×20 mL). The filtrate was concentrated to give white solid (0.6190 g, 81.0%). This material was used without further purification. LRMS (ESI–ve) for C$_6$H$_{14}$N$_2$O$_3$S (194); found: 193.

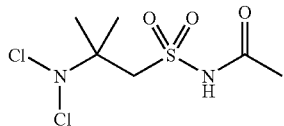

f) N-(2-(Dichloroamino)-2-methylpropylsulfonyl)acetamide. N-(2-amino-2-methyl-propylsulfonyl)acetamide (0.619 g, 2.43 mmol) was dissolved into a mixture of methanol (53 mL) and water (13 mL), which was cooled in an ice bath for 15 min. t-BuOCl (0.70 mL, 2.5 equiv, 6.21 mmol) was added in portion via syringe to the colorless solution to give a deep yellow solution. The reaction mixture was stirred for 1 h at 0° C. The reaction mixture was concentrated and the crude material was purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated under reduced pressure at 25° C. to give a white solid, (0.535 g, 84%). $^1$H NMR (CD$_3$OD, 400 MHz): δ 1.60 (s, 6H), 2.08 (s, 3H), 3.97 (s, 2H). $^{13}$C NMR (CD$_3$OD, 100 MHz): δ 23.6, 24.8, 59.2, 74.2, 172.0. LRMS (ESI–ve) for C$_6$H$_{12}$Cl$_2$N$_2$O$_3$S (262.0); found: 261, 263.

Example 12

(1-(Dichloroamino)cycloheptyl)methanesulfonic acid

Compound 601

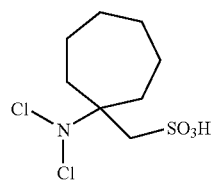

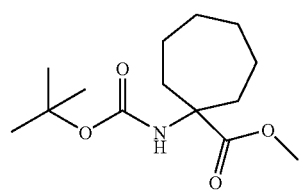 [SMILES: COC(=O)C1(NC(=O)OC(C)(C)C)CCCCCC1]

a) Methyl-1-(t-butoxycarbonylamino)cycloheptanecarboxylate. To a solution of 1-(t-butoxycarbonylamino)cycloheptanecarboxylic acid (Infarmatik Inc.) (5 g, 19.4 mmol) in anhydrous THF (50 mL), TMS-diazomethane (38.9 mmol, 38.9 mL) was added. After stirring at RT overnight the reaction mixture was concentrated and taken up in EtOAc. It was washed with sat. NaHCO$_3$, water, then brine, and was concentrated to yield the crude methyl ester which was used without further purification for the next step. Yield 4.2 g (94%).

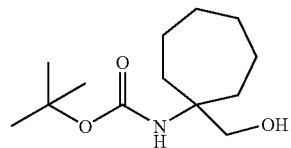 [SMILES: CC(C)(C)OC(=O)NC1(CO)CCCCCC1]

b) t-Butyl-1-(hydroxymethyl)cycloheptylcarbamate. A solution of methyl 1-(t-butoxycarbonylamino)cycloheptanecarboxylate (4 g, 14.7 mmol) in 100 mL THF was cooled to 0° C. and lithium borohydride (1.6 g, 73.7 mmol) was added. Two small portions of methanol (0.5 mL) were added, dropwise, at 3 h and 5 h. The reaction mixture was warmed to RT slowly and stirred vigorously for 20 h. The reaction was quenched by the addition of sat. NH$_4$Cl (50 mL), followed by water (50 mL) and extracted with EtOAc (5×100 mL). The organic layers were combined, dried over Na$_2$SO$_4$, and evaporated. The crude alcohol was purified over silica gel using 20% EtOAc/hexane to afford 3.8 g (94%) of the title compound.

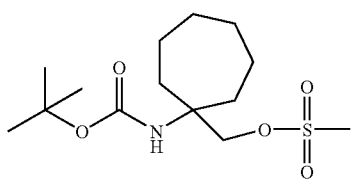 [SMILES: CC(C)(C)OC(=O)NC1(COS(C)(=O)=O)CCCCCC1]

c) (1-(t-Butoxycarbonylamino)cycloheptyl)methyl methanesulfonate. t-Butyl-1-(hydroxymethyl)cycloheptylcarbamate (3.5 g, 14.4 mmol) was dissolved in methylene chloride (50 mL) and triethylamine (2.41 mL, 17.3 mmol) was added. The mixture was cooled in ice and methanesulfonyl chloride (1.45 mL, 17.3 mmol) was added dropwise. The mixture was stirred overnight at RT, then concentrated in vacuo and suspended in ethyl acetate (100 mL). It was washed with water and 1 N HCl. The organic layer was dried over sodium sulfate and concentrated. The residue was purified over silica gel using 30% EtOAc/hexane as eluent to afford the title compound as a white powder (2 g, 43%). $^1$H NMR (CDCl$_3$, 400 MHz) δ 1.42 (s, 9H), 1.53-1.56 (m, 8H), 1.62-1.68 (m, 2H), 1.85-1.91 (m, 2H), 2.99 (s, 3H), 4.33 (s, 2H), 4.41 (br s, 1H).

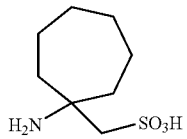

d) (1-Aminocycloheptyl)methanesulfonic acid. (t-Butoxycarbonyl-amino)cycloheptyl)-methyl methanesulfonate (3 g, 9.3 mmol) was dissolved in 4 M HCl in 1,4-dioxane (30 mL) and the solution stirred for 1 h. The solution was evaporated, the residue dissolved in H$_2$O (10 ml), and 1M Na$_2$SO$_3$ (18.6 mL, 18.6 mmol) was added. The solution was stirred for 48 h, evaporated, and the resulting white residue was extracted with warm EtOH (4×50 mL). The ethanol portions were combined and evaporated. The crude material was purified by flash chromatography (30% MeOH/CH$_2$Cl$_2$) to give the title compound as a white solid (700 mg, 36%). LCMS (ESI–Neg) for C$_8$H$_{17}$NO$_3$S (207.09); found: 206 (M–H).

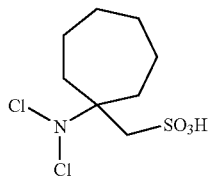 [SMILES: O=S(=O)(O)CC1(N(Cl)Cl)CCCCCC1]

e) (1-(Dichloroamino)cycloheptyl)methanesulfonic acid. Commercial bleach (8.1 ml, 5% NaOCl) was adjusted to pH 5 with dropwise addition of 6 M HCl and was added dropwise to a solution of 1-(aminocycloheptyl)methanesulfonic acid (700 mg, 2.16 mmol) in H$_2$O (5 ml). The solution was stirred for 1 h, until the starting aminosulfonic acid had been completely consumed (followed by LCMS). The solution was evaporated and the residue was subjected to column chromatography over silica gel using 10% MeOH/CH$_2$Cl$_2$ to afford the dichloramine as a white powder (0.3 g, 51%). $^1$H NMR (CD$_3$OD, 400 MHz) δ 1.56-1.67 (m, 8H), 1.99-2.16 (m, 4H), 3.48 (s, 2H). LCMS (ESI–Neg) for C$_8$H$_{15}$C$_{12}$NO$_3$S (276.18); found: 275 (M–H).

Example 13

2-(Dichloroamino)-2-methylcyclohexane-1-sulfonic acid

Compound 611

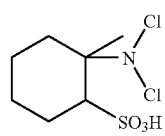

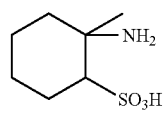

a) 2-Amino-2-methylcyclohexane-1-sulfonic acid. Prepared according to the method described in M. F. Cordero et al., *Eur. J. Org. Chem.*, 2002, 1407. Yield: 2.4 g, 52%. LCMS (ESI–Neg) for C$_7$H$_{15}$NO$_3$S (193.08); found: 192 (M–H).

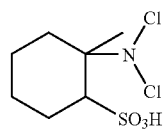

b) 2-(Dichloroamino)-2-methylcyclohexane-1-sulfonic acid. Prepared analogously to Example 6, step (e), by chlorination of 2-amino-2-methylcyclohexane-1-sulfonic acid using t-butyl hypochlorite. Yield: 0.75 g, 82%. $^1$H NMR (CD$_3$OD, 400 MHz) δ 1.35-1.40 (m, 2H), 1.61 (s, 3H), 1.77-

1.91 (m, 2H), 1.93-2.1 (m, 2H), 2.33-2.42 (m, 2H), 3.41-3.44 (m, 1H). LCMS (ESI–Neg) for C$_7$H$_{13}$C$_{12}$NO$_3$S (261); found: 260 (M–H).

Example 14

(1-Acetyl-4-(dichloroamino)piperidin-4-yl)methanesulfonic acid

Compound 637

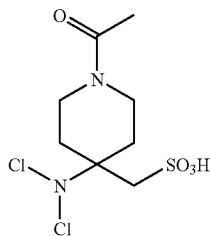 [SMILES: CC(=O)N1CCC(CS(=O)(=O)O)(N(Cl)Cl)CC1]

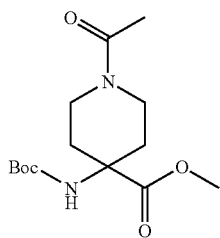 [SMILES: COC(=O)C1(NC(=O)OC(C)(C)C)CCN(C(C)=O)CC1]

a) Methyl 1-acetyl-4-(t-butoxycarbonylamino)piperidine-4-carboxylate. Methyl 1-acetyl-4-(t-butoxycarbonylamino)piperidine-4-carboxylate was synthesized from methyl 4-(t-butoxycarbonylamino)piperidine-4-carboxylate following a similar procedure to that outlined in Example 11, step (d) for benzyl 1-(N-acetylsulfamoyl)-2-methylpropan-2-ylcarbamate to give a white foam, 5.28 g (91%). This material was used without further purification in the next step. $^1$H NMR (CDCl$_3$, 400 MHz): δ 1.44 (s, 9H), 1.83-1.97 (m, 2H), 2.10 (s, 3H), 2.14-2.17 (m, 2H), 3.12-3.18 (m, 1H), 3.35-3.42 (m, 1H), 3.64-3.70 (m, 1H), 3.74 (s, 3H), 4.15-4.18 (m, 1H). LRMS (ESI+ve) for C$_{14}$H$_{24}$N$_2$O$_5$ (300.2); found: 301 (M+H$^+$).

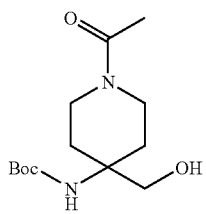 [SMILES: CC(=O)N1CCC(CO)(NC(=O)OC(C)(C)C)CC1]

b) t-Butyl 1-acetyl-4-(hydroxymethyl)piperidin-4-ylcarbamate. t-Butyl 1-acetyl-4-(hydroxymethyl)piperidin-4-ylcarbamate was synthesized from methyl 1-acetyl-4-(t-butoxycarbonylamino)piperidine-4-carboxylate following a procedure similar to the synthesis of 2-(t-butylcarboxyamino)-2-methyl-3-phenylpropan-1-ol as described in Example 1, step (b) to give a white solid, (4.51 g, 94%). This material was used without further purification in the next step.

$^1$H NMR (CDCl$_3$, 400 MHz): δ 1.44 (s, 9H), 1.55-1.82 (m, 3H), 2.04-2.10 (m, 1H), 2.10 (s, 3H), 3.15-3.22 (m, 1H), 3.32-3.39 (m, 1H), 3.54-3.51 (m, 1H), 3.70 (s, 2H), 4.04-4.08 (m, 1H), 4.60 (br s, 1H). LRMS (ESI+ve) for C$_{13}$H$_{24}$N$_2$O$_4$ (272.2); found: 273 (M+H$^+$).

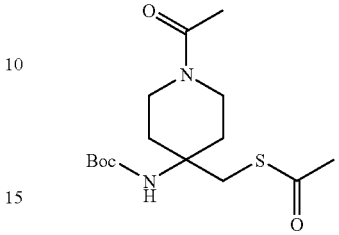

c) S-(1-Acetyl-4-(t-butoxycarbonylamino)piperidin-4-yl)methyl ethanethioate. S-(1-Acetyl-4-(t-butoxycarbonylamino)piperidin-4-yl)methyl ethanethioate was synthesized from t-butyl 1-acetyl-4-(hydroxymethyl)piperidin-4-ylcarbamate following a procedure similar to the synthesis of S-2-(benzyloxycarbonylamino)-2-methylpropyl ethanethioate as shown in Example 8, step (a) to give a crude yellow oil which was used without purification in the next step.

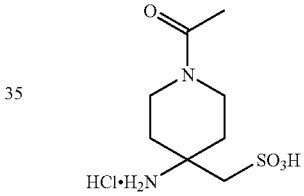

d) (1-Acetyl-4-aminopiperidin-4-yl)methanesulfonic acid hydrochloride. S-(1-Acetyl-4-(t-butoxycarbonylamino)piperidin-4-yl)methyl ethanethioate dissolved into acetic acid (32 mL) and added to a premixed solution of acetic acid (16 mL) and 30% H$_2$O$_2$ (16 mL) and stirred at RT for 72 h. 10% Pd/C (52.3 mg) was added to the reaction and stirred for 4 h to decompose excess H$_2$O$_2$. The suspension was filtered and the filtrate was concentrated under reduced pressure. The residue was suspended into 4M HCl in 1,4-dioxane (30 mL) and stirred at RT for 16 h. The solvent was removed and the residue mixed with ethyl acetate (200 mL) and water (50 mL) The layers were separated and the organic layer was extracted with water (2×50 mL). The combined aqueous layer was washed with ethyl acetate (3×200 mL) and concentrated to an oily residue which was dried under high vacuum to yield a product with a crude weight of 4.5 g. The crude material was purified via reverse phase chromatography on a Shimadzu Prep-LC utilizing water/methanol and 10 mmol NH$_4$OAc as modifier. Fractions were collected monitoring UV absorbance at 215 nm. Fractions were pooled and concentrated under reduced pressure at 25° C. to give an impure white solid (1.9 g, 43.8%).

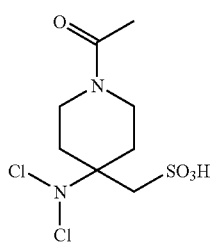 [SMILES: CC(=O)N1CCC(CS(=O)(=O)O)(N(Cl)Cl)CC1]

e) 2-(Dichloroamino)-N,2-dimethylpropane-1-sulfonamide. (1-acetyl-4-(dichloroamino)piperidin-4-yl)methanesulfonic acid was synthesized following a procedure similar to Example 9, step (e), to give a white solid (57.2 mg, 5.2%). $^1$H NMR (D$_2$O, 400 MHz) δ 2.08 (s, 3H), 2.24 (m, 4H), 3.02-3.15 (m, 1H), 3.42-3.48 (m, 1H), 3.63 (s, 2H), 3.70-3.76 (m, 1H), 4.05-4.15 (m, 1H). LRMS (ESI–ve) for C$_8$H$_{14}$Cl$_2$N$_2$O$_4$S (304.2); found: (M–H) 303, 305.

Example 15

Preparation of Additional Compounds

In a manner similar to the procedures of Examples 1 through 14 or by analogous procedures known in the art, the following compounds are prepared:

2-(dichloroamino)-2-trifluoromethyl-3,3,3-trifluoropropane-1-sulfonic acid
2-(chloro(methyl)amino)-2-methylpropane-1-sulfonic acid
2-(chloro(methyl)amino)-1,1,2-trimethylpropane-1-sulfonic acid
3-(dichloro amino)-2,2,3-trimethylbutane-1-sulfonic acid
3-(chloro(methyl)amino)-3-methylbutane-1-sulfonic acid
2-(dichloroamino)-2-trifluoromethylpropane-1-sulfonic acid
4-(dichloroamino)-4-methylpentane-1-sulfonic acid
(4-(dichloroamino)-1-methylpiperidin-4-yl)methanesulfonic acid
(4-(dichloroamino)tetrahydro-2H-pyran-4-yl)methanesulfonic acid
2-(2-(dichloroamino)-2-methylpropylthio)ethanesulfonic acid
2-(2-(dichloroamino)-2-methylpropylsulfonyl)ethanesulfonic acid
2-(2-(dichloroamino)-2-methylpropoxy)ethanesulfonic acid.

Example 16

General Procedure for Preparing Monochloro-Amino Compounds

The amino acid or a salt of the amino acid (powder) is added into a basic OCl$^-$ solution (pH>8) or an OCl$^-$ solution in a phosphate buffer, typically at pH 8, at a 1:1 molar ratio of OCl$^-$:amino acid. The mixture solution is stirred for about 15 minutes. The product is identified and the completion of the reaction is followed by an UV-vis spectrophotometer or by LCMS. The pH of the solution is adjusted with dilute hydrochloric acid or sodium hydroxide solution to the desired pH value. However, the final pH should not be lower than 7.5 due to the disproportionation reaction of monohalo-compounds. The concentration of the solution is determined on UV spectrophotometer by using the corresponding molar absorptivity at the λ$_{max}$ near 250 nm.

Example 17

General Procedure for Preparing Dichloro-Amino Compounds

The amino acid or a salt of the amino acid (powder) is added into an acidic HOCl solution (pH ~5) at a 2:1 molar ratio of HOCl:amino acid. The mixture is stirred for about 60 minutes. The product is identified and the completion of the reaction is followed by an UV-vis spectrophotometer or by LCMS. The pH of the solution is adjusted with dilute hydrochloric acid or sodium hydroxide solution to the desired pH value. The concentration of the solution is determined on UV spectrophotometer by using the corresponding molar absorptivity at the λ$_{max}$ near 304 nm.

Example 18

General Procedure for Preparing Monobromo-Amino Compounds

The amino acid or a salt of the amino acid is added to a vigorously stirred solution of Br$_2$ in 0.1 M NaOH at a 1:1 molar ratio of bromine:amino acid. The mixture is stirred for about 60 minutes, and the product identified followed by a UV-vis spectrophotometer or by LCMS. The product is purified by RP-HPLC and the concentration of a solution is determined on the UV spectrophotometer by using the corresponding molar absorptivity at the λ$_{max}$ near 280 nm.

Example 19

General Procedure for Preparing Dibromo-Amino Compounds

Following the procedure of Chinake et al. (Chinake, C. R.; Simoyi, R. H. J. Phys. Chem. B 1998, 102, 10490-10497), the amino acid or a salt of the amino acid (powder) is added into an acidic HBr solution (pH 0) and sodium bromate is added at a 100:1 molar ratio of BrO$_3^-$:amine. The mixture is stirred for about 10 minutes, and the product identified followed by a UV-vis spectrophotometer or by LCMS. The product is purified by RP-HPLC and the concentration of a solution is determined on the UV spectrophotometer by using the corresponding molar absorptivity at the λ$_{max}$ near 340 nm.

Example 20

General Procedure for Preparing Monochloroaminosulfonate Compounds in Organic Solvents The sodium salt of the aminosulfonate anion is dissolved in an organic solvent (methanol or ethanol preferred) and t-butylhypochlorite is added in a 1:1 molar ratio. The mixture is stirred for about 1 hour with the progress of the reaction followed by LCMS chromatography. The solution is evaporated and the residue purified by reverse-phase ($C_8$ or $C_{18}$) HPLC chromatography.

Example 21

General Procedure for Preparing Dichloroaminosulfonate Compounds in Organic Solvents The aminosulfonate (zwitterion) or the sodium salt of the aminosulfonate anion is dissolved in an organic solvent (methanol or ethanol preferred) and t-butylhypochlorite is added in a 2:1 molar ratio. The mixture is stirred for about 1 h with the progress of the reaction followed by LCMS chromatography. The solution is evaporated and the residue purified by reverse-phase ($C_{18}$) HPLC chromatography.

TABLE 1

| Microorganism | Minimum Bactericidal Concentration [MBC] [≧99.9% Bacterial Kill] | |
|---|---|---|
| | Mm | µg/mL |
| E. coli [ATCC 25922] | 0.19 | 0.65 |
| P. aeruginosa [ATCC 27853] | 3.9 | 1.3 |
| S. aureus [ATCC 29213] | 15.6 | 5.2 | b) Table 2 shows data obtained according to the method described above for additional compounds. Data shown are the Minimum Biocidal Concentration (MBC) (≧99.9% kill) in µg/mL.

TABLE 2

| | E. coli 25922 | | S. aureus 29213 | | C. albicans 10231 | | P. aeruginosa 27853 | |
|---|---|---|---|---|---|---|---|---|
| Cmpd | pH 4 (Sal) | pH 7 (PBS) | pH 4 (Sal) | pH 7 (PBS) | pH 4 (Sal) | pH 7 (PBS) | pH 4 (Sal) | pH 7 (PBS) |
| 601 | | | 0.25* | | | | 0.5# | |
| 611 | | | 1* | 64* | 0.5+ | 64+ | 1# | 32# |
| 614 | | | 1* | 128* | 4+ | 512+ | 4# | 256# |
| 625 | 4 | | 8 | | 16 | | | |
| 626 | 4 | | 0.5 | | 8 | | | |
| 627 | 2 | | 1 | | 64 | | | |
| 628 | 2 | | 2 | | 64 | | | |
| 630 | 4 | | 8 | | 64 | | | |
| 637 | 16 | | 4 | | 128 | | | |

*S. aureus MCC 91731
P. aeruginosa MCC 4438
+C. albicans MCC 50319

Example 22

Antimicrobial Activity

To determine antimicrobial activity, we use *Escherichia coli* (ATCC 25922), *Staphylococcus aureus* (ATCC 29213), *Pseudomonas aeruginosa* (ATCC 27853), and *Candida albicans* (ATCC 10231) in primary screening. In addition, we use *Staphylococcus aureus* (MCC 91731), *Pseudomonas aeruginosa* (MCC 4438), and *Candida albicans* (MCC 50319), provided by Alcon Laboratories, Fort Worth, Tex. The microbial cultures are diluted in sterile saline pH 4 to prepare inocula. Test compounds are titrated by stepwise two-fold dilutions in sterile saline pH 4, $1.0 \times 10^5$ to $1.0 \times 10^6$ Colony Forming Units (CFU)/mL bacteriamicrobe is added to each tube, mixed by gentle vortexing, and then incubated at room temperature for 1 h. Bacterial plating on Petri dishes (Tryptic Soy agar or Saboraud's Dextrose agar) is performed immediately after the designated exposure after neutralization of the test article dilutions in Dey-Engley Broth. Plates are incubated at 37° C., and the numbers of bacteria are counted by direct colony count to quantitate the surviving bacteria as CFU/mL. Positive growth controls are made with sterile 0.9% saline. All compounds are tested three times. The results are tabulated to show the comparison of antimicrobial effectiveness range of the compounds.

a) At pH 4.0, 3-(4-chlorophenyl)-2-(dichloroamino)-2-methylpropane-1-sulfonic acid (Cmpd 570) shows an effective antimicrobial activity at 60 min in the µM concentration range (Table 1).

Example 23

Cytotoxicity

Cytotoxicity is assessed by a colorimetric assay system using the Dojindo™ cell counting kit containing 2-(2-methoxy-4-nitrophenyl)-3-(4-nitrophenyl)—S—(2,4-disulfophenyl)-2H-tetrazolium, monosodium salt (WST-8). In this assay, the WST-8 reagent is bioreduced by cellular dehydrogenases to a formazan product that is highly soluble in tissue culture medium. The orange formazan, which is produced only by live cells, is a direct measure of cell viability and can be read spectrophotometrically (for example, evaluation of a soluble tetrazolium/formazan assay for cell growth and drug sensitivity in culture using human and other tumor cell lines is described by Scudiero D A, Shoemaker R A H, Paul K D, Monks A, Tierney S, Nofziger T H, Currens M J, Seniff D, Boyd M R. Cancer Res. 1988 Sep. 1; 48(17):4827-33). Similar approaches for determining the cell viability are known in the art.

In a standard assay, mouse fibroblast cells (ATCC CCL-1, L929), are cultured in Minimum Essential Medium, α-medium supplemented with 10% heat inactivated fetal bovine serum, L-glutamine, penicillin and streptomycin. Cells are trypsinized and counted under the microscope and seeded at $1.5 \times 10^4$ total cells per 100 µL per well of a flat-bottom 96-well plate in order to achieve ~80% confluence after overnight incubation at 37° C. On the day of the assay, the tissue culture medium is removed and replaced with 30 µL of fresh medium.

Test articles are prepared as 2-fold serial dilutions and 170 μL, of each dilution is added into each of 4-wells (total volume per well=200 μL). The test plate is then returned to the 37° C. incubator for 60 min. Immediately after the exposed time, test article from each well is replaced with 200 μL of fresh media. Plates are incubated at 37° C. for 18-20 hours. The following day growth medium is replaced with 100 μL/well of fresh medium containing 10/100 μL WST-8 reagent. Cells are incubated under growth conditions (5% $CO_2$ at 37° C. humidified incubator), protected from light, until color development is achieved (usually 1-4 hours). Absorbance is read at 450 nm with reference wavelength at 750 nm using Molecular Device SpectraMax M5 plate reader. Untreated or vehicle only treated cells receiving WST-8 reagent serve as positive cell proliferation controls.

a) When cell inhibitory concentration toxicity index ($IC_{50}$) was determined (measured as the chemical concentration resulting in 50% inhibition of growth), the $IC_{50}$ of 3-(4-chlorophenyl)-2-(dichloroamino)-2-methylpropane-1-sulfonic acid was at 0.2 mM.

b) Table 3 shows data ($CT_{50}$, in mM) obtained according to the method described above for additional compounds. The $CT_{50}$ value for each compound was calculated from the absorbance values ($A_{450-750}$) and is defined as the concentration of test article that results in survival of 50% of the cells following treatment. The absorbance $A_{450-750}$ from each well of untreated cells and from each well within the dilution series was measured. To calculate the $CT_{50}$ for each compound, all compound concentrations were first log-transformed using GraphPad Prism4 (ver 4.03) software. Next, a non-linear regression (curve fit) analysis was performed on all the absorbance data measured from the dilution series, including the absorbance data obtained from wells of the untreated control cells. For each dilution within the dilution series, an average $A_{450-750}$ was calculated from the four replicate wells. The average $A_{450-750}$ data were plotted on a y-axis against the log-transformed compound concentration on the x-axis, and the $CT_{50}$ value calculated from the resulting best-fit curve.

TABLE 3

| Cmpd | L929 cells pH 4 (Sal) | L929 cells pH 7 (PBS) |
|---|---|---|
| 611 | 0.25 | 4.6 |
| 614 | 0.43 | 4.6 |
| 625 | 2.6 | ND |

ND = not done

Example 24

Concentration Dependence of Antimicrobial Activity and Toxicity

The results of our discovery provide support for antimicrobial activity of 3-(4-chlorophenyl)-2-(dichloroamino)-2-methylpropane-1-sulfonic acid in 0.9% saline at pH 3.5. These antimicrobial activities are determined to be considerable in a μM range and increased significantly by increasing the concentration and or exposure time. In contrast, cell toxicity is seen at a 1000-fold higher range in the mM range. 3-(4-Chlorophenyl)-2-(dichloroamino)-2-methylpropane-1-sulfonic acid treated cells are able to tolerate the treatment and be able to go through normal cell proliferation cycles as compared to untreated control cells in our XTT assay.

Example 25

Preparation of 3-(4-chlorophenyl)-2-(dichloroamino)-2-methylpropane-1-sulfonic Acid Sodium Salt Solutions 3-(4-Chlorophenyl)-2-(dichloroamino)-2-methylpropane-1-sulfonic acid sodium salt solutions with a concentration of 10.3 mM at pH 4 is prepared in 0.9% saline. The spectra and the concentrations of the solutions are measured on the UV-vis spectrometer.

Solutions with varying pH values can be prepared in a similar manner within the pH range of 2 to 8. If properly stored the stability of all solutions may be monitored by their UV spectra.

Example 26

Synergistic Antiviral Effect

Synergistic antiviral effect of an isotonic solution of a 1:1 combination of hypochlorous acid and 3-(4-chlorophenyl)-2-(dichloroamino)-2-methylpropane-1-sulfonic acid sodium salt is observed when an equal volume of human adenovirus type 5 (Ad5, McEwen strain) containing solution is mixed with it. The mixture is then incubated at 37° C. for 1 hr and then diluted in tissue culture medium (Dulbecco's Modified Eagle Medium [DMEM] containing heat inactivated 2% fetal bovine serum). The resulting mixtures are then diluted in 10-fold serial dilutions using the same diluent mentioned above. Each diluted mixture (0.1 mL) is inoculated on to a A549 cell monolayer grown in 12 well plates (cell source, ATTC) and allowed to adsorb for 1 h. The inoculum is removed and the monolayer rinsed with diluent and agarose/DMEM overlay applied. The plates are incubated at 37° C. in 5% $CO_2$ atmosphere for 6 days. The monolayers are then fixed, stained and the plaques counted.

Similar antiviral affects are observed with an isotonic solution of a 1:1 combination of hypochlorous acid and a compound of formula I. It is observed that the antiviral effect of certain combinations of hypochlorous acid and a compound covered in formula I is more than additive.

Example 27

Solutions for Wound Treatment

| | |
|---|---|
| 1 mM | 3-(4-chlorophenyl)-2-(dichloroamino)-2-methylpropane-1-sulfonic acid salt |
| 0.9% | NaCl |
| 4 mM | 3-(4-chlorophenyl)-2-(dichloroamino)-2-methylpropane-1 sulfonic acid salt |
| 0.9% | NaCl |
| 12 mM | 3-(4-chlorophenyl)-2-(dichloroamino)-2-methylpropane-1-sulfonic acid salt |
| 0.9% | NaCl |
| 2 mM | HOCl |
| 1 mM | 3-(4-chlorophenyl)-2-(dichloroamino)-2-methylpropane-1-sulfonic acid salt |
| 0.9% | NaCl |
| 2 mM | HOCl |
| 4 mM | 3-(4-chlorophenyl)-2-(dichloroamino)-2-methylpropane-1-sulfonic acid salt |
| 0.9% | NaCl |
| 2 mM | HOCl |
| 12 mM | 3-(4-chlorophenyl)-2-(dichloroamino)-2-methylpropane-1-sulfonic acid salt |
| 0.9% | NaCl |

What is claimed:

1. A compound having the formula I:

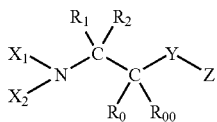

wherein:

$X_1$ is chloro or bromo;

$X_2$ is hydrogen or is selected from the group consisting of chloro, bromo, $(C_{1-5})$alkyl, $(C_{3-6})$cycloalkyl, $(C_{3-6})$cycloalkyl$(C_{1-3})$alkyl and halo$(C_{1-5})$alkyl;

$R_1$ and $R_2$ are each independently selected from the group consisting of $(C_{1-5})$alkyl, halo$(C_{1-5})$alkyl, $(C_{3-12})$cycloalkyl, $(C_{3-6})$cycloalkyl$(C_{1-3})$alkyl, $(C_{6-10})$aryl$(C_{1-4})$alkyl, $(C_{6-14})$aryl and heterocycloalkyl containing 2-10 carbon atoms and 1 to 4 heteroatoms selected from N, O or S, or $R_1$ and $R_2$ together with the carbon atom to which they are attached to form a $(C_{3-12})$carbocyclic or $(C_{3-12})$ heterocyclyl with at least one heteroatom selected from N, O, or S in the ring;

$R_0$ and $R_{00}$ are each independently hydrogen, fluoro or the same as $R_1$ and $R_2$;

Y is a member selected from a single bond, —O—, and a divalent $(C_{1-18})$alkylenyl group in which optionally one or two methylene groups are replaced with a mono- or di-substituted methylene group, or optionally where one or two methylene groups are replaced with 1 or 2 —NR'—, —O—, —S—, —S(=O)—, >C=O, —C(=O)O—, —OC(=O)—, —C(=O)NH—, —NHC(=O)—, —C(=O)NR'—, —NR'C(=O)—, —S(=O)$_2$—, —S(=O)$_2$NR'—, —S(=O)$_2$NH—, —NR'S(=O)$_2$—, or —NHS(=O)$_2$—, where R' is hydrogen or is selected from the group consisting of Cl, Br, $(C_{1-5})$alkyl, $(C_{3-6})$cycloalkyl, $(C_{6-10})$aryl, $(C_{6-10})$aryl$(C_{1-4})$alkyl, $(C_{1-5})$alkylNHC(=O)—, $(C_{1-5})$alkoxyC(=O)—, $R^aR^bNC$(=O)—, $(C_{1-5})$alkylC(=O)—, $(C_{6-10})$arylC(=O)—, $(C_{6-10})$aryl$(C_{1-4})$alkylC(=O)—, $(C_{6-14})$aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, $(C_{1-5})$alkyl, $(C_{3-6})$cycloalkyl, $(C_{1-5})$alkylNHC(=O)—, $(C_{1-5})$alkylC(=O)—, $(C_{6-14})$aryl, $(C_{6-10})$aryl$(C_{1-4})$alkyl, heteroaryl comprising 4 to 10 ring atoms with at least one heteroatom selected from O, S and N in the ring, or heterocyclyl$(C_{1-4})$ alkyl, the heterocycloalkyl group containing 2-10 carbon atoms and 1 to 4 heteroatoms selected from N, O or S;

wherein when $R_1$ is $(C_{1-5})$alkyl or $R_1$ and $R_2$ together with the carbon atom to which they attach form a $(C_{3-6})$cycloalkyl, then $X_2$ must be $(C_{1-5})$alkyl, $(C_{3-6})$cycloalkyl, $(C_{3-6})$cycloalkyl$(C_{1-3})$alkyl, or halo$(C_{1-5})$alkyl; or when $R_1$ is $(C_{1-5})$alkyl, then $R_2$ must be halo$(C_{1-5})$alkyl, $(C_{3-12})$cycloalkyl or $(C_{3-6})$cycloalkyl-$C_{1-3}$ alkyl; or when $R_1$ is $(C_{1-5})$alkyl or $R_1$ and $R_2$ together with the carbon atom to which they attach form a $(C_{3-6})$cycloalkyl, then Y must be —O— or a divalent $(C_{1-18})$ alkylenyl group wherein one or two methylene groups are replaced with a substituted methylene group or by —NR'—, —O—, —S—, —S(=O)— or —S(=O)$_2$—, where R' is hydrogen or is selected from the group consisting of Cl, Br, $(C_{1-5})$alkyl, $(C_{3-6})$cycloalkyl, $(C_{6-10})$aryl, $(C_{6-10})$aryl$(C_{1-4})$alkyl, $(C_{1-5})$alkylNHC(=O)—, $(C_{1-5})$alkoxyC(=O)—, $R^aR^bNC$(=O)—, $(C_{1-5})$alkylC(=O)—, $(C_{6-10})$arylC(=O)—, $(C_{6-10})$aryl$(C_{1-4})$alkylC(=O)—, $(C_{6-14})$aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, $(C_{1-5})$alkyl, $(C_{3-6})$cycloalkyl, $(C_{1-5})$alkylNHC(=O)—, $(C_{1-5})$alkylC(=O)—, $(C_{6-14})$aryl, $(C_{6-10})$aryl$(C_{1-4})$alkyl, heteroaryl comprising 4 to 10 ring atoms with at least one heteroatom selected from O, S and N in the ring, or heterocyclyl$(C_{1-4})$ alkyl, the heterocycloalkyl group containing 2-10 carbon atoms and 1 to 4 heteroatoms selected from N, O or S;

Z is selected from the group consisting of —SO$_3$H, —PO$_3$H$_2$, a salt or ester thereof, and an acid isostere thereof but not —C(=O)OH; or is selected from the group consisting of —S(=O)$_2$NR$^c$R$^d$, —S(=O)$_2$NHC(=O)R$^e$, S(=O)$_2$C(=O)NR$^c$R$^d$, —S(=O)$_2$NR$^c$C(=O)NR$^c$R$^d$ and —S(=O)$_2$(N=)C(OH)NR$^c$R$^d$, wherein R$^c$ and R$^d$ are each independently hydrogen or is independently selected from the group consisting of $(C_{1-5})$alkyl, $(C_{3-6})$cycloalkyl, $(C_{1-5})$alkylNHC(=O)—, $(C_{1-5})$alkylC(=O)—, $(C_{6-10})$arylC(=O)—, $(C_{6-10})$aryl$(C_{1-4})$C(=O)—, $(C_{6-14})$aryl, $(C_{6-10})$aryl$(C_{1-4})$alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S, and R$^e$ is hydrogen or is selected from the group consisting of $(C_{1-5})$alkyl, $(C_{3-6})$cycloalkyl, $(C_{6-14})$aryl, $(C_{6-10})$aryl$(C_{1-4})$alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S;

or a salt, an amine oxide thereof, or a derivative or a bioisostere or a pro-drug thereof.

2. The compound of claim 1, wherein:

$R_1$ and $R_0$ together with the carbon atoms to which they are attached form a ring with 4 to 7 carbon ring members, wherein optionally one or two ring members are nitrogen and optionally $R_{00}$ is a double bond attached to the carbon atom to which $R_2$ is attached.

3. The compound of claim 1, wherein:

when $X_1$ is chloro or bromo, $X_2$ together with $R_0$ form an alkylenyl group with 1 to 4 carbon atoms, the alkylenyl group together with —NX$_1$— and the carbon atom having the $R_1$ and $R_2$ groups and the carbon atom having the $R_{00}$ and the —Y—Z groups form a saturated heterocyclic ring in which one or two methylene groups may be replaced with a substituted methylene group, the substituents being fluoro, chloro or $(C_{1-5})$alkyl, or replaced with —NR'— or >C=O, whereas R' is hydrogen or is selected from the group consisting of Cl, Br, $(C_{1-5})$alkyl, $(C_{3-6})$cycloalkyl, $(C_{6-10})$aryl, $(C_{6-10})$aryl$(C_{1-4})$alkyl, $(C_{1-5})$alkylNHC(=O)—, $(C_{1-5})$alkoxyC(=O)—, $R^aR^bNC$(=O)—, $(C_{1-5})$alkylC(=O)—, $(C_{6-10})$arylC(=O)—, $(C_{6-10})$aryl$(C_{1-4})$alkylC(=O)—, $(C_{6-14})$aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, $(C_{1-5})$alkyl, $(C_{3-6})$cycloalkyl, $(C_{1-5})$alkylNHC(=O)—, $(C_{1-5})$alkylC (=O)—, ($C_{6-14}$)aryl, ($C_{6-10}$)aryl($C_{1-4}$)alkyl, heteroaryl comprising 4 to 10 ring atoms with at least one heteroatom selected from O, S and N in the ring, or heterocyclyl ($C_{1-4}$)alkyl, the heterocycloalkyl group containing 2-10 carbon atoms and 1 to 4 heteroatoms selected from N, O or S.

4. A compound having the formula II:

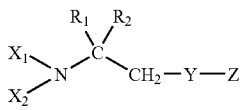

II wherein:

$X_1$ is chloro or bromo;

$X_2$ is hydrogen or is selected from the group consisting of chloro, bromo, ($C_{1-5}$)alkyl, ($C_{3-6}$)cycloalkyl, ($C_{3-6}$)cycloalkyl($C_{1-3}$)alkyl and halo($C_{1-5}$)alkyl;

$R_1$ and $R_2$ are each independently selected from the group consisting of ($C_{1-5}$)alkyl, halo($C_{1-5}$)alkyl, ($C_{3-12}$)cycloalkyl, ($C_{3-6}$)cycloalkyl($C_{1-3}$)alkyl, ($C_{6-10}$)aryl($C_{1-4}$)alkyl, ($C_{6-14}$)aryl and heterocyclyl containing 2-10 carbon atoms and 1 to 4 heteroatoms selected from N, O or S, or $R_1$ and $R_2$ together with the carbon atom to which they are attached to form a ($C_{3-12}$)carbocyclic or ($C_{3-12}$) heterocyclic ring with at least one heteroatom selected from N, O, or S in the ring;

Y is a member selected from a single bond, —O—, and a divalent ($C_{1-18}$)alkylenyl group in which optionally one or two methylene groups are replaced with a mono- or di-substituted methylene group, or optionally where one or two methylene groups are replaced with 1 or 2 —NR'—, —O—, —S—, —S(=O)—, >C=O, —C(=O)O—, —OC(=O)—, —C(=O)NH—, —NHC(=O)—, —C(=O)NR'—, —NR'C(=O)—, —S(=O)$_2$—, —S(=O)$_2$NR'—, —S(=O)$_2$NH—, —NR'S(=O)$_2$—, or —NHS(=O)$_2$—, where R' is hydrogen or is selected from the group consisting of Cl, Br, ($C_{1-5}$)alkyl, ($C_{3-6}$)cycloalkyl, ($C_{6-10}$)aryl, ($C_{6-10}$)aryl($C_{1-4}$)alkyl, ($C_{1-5}$)alkylNHC(=O)—, ($C_{1-5}$)alkoxyC(=O)—, $R^aR^bNC$(=O)—, ($C_{1-5}$)alkylC(=O)—, ($C_{6-10}$)arylC(=O)—, ($C_{6-10}$)aryl($C_{1-4}$)alkylC(=O)—, ($C_{6-14}$)aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, ($C_{1-5}$)alkyl, ($C_{3-6}$)cycloalkyl, ($C_{1-5}$)alkylNHC(=O)—, ($C_{1-5}$)alkylC(=O)—, ($C_{6-14}$)aryl, ($C_{6-10}$)aryl($C_{1-4}$)alkyl, heteroaryl comprising 4 to 10 ring atoms with at least one heteroatom selected from O, S and N in the ring, or heterocyclyl($C_{1-4}$) alkyl, the heterocycloalkyl group containing 2-10 carbon atoms and 1 to 4 heteroatoms selected from N, O or S;

wherein when $R_1$ is ($C_{1-5}$)alkyl or $R_1$ and $R_2$ together with the carbon atom to which they attach form a ($C_{3-6}$) cycloalkyl, then $X_2$ must be ($C_{1-5}$)alkyl, ($C_{3-6}$)cycloalkyl, ($C_{3-6}$)cycloalkyl($C_{1-3}$)alkyl, or halo($C_{1-5}$)alkyl; or when $R_1$ is ($C_{1-5}$)alkyl, then $R_2$ must be halo($C_{1-5}$)alkyl, ($C_{3-12}$)cycloalkyl or ($C_{3-6}$)cycloalkyl-$C_{1-3}$ alkyl; or when $R_1$ is ($C_{1-5}$)alkyl or $R_1$ and $R_2$ together with the carbon atom to which they attach form a ($C_{3-6}$)cycloalkyl, then Y must be —O— or a divalent ($C_{1-18}$) alkylenyl group wherein one or two methylene groups are replaced with a substituted methylene group or by —NR'—, —O—, >C=O, —C(=O)O—, —OC(=O)—, —C(=O)NH—, —NHC(=O)—, —C(=O)NR'—, —NR'C(=O)—, —S—, —S(=O)—, —S(=O)$_2$—, —S(=O)$_2$NR'—, —S(=O)$_2$NH—, —NR'S(=O)$_2$—, or —NHS(=O)$_2$—, where R' is hydrogen or is selected from the group consisting of Cl, Br, ($C_{1-5}$)alkyl, ($C_{3-6}$)cycloalkyl, ($C_{6-10}$)aryl, ($C_{6-10}$)aryl($C_{1-4}$)alkyl, ($C_{1-5}$)alkylNHC(=O)—, ($C_{1-5}$)alkoxyC(=O)—, $R^aR^bNC$(=O)—, ($C_{1-5}$)alkylC(=O)—, ($C_{6-10}$)arylC(=O)—, ($C_{6-10}$)aryl($C_{1-4}$)alkylC(=O)—, ($C_{6-14}$)aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein $R^a$ and $R^b$ are each independently hydrogen, ($C_{1-5}$)alkyl, ($C_{3-6}$)cycloalkyl, ($C_{1-5}$)alkylNHC(=O)—, ($C_{1-5}$)alkylC(=O)—, ($C_{6-14}$)aryl, ($C_{6-10}$)aryl($C_{1-4}$)alkyl, heteroaryl comprising 4 to 10 ring atoms with at least one heteroatom selected from O, S and N in the ring, or heterocyclyl($C_{1-4}$) alkyl, the heterocycloalkyl group containing 2-10 carbon atoms and 1 to 4 heteroatoms selected from N, O or S;

Z is selected from the group consisting of —SO$_3$H, —PO$_3$H$_2$, a salt or ester thereof, and an acid isostere thereof but not —C(=O)OH; or is selected from the group consisting of —S(=O)$_2$NR$^c$R$^d$, —S(=O)$_2$NHC(=O)R$^e$, S(=O)$_2$OC(=O)NR$^c$R$^d$, —S(=O)$_2$NR$^c$C(=O)NR$^c$R$^d$ and —S(=O)$_2$(N=)C(OH)NR$^c$R$^d$, wherein R$^c$ and R$^d$ are each independently hydrogen or is independently selected from the group consisting of ($C_{1-5}$)alkyl, ($C_{3-6}$)cycloalkyl, ($C_{1-5}$)alkylNHC(=O)—, ($C_{1-5}$)alkylC(=O)—, ($C_{6-10}$)arylC(=O)—, ($C_{6-10}$)aryl($C_{1-4}$)C(=O)—, aryl containing 6 to 14 ring atoms, ($C_{6-10}$)aryl($C_{1-4}$)alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S, and R$^e$ is hydrogen or is selected from the group consisting of ($C_{1-5}$)alkyl, ($C_{3-6}$)cycloalkyl, ($C_{6-14}$)aryl, ($C_{6-10}$)aryl($C_{1-4}$)alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S;

or a salt, an amine oxide thereof, or a derivative or a bioisostere or a prodrug thereof.

5. The compound of claim 4, wherein:

$R_1$ and $R_2$ together with the carbon atom to which they are attached to form a ($C_{4-7}$)carbocyclic or ($C_{3-6}$)heterocyclic ring;

or a salt thereof.

6. The compound of claim 4, wherein:

$R_1$ and $R_2$ are each independently halo($C_{1-5}$)alkyl or a 5-12 member heterocyclyl comprising 1 to 4 members selected from —NR'—, —O—, —S—, where R' is hydrogen or is selected from the group consisting of ($C_{1-5}$)alkyl, ($C_{3-6}$)cycloalkyl, ($C_{1-5}$)alkylNHC(=O)—, ($C_{1-5}$)alkoxyC(=O)—, ($C_{1-5}$)alkylC(=O)—, ($C_{6-10}$)arylC(=O)—, ($C_{6-10}$)aryl($C_{1-4}$)alkylC(=O)—, ($C_{6-14}$)aryl, ($C_{6-10}$)aryl($C_{1-4}$)alkyl, heteroaryl comprising 4 to 10 ring atoms with at least one heteroatom selected from O, S and N in the ring and heterocyclyl containing 2-10 carbon atoms and 1 to 4 heteroatoms selected from N, O or S;

Y is a divalent ($C_{1-18}$)alkylenyl group; and

Z is selected from the group consisting of —SO$_3$H, —PO$_3$H$_2$, —S(=O)$_2$NR$^c$R$^d$, —S(=O)$_2$NHC(=O)R$^e$, —S(=O)$_2$C(=O)NR$^c$R$^d$, —S(=O)$_2$NR$^c$C(=O)NR$^c$R$^d$ and —S(O)$_2$(N=)C(OH)NR$^c$R$^d$, wherein R$^c$ and R$^d$ are each independently hydrogen, or are independently selected from the group consisting of (C$_{1-5}$)alkyl, (C$_{1-5}$)alkylNHC(=O)—, (C$_{1-5}$)alkylC(=O)—, (C$_{3-6}$)cycloalkyl, aryl containing 6 to 14 ring atoms, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, and R$^e$ is hydrogen or is selected from the group consisting of (C$_{1-5}$)alkyl, (C$_{3-6}$)cycloalkyl, (C$_{6-14}$)aryl, (C$_{6-10}$)aryl(C$_{1-4}$)alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S;

or a salt thereof.

7. The compound of claim 4, wherein:

X$_1$ and X$_2$ are each independently chloro or bromo, or X$_1$ is chloro or bromo and X$_2$ is hydrogen or is selected from the group consisting of (C$_{1-5}$)alkyl, (C$_{3-6}$)cycloalkyl, (C$_{3-6}$)cycloalkyl(C$_{1-3}$)alkyl and halo(C$_{1-5}$)alkyl;

R$_1$ and R$_2$ together with the carbon atom to which they are attached to form a (C$_{3-7}$)heterocyclic ring comprising the heteroatoms selected from the group consisting of N, O and S;

Y is a bond or a divalent (C$_{1-6}$)alkylenyl group; and

Z is —SO$_3$H or —PO$_3$H$_2$;

or a salt thereof.

8. The compound of claim 4, wherein:

X$_1$ and X$_2$ are both chloro; and

Z is —SO$_3$H or —S(=O)$_2$NR$^c$R$^d$, wherein R$^c$ and R$^d$ are each independently hydrogen or is independently selected from the group consisting of (C$_{1-5}$)alkyl, (C$_{3-6}$)cycloalkyl, (C$_{1-5}$)alkylNHC(=O)—, (C$_{1-5}$)alkylC(=O)—, aryl containing 6 to 14 ring atoms, heteroaryl comprising 4 to 10 ring atoms with at least one heteroatom selected from O, S and N in the ring, and heterocyclyl containing 2-10 carbon atoms and 1 to 4 heteroatoms selected from N, O or S;

or a salt thereof.

9. The compound of claim 4, wherein:

R$_1$ and R$_2$ together with the carbon atom to which they are attached form a (C$_{4-7}$)carbocyclic or (C$_{4-7}$)heterocyclic ring containing from 1 to 4 hetero atoms selected from the group consisting of N, O, and S; said ring being interrupted by a member selected from the group consisting of —O—, —S(=O)$_2$—, —NR$_3$—, —CR$_3$R$_3$—, >C=CR$_3$R$_3$, —N[C(=O)NHR$_4$]—, —N[S(=O)$_2$R$_4$]—, —N[S(=O)$_2$NHR$_4$]—, —N[C(=O)R$_5$]— and —N[C(=O)OR$_5$]—;

R$_3$ each independently selected from the group consisting of hydrogen, (C$_{1-5}$)alkyl, (C$_{3-7}$)cycloalkyl, (C$_{3-6}$)cycloalkyl-(C$_{1-3}$)alkyl, (C$_{5-6}$)carbocyclyl where 1, 2 or 3 carbon ring members are optionally replaced by —NR'—, —O—, —S—, —S(=O)— or —S(=O)$_2$—, where R' is hydrogen or is selected from the group consisting of (C$_{1-5}$)alkyl, (C$_{1-5}$)alkylNHC(=O)—, (C$_{1-5}$)alkylC(=O)—, (C$_{3-6}$)cycloalkyl, heterocycloalkyl containing 2-10 carbon atoms and 1 to 4 heteroatoms selected from N, O or S, (C$_{6-12}$)aryl, (C$_{6-12}$)heteroaryl, (C$_{1-4}$)alkyl(C$_{6-10}$)aryl, (C$_{6-10}$)aryl(C$_{1-4}$)alkyl, (C$_{1-5}$)alkylC(=O)—, (C$_{6-10}$)arylC(=O)—, (C$_{6-10}$)aryl(C$_{1-4}$)alkylC(=O)—, (C$_{1-5}$)alkoxyC(=O)— and —S(=O)$_2$NH(C$_{1-5}$)alkyl;

R$_4$ is selected from the group consisting of (C$_{1-5}$)alkyl, (C$_{3-7}$)cycloalkyl, (C$_{3-6}$)cycloalkyl-(C$_{1-3}$)alkyl, (C$_{6-12}$)aryl and (C$_{5-6}$)carbocyclyl where 1, 2, or 3 carbon ring members are replaced by —NR'—, —O—, —S—, —S(=O)— or —S(=O)$_2$—, where R' is hydrogen or is selected from the group consisting of (C$_{1-5}$)alkyl, (C$_{1-5}$)alkylNHC(=O)—, (C$_{1-5}$)alkylC(=O)NH—, (C$_{1-5}$)alkylC(=O)—, (C$_{3-6}$)cycloalkyl, heterocycloalkyl containing 2-10 carbon atoms and 1 to 4 heteroatoms selected from N, O or S, (C$_{6-12}$)aryl, (C$_{6-10}$)aryl(C$_{1-4}$)alkyl, (C$_{6-12}$)heteroaryl, (C$_{1-6}$)alkyl(C$_{6-12}$)aryl, (C$_{6-12}$)aryl (C$_{1-6}$)alkyl, (C$_{1-5}$)alkylC(=O)—, (C$_{1-5}$)alkoxyC(=O)— and —S(=O)$_2$NH(C$_{1-5}$)alkyl;

R$_5$ is selected from the group consisting of (C$_{1-5}$)alkyl, (C$_{1-5}$)alkoxy, (C$_{3-7}$)cycloalkyl, (C$_{3-6}$)cycloalkyl-(C$_{1-3}$)alkyl, (C$_{6-10}$)aryl, (C$_{6-10}$)aryloxy, (C$_{7-12}$)arylalkyl, (C$_{7-12}$)alkylaryl and (C$_{7-12}$)arylalkoxy;

Y is a single bond or a divalent (C$_{1-6}$)alkylene group; and

Z is —SO$_3$H or —PO$_3$H$_2$; or a salt thereof.

10. The compound of claim 4 wherein:

R$_1$ and R$_2$ independently are (C$_{1-5}$)alkyl or halo(C$_{1-5}$)alkyl with 1-5, preferably 1-3 halogen atoms selected from the group of fluoro and chloro;

or a salt thereof.

11. The compound of claim 4 wherein:

Y is a single bond;

or a salt thereof.

12. The compound of claim 4, wherein:

X$_1$ and X$_2$ are both chloro;

R$_1$ and R$_2$ are each independently halo(C$_{1-2}$)alkyl, (C$_{3-12}$)cycloalkyl, (C$_{4-12}$)aryl, (C$_{6-10}$)aryl(C$_{1-2}$)alkyl or (C$_{3-12}$)heterocyclyl comprising 1-4 heteroatoms selected from the group consisting of O, N or S;

Y is a single bond;

Z is selected from the group consisting of —SO$_3$H and —S(=O)$_2$NR$^c$R$^d$ wherein R$^c$ and R$^d$ are each independently hydrogen or selected from the group consisting of (C$_{1-5}$)alkyl, (C$_{1-5}$)alkylNHC(=O)—, (C$_{1-5}$)alkylC(=O)—, (C$_{3-6}$)cycloalkyl, aryl containing 6 to 12 ring atoms, (C$_{6-10}$)aryl(C$_{1-2}$)alkyl, heteroaryl comprising 4 to 10 ring atoms with at least one heteroatom selected from O, S and N in the ring and heterocycloalkyl containing 2-10 carbon atoms and 1 to 4 heteroatoms selected from N, O or S; or a salt thereof.

13. The compound of claim 4, wherein:

X$_1$ and X$_2$ are both chloro; and

R$_1$ and R$_2$ together with the carbon atom to which they are attached to form a (C$_{4-7}$)heterocycloalkyl comprising the group —O—, —S—, —SO—, —SO$_2$— or —NR$_3$—, where R$_3$ is (C$_{1-5}$)alkyl or (C$_{1-5}$)alkylC(=O)—, (C$_{6-10}$)arylC(=O)—, (C$_{6-10}$)aryl(C$_{1-4}$)alkylC(=O)—;

Y is a single bond; and

Z is selected from the group consisting of —SO$_3$H and —S(=O)$_2$NR$^c$R$^d$ wherein R$^c$ and R$^d$ are each independently hydrogen or selected from the group consisting of (C$_{1-5}$)alkyl, (C$_{1-5}$)alkylNHC(=O)—, (C$_{1-5}$)alkylC(=O)—, (C$_{6-10}$)arylC(=O)—, (C$_{6-10}$)aryl(C$_{1-4}$)alkylC(=O)—, (C$_{3-6}$)cycloalkyl, (C$_{6-14}$)aryl, (C$_{6-10}$)aryl(C$_{1-2}$)alkyl, heteroaryl comprising 4 to 10 ring atoms with at least one heteroatom selected from O, S and N in the ring and heterocycloalkyl containing 2-10 carbon atoms and 1 to 4 heteroatoms selected from N, O or S; or a salt thereof.

14. The compound of claim 2 wherein
X₁ is chloro;
Y is a single bond; or
a salt thereof.

15. The compound of claim 4 wherein:
Z is —SO₃H; or
a salt thereof.

16. The compound of claim 15 wherein:
R₁ and R₂ independently are (C₁₋₅)alkyl, halo(C₁₋₅)alkyl, preferably —CF₃; or
a salt thereof.

17. A compound having the formula III:

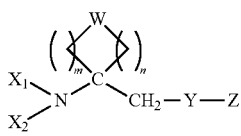

wherein:
m and n are each independently an integer of 0, 1, 2, 3, 4 or 5, and m and n together is 2, 3, 4 or 5;
W is selected from the group consisting of —O—, —S—, —S(=O)—, —S(=O)₂—, —NR₃—, —CR₃R₃—, >C=CR₃R₃, —N[C(=O)NHR₄]—, —N[S(=O)₂R₄]—, —N[S(=O)₂NHR₄]—, —N[C(=O)R₅]—, —NR₄C(=O)—, >C=O, and —N[C(=O)OR₅]—;
Y is a member selected from a single bond, —O—, and a divalent (C₁₋₁₈)alkylenyl group in which optionally one or two methylene groups are replaced with a mono- or di-substituted methylene group, or optionally where one or two methylene groups are replaced with 1 or 2 —NR'—, —O—, —S—, —S(=O)—, >C=O, —C(=O)O—, —OC(=O)—, —C(=O)NH—, —NHC(=O)—, —C(=O)NR'—, —NR'C(=O)—, —S(=O)₂—, —S(=O)₂NR'—, —S(=O)₂NH—, —NR'S(=O)₂—, or —NHS(=O)₂—, where R' is hydrogen or is selected from the group consisting of Cl, Br, (C₁₋₅)alkyl, (C₃₋₆)cycloalkyl, (C₆₋₁₀)aryl, (C₆₋₁₀)aryl(C₁₋₄)alkyl, (C₁₋₅)alkylNHC(=O)—, (C₁₋₅)alkoxyC(=O)—, RᵃRᵇNC(=O)—, (C₁₋₅)alkylC(=O)—, (C₆₋₁₀)arylC(=O)—, (C₆₋₁₀)aryl(C₁₋₄)alkylC(=O)—, (C₆₋₁₄)aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein Rᵃ and Rᵇ are each independently hydrogen, (C₁₋₅)alkyl, (C₃₋₆)cycloalkyl, (C₁₋₅)alkylNHC(=O)—, (C₁₋₅)alkylC(=O)—, (C₆₋₁₄)aryl, (C₆₋₁₀)aryl(C₁₋₄)alkyl, heteroaryl comprising 4 to 10 ring atoms with at least one heteroatom selected from O, S and N in the ring, or heterocyclyl(C₁₋₄) alkyl, the heterocycloalkyl group containing 2-10 carbon atoms and 1 to 4 heteroatoms selected from N, O or S;
Z is selected from the group consisting of —SO₃H, —PO₃H₂, —S(=O)₂NRᶜRᵈ, —S(=O)₂NHC(=O)Rᵉ, —S(=O)₂NRᶜC(=O)NRᶜRᵈ, —S(=O)₂OC(=O)NRᶜRᵈ and —S(=O)₂(N=)C(OH)NRᶜRᵈ, wherein Rᶜ and Rᵈ are each independently hydrogen or are selected from the group consisting of (C₁₋₅)alkyl, (C₁₋₅)alkylNHC(=O)—, (C₁₋₅)alkylC(=O)—, (C₃₋₆)cycloalkyl, aryl containing 6 to 14 ring atoms, (C₆₋₁₀)aryl(C₁₋₄)alkyl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, and Rᵉ is hydrogen or is selected from the group consisting of (C₁₋₅)alkyl, (C₃₋₆)cycloalkyl, (C₆₋₁₄)aryl, (C₆₋₁₀)aryl(C₁₋₄)alkyl, heteroaryl comprising 4 to 10 ring atoms with at least one heteroatom selected from O, S and N in the ring, and heterocyclyl containing 2-10 carbon atoms and 1 to 4 heteroatoms selected from N, O or S;
X₁ is chloro or bromo;
X₂ is hydrogen or is selected from the group consisting of chloro, bromo, (C₁₋₅)alkyl, (C₃₋₆)cycloalkyl, (C₃₋₆)cycloalkyl (C₁₋₃)alkyl and halo(C₁₋₅)alkyl;
R₃ is each independently selected from the group consisting of hydrogen, (C₁₋₅)alkyl, (C₃₋₇)cycloalkyl, (C₃₋₆)cycloalkyl-(C₁₋₃)alkyl, (C₅₋₆)carbocyclyl where 1, 2 or 3 carbon ring members are optionally replaced by —NR'—, —O—, —S—, —S(=O)— or —S(=O)₂—, where R' is hydrogen or is selected from the group consisting of Cl, Br, (C₁₋₅)alkyl, (C₃₋₆)cycloalkyl, (C₆₋₁₀)aryl, (C₆₋₁₀)aryl(C₁₋₄)alkyl, (C₁₋₅)alkylNHC(=O)—, (C₁₋₅)alkoxyC(=O)—, RᵃRᵇNC(=O)—, (C₁₋₅)alkylC(=O)—, (C₆₋₁₀)arylC(=O)—, (C₆₋₁₀)aryl(C₁₋₄)alkylC(=O)—, (C₆₋₁₄)aryl, heteroaryl comprising 4 to 10 ring atoms with at least one heteroatom selected from O, S and N in the ring, and heterocycloalkyl containing 2-10 carbon atoms and 1 to 4 heteroatoms selected from N, O or S, wherein Rᵃ and Rᵇ are each independently hydrogen, (C₁₋₅)alkyl, (C₃₋₆)cycloalkyl, (C₁₋₅)alkylNHC(=O)—, (C₁₋₅)alkylC(=O)—, (C₆₋₁₄)aryl, (C₆₋₁₀)aryl(C₁₋₄)alkyl, heteroaryl comprising 4 to 10 ring atoms with at least one heteroatom selected from O, S and N in the ring, or heterocyclyl(C₁₋₄) alkyl, the heterocycloalkyl group containing 2-10 carbon atoms and 1 to 4 heteroatoms selected from N, O or S;
R₄ is selected from the group consisting of (C₁₋₅)alkyl, (C₃₋₇)cycloalkyl, (C₃₋₆)cycloalkyl-(C₁₋₃)alkyl, (C₆₋₁₂)aryl and (C₅₋₆)carbocycloalkyl where 1, 2 or 3 carbon ring members are replaced by —NR'—, —O—, —S—, —S(=O)— or —S(=O)₂—, where R' is hydrogen or is selected from the group consisting of (C₁₋₅)alkyl, (C₁₋₅)alkylNHC(=O)—, (C₁₋₅)alkylC(=O)—, (C₃₋₆)cycloalkyl, heterocycloalkyl containing 2-10 carbon atoms and 1 to 4 heteroatoms selected from N, O or S, (C₆₋₁₂)aryl, (C₆₋₁₀)aryl(C₁₋₄)alkyl, (C₆₋₁₂)heteroaryl, (C₁₋₆)alkylaryl, (C₆₋₁₂)aryl (C₁₋₆)alkyl, (C₁₋₅)alkylC(=O)—, (C₁₋₅)alkoxyC(=O)— and —S(=O)₂NH (C₁₋₅)alkyl;
R₅ is selected from the group consisting of (C₁₋₅)alkyl, (C₁₋₅)alkoxy, (C₃₋₇)cycloalkyl, (C₃₋₆)cycloalkyl-(C₁₋₃)alkyl, (C₆₋₁₀)aryl, (C₆₋₁₀)aryloxy, (C₇₋₁₂)arylalkyl, (C₇₋₁₂)alkylaryl and (C₇₋₁₂)arylalkoxy;
and wherein W is a group other than —CH₂—, then X₁ and X₂ are as defined above;
and when W is the group —CH₂—, then X₂ is not hydrogen, chloro or bromo;
or optionally when W is a tertiary amine, or when —NR'— is a tertiary amine, or an amine-oxide thereof;
or a salt or derivative or bioisostere or prodrug thereof.

18. The compound of claim 17, wherein:
W is selected from the group consisting of —O—, —S(=O)₂—, —NR₃—, —CR₃R₃—, >C=CR₃R₃, —N[C(=O)NHR₄]—, —N[S(=O)₂R₄]—, —N[S(=O)₂NHR₄]—, —N[C(=O)R₅]— and —N[C(=O)OR₅]—;
R₃, R₄ and R₅ are as defined above;
Y is a single bond or a divalent (C₁₋₅)alkylenyl group; and
Z is —SO₃H or —PO₃H₂;

or a salt thereof.

19. The compound of claim 4, wherein:
   $X_1$ is chloro and $X_2$ is —$CF_3$;
   $R_1$ and $R_2$ together with the carbon atom to which they are attached form a $C_{(3-12)}$carbocyclic ring;
   Y is a single bond;
   or a salt, an amine oxide thereof, or a derivative or a bioisostere or a prodrug thereof.

20. The compound of claim 4 that is:
   2-(dichloroamino)-2-trifluoromethyl-3,3,3-trifluoropropane-1-sulfonic acid;
   2-(chloro(methyl)amino)-2-methylpropane-1-sulfonic acid;
   2-(dichloroamino)-2-methyl-1,1-di-trifluoromethylpropane-1-sulfonic acid;
   2-(chloro(methyl)amino)-1,1,2-trimethylpropane-1-sulfonic acid;
   2-(dibromoamino)-2-methylpropane-1-sulfonic acid;
   2-(bromo(trifluoromethyl)amino)-2-methylpropane-1-sulfonic acid;
   2-(dibromoamino)-1,1,2-trimethylpropane-1-sulfonic acid;
   2-(bromo(methyl)amino)-1,1,2-trimethylpropane-1-sulfonic acid;
   3-(dichloroamino)-2,2,3-trimethylbutane-1-sulfonic acid;
   3-(chloro(methyl)amino)-3-methylbutane-1-sulfonic acid;
   2-(dichloroamino)-2-trifluoromethylpropane-1-sulfonic acid;
   2-(chloro(trifluoromethyl)amino)-2-trifluoromethylpropane-1-sulfonic acid;
   4-(dichloroamino)-3,3,4-trimethylpentane-1-sulfonic acid;
   2-(dichloroamino)-1,2-di-methyl-1-ethylpropane-1-sulfonic acid;
   3-(chloro(methyl)amino)-propylphosphonic acid;
   5-(dibromoamino)-5-methyl-1-methylhexylphosphonic acid;
   5-(bromo(trifluoromethyl)amino)-5-methylhexylphosphonic acid;
   diethyl 2-(dichloroamino)-2-methylpropylphosphonate;
   diethyl 2-(chloro(trifluoromethyl)amino)-2-ethylbutylphosphonate;
   2-(dichloroamino)-2-cyclopropyl-1-methylpropylphosphonic acid;
   2-(chloro(2',2',2'-trifluoroethyl)amino)-2-methyl-1-methylpropylphosphonic acid;
   2-(dichloroamino)-propylphosphonic acid;
   2-(chloro(methyl)amino)-2-pentafluoroethylpropylphosphonic acid;
   3-(dichloroamino)-3-methylbutylphosphonic acid;
   6-(chloro(trifluoromethyl)amino)-2,6-dimethylheptylphosphonic acid;
   4-(dichloroamino)-2,4-dimethypentylphosphonic acid;
   8-(dichloroamino)-7,8-dimethylnonylphosphonic acid;
   8-(chloro(methyl)amino)-8-methylnonylphosphonic acid;
   3-(4-chlorophenyl)-2-(dichloroamino)-2-methylpropane-1-sulfonic acid;
   3-(4-chlorophenyl)-2-(chloroamino)-2-methylpropane-1-sulfonic acid;
   3-(2-(dichloroamino)-2-methylpropoxy)propane-1-sulfonic acid;
   3-(2-(chloroamino)-2-methylpropoxy)propane-1-sulfonic acid;
   3-(2-(dichloroamino)-2-methylpropoxy)-3-oxopropane-1-sulfonic acid;
   3-(2-(chloroamino)-2-methylpropoxy)-3-oxopropane-1-sulfonic acid;
   3-(2-(dichloroamino)-2-methylpropylamino)-3-oxopropane-1-sulfonic acid;
   3-(2-(chloroamino)-2-methylpropylamino)-3-oxopropane-1-sulfonic acid;
   3-((2-(dichloroamino)-2-methylpropyl)(methyl)amino)-3-oxopropane-1-sulfonic acid;
   3-((2-(chloroamino)-2-methylpropyl)(methyl)amino)-3-oxopropane-1-sulfonic acid;
   3-(2-(dichloroamino)-2-methylpropoxy)-2,2-dimethyl-3-oxopropane-1-sulfonic acid;
   3-(2-(chloroamino)-2-methylpropoxy)-2,2-dimethyl-3-oxopropane-1-sulfonic acid;
   2-(3-(dichloroamino)-3-methylbutanoyloxy)ethanesulfonic acid;
   2-(3-(chloroamino)-3-methylbutanoyloxy)ethanesulfonic acid;
   2-(2-(dichloroamino)-2-methylpropylsulfonyl)ethanesulfonic acid;
   2-(2-(chloroamino)-2-methylpropylsulfonyl)ethanesulfonic acid;
   2-(dichloroamino)-N,N-2-trimethylpropane-1-sulfonamide;
   2-(chloroamino)-N,N-2-trimethylpropane-1-sulfonamide;
   2-(dichloroamino)-N,2-dimethylpropane-1-sulfonamide;
   2-(chloroamino)-N,2-dimethylpropane-1-sulfonamide;
   N-(2-(dichloroamino)-2-methylpropylsulfonyl)acetamide;
   N-(2-(chloroamino)-2-methylpropylsulfonyl)acetamide;
   (1-(dichloroamino)cycloheptyl)methanesulfonic acid; and
   (1-(chloroamino)cycloheptyl)methanesulfonic acid; and the pharmaceutically acceptable salts thereof.

21. A pharmaceutical composition comprising a compound or a salt of claim 1 and a pharmaceutically acceptable excipient, optionally combined with halogenated compounds derived from hypohalous acid derivatives or a source of a hypohalous acid derivative.

22. A pharmaceutical composition of claim 21 for the treatment of a bacterial, microbial, sporal, fungal or viral infection.

23. A method of treating an infection caused by a bacterial, a microbial, a sporal, a fungal or a viral activity in a mammal, the method comprising the administration of a bactericidal, antibacterial, anti-infective, antimicrobial, sporicidal, disinfectant, antifungal or antiviral amount of an N-halo- or N,N-dihalo-amino compound or salt of claim 1 or a pharmaceutical composition containing the compound or salt thereof, optionally combined with halogenated compounds derived from hypohalous acid derivatives or a source of a hypohalous acid derivative.

24. A method of treating a nasal or nasopharyngeal infection caused by a bacterial, a microbial, a sporal, a fungal or a viral activity in a mammal, the method comprising the administration of a bactericidal, antibacterial, anti-infective, antimicrobial, sporicidal, disinfectant, antifungal or antiviral amount of an N-halo- or N,N-dihalo-amino compound or salt of claim 1 or a pharmaceutical composition containing the compound or salt thereof, optionally combined with halogenated compounds derived from hypohalous acid derivatives or a source of a hypohalous acid derivative.

* * * * *